(12) United States Patent
Loh et al.

(10) Patent No.: US 9,822,222 B2
(45) Date of Patent: Nov. 21, 2017

(54) BIODEGRADABLE AND BIOCOMPATIBLE SHAPE MEMORY POLYMERS

(71) Applicant: Agency for Science, Technology and Research, Singapore (SG)

(72) Inventors: Xian Jun Loh, Singapore (SG); Jun Li, Singapore (SG)

(73) Assignee: Agency for Science, Technology and Research, Singapore (SG)

( * ) Notice: Subject to any disclaimer, the term of this patent is extended or adjusted under 35 U.S.C. 154(b) by 0 days.

(21) Appl. No.: 14/748,144

(22) Filed: Jun. 23, 2015

(65) Prior Publication Data

US 2015/0368406 A1 Dec. 24, 2015

Related U.S. Application Data

(63) Continuation of application No. 13/635,797, filed as application No. PCT/SG2011/000108 on Mar. 18, 2011, now Pat. No. 9,089,628.

(60) Provisional application No. 61/315,300, filed on Mar. 18, 2010.

(51) Int. Cl.

| | | |
|---|---|---|
| *A61L 27/50* | (2006.01) | |
| *C08G 81/00* | (2006.01) | |
| *A61L 27/14* | (2006.01) | |
| *A61L 27/58* | (2006.01) | |
| *A61L 29/04* | (2006.01) | |
| *A61L 29/14* | (2006.01) | |
| *A61L 31/04* | (2006.01) | |
| *A61L 31/14* | (2006.01) | |
| *B29C 61/00* | (2006.01) | |
| *C08G 18/42* | (2006.01) | |
| *C08G 18/61* | (2006.01) | |
| *C08G 18/73* | (2006.01) | |
| *C08G 63/08* | (2006.01) | |
| *C08G 63/664* | (2006.01) | |
| *C08G 77/458* | (2006.01) | |
| *C08L 87/00* | (2006.01) | |
| *C09D 187/00* | (2006.01) | |
| *A61K 47/34* | (2017.01) | |
| *C08G 77/16* | (2006.01) | |
| *C08K 5/57* | (2006.01) | |

(52) U.S. Cl.
CPC .............. *C08G 81/00* (2013.01); *A61K 47/34* (2013.01); *A61L 27/14* (2013.01); *A61L 27/50* (2013.01); *A61L 27/58* (2013.01); *A61L 29/04* (2013.01); *A61L 29/14* (2013.01); *A61L 29/148* (2013.01); *A61L 31/04* (2013.01); *A61L 31/14* (2013.01); *A61L 31/148* (2013.01); *B29C 61/003* (2013.01); *C08G 18/4277* (2013.01); *C08G 18/61* (2013.01); *C08G 18/73* (2013.01); *C08G 63/08* (2013.01); *C08G 63/664* (2013.01); *C08G 77/458* (2013.01); *C08L 87/005* (2013.01); *C09D 187/005* (2013.01); *A61L 2400/16* (2013.01); *C08G 77/16* (2013.01); *C08G 2230/00* (2013.01); *C08G 2261/126* (2013.01); *C08G 2280/00* (2013.01); *C08K 5/57* (2013.01); *C08L 2201/12* (2013.01)

(58) Field of Classification Search
None
See application file for complete search history.

(56) References Cited

U.S. PATENT DOCUMENTS

| | | |
|---|---|---|
| 3,624,045 A | 11/1971 | Stivers |
| 4,051,088 A * | 9/1977 | Gibson .............. C08G 59/4292 524/509 |
| 5,049,591 A | 9/1991 | Hayashi et al. |
| 5,330,483 A | 7/1994 | Heaven et al. |
| 5,603,722 A | 2/1997 | Phan et al. |
| 5,674,242 A | 10/1997 | Phan et al. |
| 5,762,630 A | 6/1998 | Bley et al. |
| 5,911,737 A | 6/1999 | Lee et al. |
| 5,954,744 A | 9/1999 | Phan et al. |
| 5,957,966 A | 9/1999 | Schroeppel et al. |
| 5,964,744 A | 10/1999 | Babierz et al. |
| 6,059,815 A | 5/2000 | Lee et al. |
| 6,086,599 A | 7/2000 | Lee et al. |
| 6,090,072 A | 7/2000 | Kratoska et al. |

(Continued)

FOREIGN PATENT DOCUMENTS

| | | |
|---|---|---|
| WO | WO 99/42147 A1 | 8/1999 |
| WO | WO 99/42528 A2 | 8/1999 |

(Continued)

OTHER PUBLICATIONS

International Search Report and Written Opinion dated Jul. 29, 2011 in corresponding PCT application No. PCT/SG2011/000108.
International Preliminary Report on Patentability dated Feb. 7, 2012 in corresponding PCT application No. PCT/SG2011/000108.
Behl et al., Shape-memory polymers. Materials Today. 2007;10(4):20-8.
Buckley et al., Inductively Heated Shape Memory Polymer for the Magnetic Actuation of Medical Devices. IEEE Trans Biomed Eng. 2006;53(10):2075-83.
Cabanlit et al., Polyurethane Shape-Memory Polymers Demonstrate Functional Biocompatibility In Vitro. Macromolecular Bioscience. 2007;7(1):48-55.
Choi et al., Degradable shape-memory polymer networks from oligo[(L-lactide)-ran-glycolide]dimethacrylates. Soft Matter. 2007;3:901-9.

(Continued)

*Primary Examiner* — Jeffrey Mullis
(74) *Attorney, Agent, or Firm* — Wolf, Greenfield & Sacks, P.C.

(57) ABSTRACT

This invention relates to shape memory block copolymers comprising: at least one switching segment having a $T_{trans}$ from 10 to 70° C.; and at least one soft segment, wherein at least one of the switching segments in linked to at least one of the soft segments by at least one linkage, and wherein the copolymer transforms from a first shape to a second shape by application of a first stimulus and the copolymer transforms back to the first shape from the second shape by application of a second stimulus. The shape memory block copolymers may be biocompatible and biodegradable.

20 Claims, 7 Drawing Sheets

(56) References Cited

U.S. PATENT DOCUMENTS

| | | | |
|---|---|---|---|
| 6,102,917 | A | 8/2000 | Maitland et al. |
| 6,160,084 | A | 12/2000 | Langer et al. |
| 6,388,043 | B1 | 5/2002 | Langer et al. |
| 6,858,680 | B2 | 2/2005 | Gunatillake et al. |
| 7,524,914 | B2 | 4/2009 | Mather et al. |
| 8,618,238 | B2 | 12/2013 | Xie et al. |
| 2002/0161114 | A1* | 10/2002 | Gunatillake ............ A61L 27/18 525/100 |
| 2005/0245719 | A1* | 11/2005 | Mather .............. C08G 18/3893 528/60 |
| 2006/0036045 | A1 | 2/2006 | Wilson et al. |

FOREIGN PATENT DOCUMENTS

| | | |
|---|---|---|
| WO | WO 00/03643 A1 | 1/2000 |
| WO | WO 2006/115799 A1 | 11/2006 |
| WO | WO 2007/104757 A1 | 9/2007 |
| WO | WO 2009/020797 A2 | 2/2009 |
| WO | WO 2011/115582 A1 | 9/2011 |

OTHER PUBLICATIONS

Feng et al., Biodegradable Multiblock Copolymers Based on Oligodepsipeptides with Shape-Memory Properties. Macromol Biosci. 2009;9(1):45-54.

Lendlein et al., Biodegradable, Elastic Shape-Memory Polymers for Potential Biomedical Applications. Science.2002;296(5573):1673-6.

Lovinger et al., Morphology and Properties of Polycaprolactone-Poly(dimethyl siloxane)-Polycaprolactone Triblock Copolymers. J Polym Sci B Polym Phys. 1993;31(2):115-23.

Min et al., Biodegradable shape-memory polymer—polylactide-co-poly(glycolide-co-caprolactone) multiblock copolymer. Pat. 2005;16(8):608-15.

Nagahama et al., Biodegradable Shape-Memory Polymers Exhibiting Sharp Thermal Transitions and Controlled Drug Release. Biomacromolecules. 2009;10(7):1789-94.

Rousseau et al., Shape Memory Effect Exhibited by Smectic-C Liquid Crystalline Elastomers. J Am Chem Soc. 2003;125(50):15300-1.

Schoener et al., Shape Memory Polymers with Silicon-Containing Segments. J Mater Chem. 2010;20:1787-93.

Wilson et al., Shape memory polymer therapeutic devices for stroke (Proceedings Paper). Proc. SPIE. ;6007:60070R.

Zhang et al., Poly(ε-caprolactone)-Based Shape Memory Polymers with Variable Polydimethylsiloxane Soft Segment Lengths. J Polym Sci A Polym Chem. 2011;49(3):754-61.

* cited by examiner

BIODEGRADABLE AND BIOCOMPATIBLE SHAPE MEMORY POLYMERS

CROSS REFERENCE TO RELATED APPLICATIONS

This application is a continuation of U.S. application Ser. No. 13/635,797, entitled "Biodegradable and Biocompatible Shape Memory Polymers," filed on Sep. 18, 2012, which is a U.S. National Stage application based on International Application No. PCT/SG2011/000108, entitled "Biodegradable and Biocompatible Shape Memory Polymers," filed on Mar. 18, 2011, which claims the benefit of U.S. Provisional Patent Application Ser. No. 61/315,300, entitled "Fast Response Biodegradable and Biocompatible Shape Memory Polymer," filed on Mar. 18, 2010, each of which is incorporated herein by reference in its entirety.

FIELD

This invention relates to biodegradable and biocompatible shape memory polymers. In particular, the invention relates to biodegradable and biocompatible shape memory block copolymers having short recovery times; compositions, polymer blends and articles comprising the copolymers; and uses thereof in biomedical applications.

BACKGROUND

Materials that 'remember' their history have attracted a lot of attention in research, particularly biomedical applications. Shape memory alloys, such as NiTi, have been studied. These materials have limited shape memory deformation capabilities and do not degrade in the body.

In order to improve the shape memory deformation capabilities, shape memory polymers (SMPs) were developed. SMPs belong to a group of polymers which show dual shape properties. As illustrated in FIG. 1, the polymer can be molded in a particular shape A. This polymer can then be deformed to another shape B. 'Memory' or recovery of shape A can be elicited by a change in the thermal conditions. Such polymers have been proposed for many applications particularly in bio-applications.

Conventional SMPs utilize a combination of 2 crystallizable or rigid segments, one of which is switchable between hard and soft properties at a certain transition temperature ($T_{trans}$). When the material is heated above $T_{trans}$, only one of the crystalline domains will remain. The polymer shape can then be 'fixed' by using the appropriate mold into a shape A. The fixture will be cooled below $T_{trans}$ and can be deformed in any manner into shape B. After deformation, at temperatures below $T_{trans}$, the polymer is unable to recover on its own due to the rigidity imposed by the lower melting crystalline segment. However, when the fixture is heated, the lower melting crystalline segment melts and the fixture returns to shape A. Many SMPs rely on crosslinked polymers which give slow response as the slow relaxation process of the recovery gives rise to a lower elasticity entropy upon recovery. This presence of chemical crosslinks also limits the processability of the SMPs.

Using these polymers, different shapes can be fashioned and inserted into the body as an implant. Upon exposure to body heat, the polymer can form its original shape and secure itself in the targeted area. The time of response for the recovery of the shape for conventional SMPs takes between 10 seconds to hours. This time scale is too long for applications that require an almost instantaneous response.

Furthermore, the materials used for the development of shape memory polymers include materials such as polyurethanes, crosslinked hydrogels, polynorbornene, poly(styrene-block-butadiene) which are not biodegradable. Such materials may not be biocompatible if the use is desired in humans. SMPs for biomedical applications which undergo good recovery after high strain changes are desired.

SUMMARY

In an embodiment, there is provided a shape memory block copolymer comprising: at least one switching segment having a $T_{trans}$ from 10 to 70° C.; and at least one soft segment, wherein at least one of the switching segments is linked to at least one of the soft segments by at least one linkage, and wherein the copolymer transforms from a first shape to a second shape by application of a first stimulus and the copolymer transforms back to the first shape from the second shape by application of a second stimulus. In another embodiment, there is provided a composition comprising the copolymer as described herein and a coating, wherein the coating alters a degradation rate of the copolymer. In a further embodiment, there is provided a composition comprising the copolymer as described herein and a therapeutic agent, a diagnostic agent, a prophylactic agent, or any combination thereof. In still another embodiment, there is provided an article comprising the composition as described herein comprising the copolymer and a therapeutic agent, a diagnostic agent, a prophylactic agent, or any combination thereof.

In another embodiment, there is provided a polymer blend comprising at least one copolymer as described herein. In a further embodiment, there is provided a composition comprising the polymer blend as described herein and a therapeutic agent, a diagnostic agent, a prophylactic agent, or any combination thereof. In still another embodiment, there is provided an article comprising the composition as described herein comprising the polymer blend and a therapeutic agent, a diagnostic agent, a prophylactic agent, or any combination thereof.

DETAILED DESCRIPTION

Figure 1:
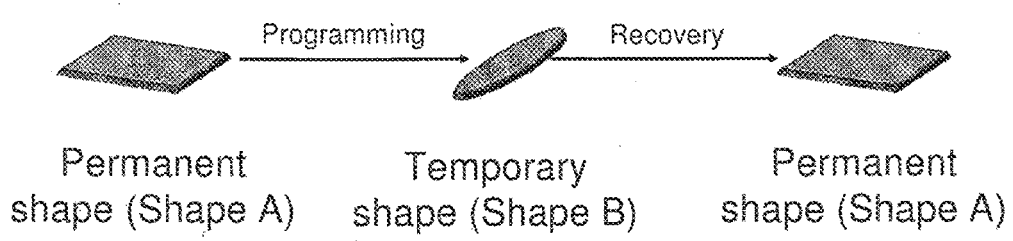
FIG. 1 depicts a schematic outline of how a shape memory polymer functions.

In various embodiments, the invention provides shape memory block copolymers which may comprise: at least one switching segment having a $T_{trans}$ from 10 to 70° C.; and at least one soft segment, wherein at least one of the switching segments may be linked to at least one of the soft segments by at least one linkage, and wherein the copolymer may transform from a first shape to a second shape by application of a first stimulus and the copolymer may transform back to the first shape from the second shape by application of a second stimulus.

As used herein, the expression "block copolymer" is used as it is normally understood to a person of skill in the art and often refers to a copolymer wherein in the constituent macromolecules of the copolymer, adjacent blocks are constitutionally different, i.e. adjacent blocks comprise constitutional units derived from different species of monomer or from the same species of monomer but with a different composition or sequence distribution of constitutional units.

As used herein, the expression "segment" is used as it is normally understood to a person of skill in the art and often refers to a block or sequence of polymer forming a part of the shape memory copolymer.

As used herein, the expression "soft segment" is used as it is normally understood to a person of skill in the art and is a relative term and often refers to a segment having a $T_{trans}$ that is lower than $T_{trans}$ of the switching segment.

In an embodiment, at least one of the switchable segments and/or at least one of the soft segments may comprise, for example, at least one biodegradable region and/or at least one of the switchable segments may be, for example, linked to at least one of the soft segments through at least one biodegradable linkage. In an embodiment, at least one of the switchable segments and at least one of the soft segments may comprise, for example, at least one biodegradable region and at least one of the switchable segments may be, for example, linked to at least one of the soft segments through at least one biodegradable linkage. In an embodiment, at least one of the switchable segments and/or at least one of the soft segments may comprise, for example, at least one biodegradable region. In an embodiment, at least one of the switchable segments and at least one of the soft segments may comprise, for example, at least one biodegradable region. In an embodiment, at least one of the switchable segments may comprise, for example, at least one biodegradable region. In an embodiment, at least one of the soft segments may comprise, for example, at least one biodegradable region. In an embodiment, at least one of the switchable segments may be, for example, linked to at least one of the soft segments through at least one biodegradable linkage. In an embodiment, the at least one biodegradable region may independently be, for example, selected from the group consisting of polyhydroxy acids, poly(ether ester)s, polyorthoesters, poly(amino acids), synthetic poly(amino acids), polyanhydrides, polycarbonates, poly(hydroxyalkanoate)s and poly(ε-caprolactone)s. In an embodiment, the at least one biodegradable linkage may independently be, for example, selected from the group consisting of ester, carbonate, amide, anhydride, and orthoester groups. In an embodiment, the copolymer may be, for example, biodegradable. In an embodiment, the copolymer may be, for example, substantially or completely biodegradable. In an embodiment, the copolymer may lose, for example, at least about 95% of its mass over a period of time. In an embodiment, the copolymer may lose, for example, at least about 75% of its mass over a period of time, or at least about 80% of its mass over a period of time, or at least about 85% of its mass over a period of time, or at least about 90% of its mass over a period of time.

As used herein, the expression "biodegradable" is used as it is normally understood to a person of skill in the art and often refers to copolymers and coatings that are capable of being completely or substantially completely degraded, dissolved and/or eroded over time when exposed to physiological conditions and can be gradually resorbed, absorbed and/or eliminated by the body, or that can be degraded into fragments having sufficiently small molecular weight (for example, 40 kDa or less) to pass through a kidney membrane of an animal. The process giving rise to break down of the copolymer may be caused by, for example, and without limitation, hydrolysis, metabolic processes, oxidation, enzymatic processes, bulk erosion or surface erosion.

The ordering the segments within the copolymer is not particularly limited and any order of the segments within the copolymer may be contemplated. Segments within the copolymer may be arranged, for example, in different orders along the polymer backbone. If there is a directionality to one or more of the segments, any particular segment may be incorporated in either orientation within the copolymer backbone. In an embodiment, the switching segments and soft segments may be, for example, randomly arranged in the copolymer. In an embodiment, the copolymer may be, for example, a random copolymer.

Those of ordinary skill in the art will appreciate that segments of the copolymer may be linked together, for example, by any chemical linkage or functional group, including incorporation of any chemical groups into the polymer backbone in order to link the segments together. Creation of the linkages may result in incorporation of a monomer containing the appropriate reactive functional groups to form the linkages into the backbone. In an embodiment, the monomer involved in linking the segments may be, for example, biocompatible and/or biodegradable. In an embodiment, the monomer involved in linking the segments may be, for example, biocompatible. In an embodiment, the monomer involved in linking the segments may be, for example, biodegradable. In an embodiment, the monomer involved in linking the segments may be, for example, biocompatible and biodegradable. In an embodiment, at least one of the switching segments and at least one of the soft segments may be linked, for example, by urethane linkages. In an embodiment, creation of the urethane linkages may result in incorporation of a monomer containing the appropriate reactive functional groups to form the linkages into the backbone. In an embodiment, for example, alkylene groups may be incorporated, lined adjacent to at least one of the switching segments or at least one of the soft segments by urethane linkages. In an embodiment, the alkylene group may be, for example, a $C_1$-$C_{10}$ alkylene group, or a $C_1$-$C_9$ alkylene group, or a $C_1$-$C_8$ alkylene group, or a $C_1$-$C_7$ alkylene group, or a $C_1$-$C_6$ alkylene group, or a $C_1$-$C_5$ alkylene group, or a $C_1$-$C_4$ alkylene group, or a $C_1$-$C_3$ alkylene group, or a $C_1$-$C_2$ alkylene group, or a $C_1$ alkylene group, or a $C_2$ alkylene group, or a $C_3$ alkylene group, or a $C_4$ alkylene group, or a $C_5$ alkylene group, or a $C_6$ alkylene group, or a $C_7$ alkylene group, or a $C_8$ alkylene group, or a $C_9$ alkylene group, or a $C_{10}$ alkylene group. In an embodiment, the alkylene groups may be, for example, hexamethylene groups. Those of ordinary skill in the art will appreciate that linkages other than urethane linkages may be used to connect the segments within the copolymer. For example, any bi-functional species that contains two reactive groups that react with free hydroxyls may be used to link the segments. In an embodiment, the segments in the copolymer may be linked, for example, by one or more of ester, amide, urethane, carbonate, sulfone, anhydride, urea, orthoester, or sulphur-amide linkages. In an embodiment, the segments in the copolymer may be linked, for example, by one or more of ester, urea, carbonate, anhydride, amide or orthoester linkages. In an embodiment, the $T_{trans}$ may be, for example, a melting point ($T_m$) or glass transition temperature ($T_g$) of at least one of the switching segments. In an embodiment, the $T_{trans}$ may be, for example, a melting point ($T_m$) of at least one of the switching segments. In an embodiment, the $T_{trans}$ may be, for example, a glass transition temperature ($T_g$) of at least one of the switching segments. In an embodiment, at least one of the switching segments may have, for example, a $T_{trans}$ from about 10 to about 70° C., or from about 15 to about 70° C., or from about 20 to about 70° C., or from about 25 to about 70° C., or from about 30 to about 70° C., or from about 35 to about 70° C., or from about 40 to about 70° C., or from about 45 to about 70° C., or from about 50 to about 70° C., or from about 55 to about 70° C., or from about 60 to about 70° C., or from about 65 to about 70° C., or from about 10 to about 65° C., or from about 15 to about 65° C., or from about 20 to about 65° C., or from about 25 to about 65° C., or from about 30 to about 65° C., or from about 35 to about 65° C., or from about 40 to about 65° C., or from about 45 to about 65° C., or from about 50 to about 65° C., or from about 55 to about 65° C., or from about 60 to about 65° C., or from about 10 to about 60° C., or from about 15 to about 60° C., or from about 20 to about 60° C., or from about 25 to about 60° C., or from about 30 to about 60° C., or from about 35 to about 60° C., or from about 40 to about 60° C., or from about 45 to about 60° C., or from about 50 to about 60° C., or from about 55 to about 60° C., or from about 10 to about 55° C., or from about 15 to about 55° C., or from about 20 to about 55° C., or from about 25 to about 55° C., or from about 30 to about 55° C., or from about 35 to about 55° C., or from about 40 to about 55° C., or from about 45 to about 55° C., or from about 50 to about 55° C., or from about 10 to about 50° C., or from about 15 to about 50° C., or from about 20 to about 50° C., or from about 25 to about 50° C., or from about 30 to about 50° C., or from about 35 to about 50° C., or from about 40 to about 50° C., or from about 45 to about 50° C., or from about 10 to about 45° C., or from about 15 to about 45° C., or from about 20 to about 45° C., or from about 25 to about 45° C., or from about 30 to about 45° C., or from about 35 to about 45° C., or from about 40 to about 45° C., or from about 10 to about 40° C., or from about 15 to about 40° C., or from about 20 to about 40° C., or from about 25 to about 40° C., or from about 30 to about 40° C., or from about 35 to about 40° C., or from about 10 to about 35° C., or from about 15 to about 35° C., or from about 20 to about 35° C., or from about 25 to about 35° C., or from about 30 to about 35° C., or from about 10 to about 30° C., or from about 15 to about 30° C., or from about 20 to about 30° C., or from about 25 to about 30° C., or from about 10 to about 25° C., or from about 15 to about 25° C., or from about 20 to about 25° C., or from about 10 to about 20° C., or from about 15 to about 20° C., or from about 10 to about 15° C.

As used herein, the expression "glass transition temperature, $T_g$" is used as it is normally understood to a person of skill in the art and often refers to the temperature at which the amorphous domains of a polymer change from a brittle, glassy, vitreous state to a solid deformable, ductile or rubbery state at atmospheric pressure. The $T_g$ may be dependent on the heating rate and can be influenced by the thermal history of the polymer. As used herein, the expression "melting temperature, $T_m$" is used as it is normally understood to a person of skill in the art and often refers to the temperature at which the crystalline domains of a polymer lose their short- and long-term order, changing from a regular, ordered structure of chain packing to that of a disordered structure.

In an embodiment, the copolymer may rely, for example, on physical interactions between crystalline regions as crosslinking points. Once the crystalline regions are melted, the crosslinks are removed and the copolymer recovers. In an embodiment, at least one of the switching segments may be, for example, a crystallisable segment. In an embodiment, at least one of the switching segments may be, for example, a semicrystalline segment. In an embodiment, at least one of the switching segments may have, for example, crystallinity below $T_{trans}$. In an embodiment, at least one of the switching segments may have, for example, from about 1 wt % crystallinity to about 90 wt % crystallinity below $T_{trans}$, or from about 5 wt % crystallinity to about 90 wt % crystallinity below $T_{trans}$, or from about 10 wt % crystallinity to about 90 wt % crystallinity below $T_{trans}$, or from about 15 wt % crystallinity to about 90 wt % crystallinity below $T_{trans}$, or from about 20 wt % crystallinity to about 90 wt % crystallinity below $T_{trans}$, or from about 25 wt % crystallinity to about 90 wt % crystallinity below $T_{trans}$, or from about 30 wt % crystallinity to about 90 wt % crystallinity below $T_{trans}$, or from about 35 wt % crystallinity to about 90 wt % crystallinity below $T_{trans}$, or from about 40 wt % crystallinity to about 90 wt % crystallinity below $T_{trans}$, or from about 45 wt % crystallinity to about 90 wt % crystallinity below $T_{trans}$, or from about 50 wt % crystallinity to about 90 wt % crystallinity below $T_{trans}$, or from about 55 wt % crystallinity to about 90 wt % crystallinity below $T_{trans}$, or from about 60 wt % crystallinity to about 90 wt % crystallinity below $T_{trans}$, or from about 65 wt % crystallinity to about 90 wt % crystallinity below $T_{trans}$, or from about 70 wt % crystallinity to about 90 wt % crystallinity below $T_{trans}$, or from about 75 wt % crystallinity to about 90 wt % crystallinity below $T_{trans}$, or from about 80 wt % crystallinity to about 90 wt % crystallinity below $T_{trans}$, or from about 85 wt % crystallinity to about 90 wt % crystallinity below $T_{trans}$, or from about 1 wt % crystallinity to about 85 wt % crystallinity below $T_{trans}$, or from about 5 wt % crystallinity to about 85 wt % crystallinity below $T_{trans}$, or from about 10 wt % crystallinity to about 85 wt % crystallinity below $T_{trans}$, or from about 15 wt % crystallinity to about 85 wt % crystallinity below $T_{trans}$, or from about 20 wt % crystallinity to about 85 wt % crystallinity below $T_{trans}$, or from about 25 wt % crystallinity to about 85 wt % crystallinity below $T_{trans}$, or from about 30 wt % crystallinity to about 85 wt % crystallinity below $T_{trans}$, or from about 35 wt % crystallinity to about 85 wt % crystallinity below $T_{trans}$, or from about 40 wt % crystallinity to about 85 wt % crystallinity below $T_{trans}$, or from about 45 wt % crystallinity to about 85 wt % crystallinity below $T_{trans}$, or from about 50 wt % crystallinity to about 85 wt % crystallinity below $T_{trans}$, or from about 55 wt % crystallinity to about 85 wt % crystallinity below $T_{trans}$, or from about 60 wt % crystallinity to about 85 wt % crystallinity below $T_{trans}$, or from about 65 wt % crystallinity to about 85 wt % crystallinity below $T_{trans}$, or from about 70 wt % crystallinity to about 85 wt % crystallinity below $T_{trans}$, or from about 75 wt % crystallinity to about 85 wt % crystallinity below $T_{trans}$, or from about 80 wt % crystallinity to about 85 wt % crystallinity below $T_{trans}$, or from about 1 wt % crystallinity to about 80 wt % crystallinity below $T_{trans}$, or from about 5 wt % crystallinity to about 80 wt % crystallinity below $T_{trans}$, or from about 10 wt % crystallinity to about 80 wt % crystallinity below $T_{trans}$, or from about 15 wt % crystallinity to about 80 wt % crystallinity below $T_{trans}$, or from about 20 wt % crystallinity to about 80 wt % crystallinity below $T_{trans}$, or from about 25 wt % crystallinity to about 80 wt % crystallinity below $T_{trans}$, or from about 30 wt % crystallinity to about 80 wt % crystallinity below $T_{trans}$, or from about 35 wt % crystallinity to about 80 wt % crystallinity below $T_{trans}$, or from about 40 wt % crystallinity to about 80 wt % crystallinity below $T_{trans}$, or from about 45 wt % crystallinity to about 80 wt % crystallinity below $T_{trans}$, or from about 50 wt % crystallinity to about 80 wt % crystallinity below $T_{trans}$, or from about 55 wt % crystallinity to about 80 wt % crystallinity below $T_{trans}$, or from about 60 wt % crystallinity to about 80 wt % crystallinity below $T_{trans}$, or from about 65 wt % crystallinity to about 80 wt % crystallinity below $T_{trans}$, or from about 70 wt % crystallinity to about 80 wt % crystallinity below $T_{trans}$, or from about 75 wt % crystallinity to about 80 wt % crystallinity below $T_{trans}$, or from about 1 wt % crystallinity to about 75 wt % crystallinity below $T_{trans}$, or from about 5 wt % crystallinity to about 75 wt % crystallinity below $T_{trans}$, or from about 10 wt % crystallinity to about 75 wt % crystallinity below $T_{trans}$, or from about 15 wt % crystallinity to about 75 wt % crystallinity below $T_{trans}$, or from about 20 wt % crystallinity to about 75 wt % crystallinity below $T_{trans}$, or from about 25 wt % crystallinity to about 75 wt % crystallinity below $T_{trans}$, or from about 30 wt % crystallinity to about 75 wt % crystallinity below $T_{trans}$, or from about 35 wt % crystallinity to about 75 wt % crystallinity below $T_{trans}$, or from about 40 wt % crystallinity to about 75 wt % crystallinity below $T_{trans}$, or from about 45 wt % crystallinity to about 75 wt % crystallinity below $T_{trans}$, or from about 50 wt % crystallinity to about 75 wt % crystallinity below $T_{trans}$, or from about 55 wt % crystallinity to about 75 wt % crystallinity below $T_{trans}$, or from about 60 wt % crystallinity to about 75 wt % crystallinity below $T_{trans}$, or from about 65 wt % crystallinity to about 75 wt % crystallinity below $T_{trans}$, or from about 70 wt % crystallinity to about 75 wt % crystallinity below $T_{trans}$, or from about 1 wt % crystallinity to about 70 wt % crystallinity below $T_{trans}$, or from about 5 wt % crystallinity to about 70 wt % crystallinity below $T_{trans}$, or from about 10 wt % crystallinity to about 70 wt % crystallinity below $T_{trans}$, or from about 15 wt % crystallinity to about 70 wt % crystallinity below $T_{trans}$, or from about 20 wt % crystallinity to about 70 wt % crystallinity below $T_{trans}$, or from about 25 wt % crystallinity to about 70 wt % crystallinity below $T_{trans}$, or from about 30 wt % crystallinity to about 70 wt % crystallinity below $T_{trans}$, or from about 35 wt % crystallinity to about 70 wt % crystallinity below $T_{trans}$, or from about 40 wt % crystallinity to about 70 wt % crystallinity below $T_{trans}$, or from about 45 wt % crystallinity to about 70 wt % crystallinity below $T_{trans}$, or from about 50 wt % crystallinity to about 70 wt % crystallinity below $T_{trans}$, or from about 55 wt % crystallinity to about 70 wt % crystallinity below $T_{trans}$, or from about 60 wt % crystallinity to about 70 wt % crystallinity below $T_{trans}$, or from about 65 wt % crystallinity to about 70 wt % crystallinity below $T_{trans}$, or from about 1 wt % crystallinity to about 65 wt % crystallinity below $T_{trans}$, or from about 5 wt % crystallinity to about 65 wt % crystallinity below $T_{trans}$, or from about 10 wt % crystallinity to about 65 wt % crystallinity below $T_{trans}$, or from about 15 wt % crystallinity to about 65 wt % crystallinity below $T_{trans}$, or from about 20 wt % crystallinity to about 65 wt % crystallinity below $T_{trans}$, or from about 25 wt % crystallinity to about 65 wt % crystallinity below $T_{trans}$, or from about 30 wt % crystallinity to about 65 wt % crystallinity below $T_{trans}$, or from about 35 wt % crystallinity to about 65 wt % crystallinity below $T_{trans}$, or from about 40 wt % crystallinity to about 65 wt % crystallinity below $T_{trans}$, or from about 45 wt % crystallinity to about 65 wt % crystallinity below $T_{trans}$, or from about 50 wt % crystallinity to about 65 wt % crystallinity below $T_{trans}$, or from about 55 wt % crystallinity to about 65 wt % crystallinity below $T_{trans}$, or from about 60 wt % crystallinity to about 65 wt % crystallinity below $T_{trans}$, or from about 1 wt % crystallinity to about 60 wt % crystallinity below $T_{trans}$, or from about 5 wt % crystallinity to about 60 wt % crystallinity below $T_{trans}$, or from about 10 wt % crystallinity to about 60 wt % crystallinity below $T_{trans}$, or from about 15 wt % crystallinity to about 60 wt % crystallinity below $T_{trans}$, or from about 20 wt % crystallinity to about 60 wt % crystallinity below $T_{trans}$, or from about 25 wt % crystallinity to about 60 wt % crystallinity below $T_{trans}$, or from about 30 wt % crystallinity to about 60 wt % crystallinity below $T_{trans}$, or from about 35 wt % crystallinity to about 60 wt % crystallinity below $T_{trans}$, or from about 40 wt % crystallinity to about 60 wt % crystallinity below $T_{trans}$, or from about 45 wt % crystallinity to about 60 wt % crystallinity below $T_{trans}$, or from about 50 wt % crystallinity to about 60 wt % crystallinity below $T_{trans}$, or from about 55 wt % crystallinity to about 60 wt % crystallinity below $T_{trans}$, or from about 1 wt % crystallinity to about 55 wt % crystallinity below $T_{trans}$, or from about 5 wt % crystallinity to about 55 wt % crystallinity below $T_{trans}$, or from about 10 wt % crystallinity to about 55 wt % crystallinity below $T_{trans}$, or from about 15 wt % crystallinity to about 55 wt % crystallinity below $T_{trans}$, or from about 20 wt % crystallinity to about 55 wt % crystallinity below $T_{trans}$, or from about 25 wt % crystallinity to about 55 wt % crystallinity below $T_{trans}$, or from about 30 wt % crystallinity to about 55 wt % crystallinity below $T_{trans}$, or from about 35 wt % crystallinity to about 55 wt % crystallinity below $T_{trans}$, or from about 40 wt % crystallinity to about 55 wt % crystallinity below $T_{trans}$, or from about 45 wt % crystallinity to about 55 wt % crystallinity below $T_{trans}$, or from about 50 wt % crystallinity to about 55 wt % crystallinity below $T_{trans}$, or from about 1 wt % crystallinity to about 50 wt % crystallinity below $T_{trans}$, or from about 5 wt % crystallinity to about 50 wt % crystallinity below $T_{trans}$, or from about 10 wt % crystallinity to about 50 wt % crystallinity below $T_{trans}$, or from about 15 wt % crystallinity to about 50 wt % crystallinity below $T_{trans}$, or from about 20 wt % crystallinity to about 50 wt % crystallinity below $T_{trans}$, or from about 25 wt % crystallinity to about 50 wt % crystallinity below $T_{trans}$, or from about 30 wt % crystallinity to about 50 wt % crystallinity below $T_{trans}$, or from about 35 wt % crystallinity to about 50 wt % crystallinity below $T_{trans}$, or from about 40 wt % crystallinity to about 50 wt % crystallinity below $T_{trans}$, or from about 45 wt % crystallinity to about 50 wt % crystallinity below $T_{trans}$, or from about 1 wt % crystallinity to about 45 wt % crystallinity below $T_{trans}$, or from about 5 wt % crystallinity to about 45 wt % crystallinity below $T_{trans}$, or from about 10 wt % crystallinity to about 45 wt % crystallinity below $T_{trans}$, or from about 15 wt % crystallinity to about 45 wt % crystallinity below $T_{trans}$, or from about 20 wt % crystallinity to about 45 wt % crystallinity below $T_{trans}$, or from about 25 wt % crystallinity to about 45 wt % crystallinity below $T_{trans}$, or from about 30 wt % crystallinity to about 45 wt % crystallinity below $T_{trans}$, or from about 35 wt % crystallinity to about 45 wt % crystallinity below $T_{trans}$, or from about 40 wt % crystallinity to about 45 wt % crystallinity below $T_{trans}$, or from about 1 wt % crystallinity to about 40 wt % crystallinity below $T_{trans}$, or from about 5 wt % crystallinity to about 40 wt % crystallinity below $T_{trans}$, or from about 10 wt % crystallinity to about 40 wt % crystallinity below $T_{trans}$, or from about 15 wt % crystallinity to about 40 wt % crystallinity below $T_{trans}$, or from about 20 wt % crystallinity to about 40 wt % crystallinity below $T_{trans}$, or from about 25 wt % crystallinity to about 40 wt % crystallinity below $T_{trans}$, or from about 30 wt % crystallinity to about 40 wt % crystallinity below $T_{trans}$, or from about 35 wt % crystallinity to about 40 wt % crystallinity below $T_{trans}$, or from about 1 wt % crystallinity to about 35 wt % crystallinity below $T_{trans}$, or from about 5 wt % crystallinity to about 35 wt % crystallinity below $T_{trans}$, or from about 10 wt % crystallinity to about 35 wt % crystallinity below $T_{trans}$, or from about 15 wt % crystallinity to about 35 wt % crystallinity below $T_{trans}$, or from about 20 wt % crystallinity to about 35 wt % crystallinity below $T_{trans}$, or from about 25 wt % crystallinity to about 35 wt % crystallinity below $T_{trans}$, or from about 30 wt % crystallinity to about 35 wt % crystallinity below $T_{trans}$, or from about 1 wt % crystallinity to about 30 wt % crystallinity below $T_{trans}$, or from about 5 wt % crystallinity to about 30 wt % crystallinity below $T_{trans}$, or from about 10 wt % crystallinity to about 30 wt % crystallinity below $T_{trans}$, or from about 15 wt % crystallinity to about 30 wt % crystallinity below $T_{trans}$, or from about 20 wt % crystallinity to about 30 wt % crystallinity below $T_{trans}$, or from about 25 wt % crystallinity to about 30 wt % crystallinity below $T_{trans}$, or from about 1 wt % crystallinity to about 25 wt % crystallinity below $T_{trans}$, or from about 5 wt % crystallinity to about 25 wt % crystallinity below $T_{trans}$, or from about 10 wt % crystallinity to about 25 wt % crystallinity below $T_{trans}$, or from about 15 wt % crystallinity to about 25 wt % crystallinity below $T_{trans}$, or from about 20 wt % crystallinity to about 25 wt % crystallinity below $T_{trans}$, or from about 1 wt % crystallinity to about 20 wt % crystallinity below $T_{trans}$, or from about 5 wt % crystallinity to about 20 wt % crystallinity below $T_{trans}$, or from about 10 wt % crystallinity to about 20 wt % crystallinity below $T_{trans}$, or from about 15 wt % crystallinity to about 20 wt % crystallinity below $T_{trans}$, or from about 1 wt % crystallinity to about 15 wt % crystallinity below $T_{trans}$, or from about 5 wt % crystallinity to about 15 wt % crystallinity below $T_{trans}$, or from about 10 wt % crystallinity to about 15 wt % crystallinity below $T_{trans}$, or from about 1 wt % crystallinity to about 10 wt % crystallinity below $T_{trans}$, or from about 5 wt % crystallinity to about 10 wt % crystallinity below $T_{trans}$, or from about 1 wt % crystallinity to about 5 wt % crystallinity below $T_{trans}$.

In an embodiment, at least one of the switching segments may be, for example, a thermoplastic polymer. In an embodiment, at least one of the switching segments may be, for example, a biocompatible polymer. In an embodiment, at least one of the switching segments may independently be, for example, a polyhydroxy acid, a poly(ether ester), a polyorthoester, a poly(amino acids), a synthetic poly(amino acids), a polyanhydride, a polycarbonate, a poly(hydroxyalkanoate), a poly(ε-caprolactone), or any combination thereof. In an embodiment, at least one of the switching segments may independently be, for example, a polyhydroxy acid. In an embodiment, at least one of the switching segments may independently be, for example, a poly(ether ester). In an embodiment, at least one of the switching segments may independently be, for example, a polyorthoester. In an embodiment, at least one of the switching segments may independently be, for example, a poly(amino acids). In an embodiment, at least one of the switching segments may independently be, for example, a synthetic poly(amino acids). In an embodiment, at least one of the switching segments may independently be, for example, a polyanhydride. In an embodiment, at least one of the switching segments may independently be, for example, a polycarbonate. In an embodiment, at least one of the switching segments may independently be, for example, a poly(hydroxyalkanoate). In an embodiment, at least one of the switching segments may independently be, for example, a poly(ε-caprolactone) (PCL).

In an embodiment, at least one of the soft segments may have, for example, a melting temperature $T_m$. In an embodiment, at least one of the soft segments may have, for example, a $T_m$ from about −30 to about 30° C., or from about −25 to about 30° C., or from about −20 to about 30° C., or from about −15 to about 30° C., or from about −10 to about 30° C., or from about −5 to about 30° C., or from about 0 to about 30° C., or from about 5 to about 30° C., or from about 10 to about 30° C., or from about 15 to about 30° C., or from about 20 to about 30° C., or from about 25 to about 30° C., or from about −30 to about 25° C., or from about −25 to about 25° C., or from about −20 to about 25° C., or from about −15 to about 25° C., or from about −10 to about 25° C., or from about −5 to about 25° C., or from about 0 to about 25° C., or from about 5 to about 25° C., or from about 10 to about 25° C., or from about 15 to about 25° C., or from about 20 to about 25° C., or from about −30 to about 20° C., or from about −25 to about 20° C., or from about −20 to about 20° C., or from about −15 to about 20° C., or from about −10 to about 20° C., or from about −5 to about 20° C., or from about 0 to about 20° C., or from about 5 to about 20° C., or from about 10 to about 20° C., or from about 15 to about 20° C., or from about −30 to about 15° C., or from about −25 to about 15° C., or from about −20 to about 15° C., or from about −15 to about 15° C., or from about −10 to about 15° C., or from about −5 to about 15° C., or from about 0 to about 15° C., or from about 5 to about 15° C., or from about 10 to about 15° C., or from about −30 to about 10° C., or from about −25 to about 10° C., or from about −20 to about 10° C., or from about −15 to about 10° C., or from about −10 to about 10° C., or from about −5 to about 10° C., or from about 0 to about 10° C., or from about 5 to about 10° C., or from about −30 to about 5° C., or from about −25 to about 5° C., or from about −20 to about 5° C., or from about −15 to about 5° C., or from about −10 to about 5° C., or from about −5 to about 5° C., or from about 0 to about 5° C., or from about −30 to about 0° C., or from about −25 to about 0° C., or from about −20 to about 0° C., or from about −15 to about 0° C., or from about −10 to about 0° C., or from about −5 to about 0° C., or from about −30 to about −5° C., or from about −25 to about −5° C., or from about −20 to about −5° C., or from about −15 to about −5° C., or from about −10 to about −5° C., or from about −30 to about −10° C., or from about −25 to about −10° C., or from about −20 to about −10° C., or from about −15 to about −10° C., or from about −30 to about −15° C., or from about −25 to about −15° C., or from about −20 to about −15° C., or from about −30 to about −20° C., or from about −25 to about −20° C., or from about −30 to about −25° C. In an embodiment, at least one of the soft segments may be, for example, an amorphous segment. In an embodiment, at least one of the soft segments may independently be, for example, a thermoplastic polymer. In an embodiment, at least one of the soft segments may be, for example, a biocompatible polymer. In an embodiment, at least one of the soft segments may independently be, for example, a poly(alkylene glycol) or a poly(dimethylsiloxane) (PDMS). In an embodiment, at least one of the soft segments may independently be, for example, a poly(alkylene glycol). In an embodiment, the poly(alkylene glycol) may be, for example, a poly(ethylene glycol), a poly(ethylene oxide), a polypropylene 1,2-glycol, a polypropylene oxide, a polypropylene 1,3-glycol, or any combination thereof. In an embodiment, the poly(alkylene glycol) may be, for example, a poly(ethylene glycol). In an embodiment, the poly(alkylene glycol) may be, for example, a poly(ethylene oxide). In an embodiment, the poly(alkylene glycol) may be, for example, a polypropylene 1,2-glycol. In an embodiment, the poly(alkylene glycol) may be, for example, a polypropylene oxide. In an embodiment, the poly(alkylene glycol) may be, for example, a polypropylene 1,3-glycol. In an embodiment, at least one of the soft segments may independently be, for example, a poly(dimethylsiloxane) (PDMS).

In an embodiment, the copolymer may be, for example, biocompatible. In an embodiment, the copolymer may not comprise, for example, aromatic groups. As used herein, the phrase "biocompatible" is used as it is normally understood to a person of skill in the art and often refers to a polymer that is non-toxic and does not, or does not significantly irritate tissue or cause an inflammatory or immune response within the body.

In an embodiment, the copolymer may be, for example, a thermosetting polymer.

In an embodiment, the at least one switching segment may be, for example, present in the copolymer based on a total weight of the copolymer in an amount from about 10 wt % to about 99 wt %, or from about 15 wt % to about 99 wt %, or from about 20 wt % to about 99 wt %, or from about 25 wt % to about 99 wt %, or from about 30 wt % to about 99 wt %, or from about 35 wt % to about 99 wt %, or from about 40 wt % to about 99 wt %, or from about 45 wt % to about 99 wt %, or from about 50 wt % to about 99 wt %, or from about 55 wt % to about 99 wt %, or from about 60 wt % to about 99 wt %, or from about 65 wt % to about 99 wt %, or from about 70 wt % to about 99 wt %, or from about 75 wt % to about 99 wt %, or from about 80 wt % to about 99 wt %, or from about 85 wt % to about 99 wt %, or from about 90 wt % to about 99 wt %, or from about 95 wt % to about 99 wt %, or from about 10 wt % to about 95 wt %, or from about 15 wt % to about 95 wt %, or from about 20 wt % to about 95 wt %, or from about 25 wt % to about 95 wt %, or from about 30 wt % to about 95 wt %, or from about 35 wt % to about 95 wt %, or from about 40 wt % to about 95 wt %, or from about 45 wt % to about 95 wt %, or from about 50 wt % to about 95 wt %, or from about 55 wt % to about 95 wt %, or from about 60 wt % to about 95 wt %, or from about 65 wt % to about 95 wt %, or from about 70 wt % to about 95 wt %, or from about 75 wt % to about 95 wt %, or from about 80 wt % to about 95 wt %, or from about 85 wt % to about 95 wt %, or from about 90 wt % to about 95 wt %, or from about 10 wt % to about 90 wt %, or from about 15 wt % to about 90 wt %, or from about 20 wt % to about 90 wt %, or from about 25 wt % to about 90 wt %, or from about 30 wt % to about 90 wt %, or from about 35 wt % to about 90 wt %, or from about 40 wt % to about 90 wt %, or from about 45 wt % to about 90 wt %, or from about 50 wt % to about 90 wt %, or from about 55 wt % to about 90 wt %, or from about 60 wt % to about 90 wt %, or from about 65 wt % to about 90 wt %, or from about 70 wt % to about 90 wt %, or from about 75 wt % to about 90 wt %, or from about 80 wt % to about 90 wt %, or from about 85 wt % to about 90 wt %, or from about 10 wt % to about 85 wt %, or from about 15 wt % to about 85 wt %, or from about 20 wt % to about 85 wt %, or from about 25 wt % to about 85 wt %, or from about 30 wt % to about 85 wt %, or from about 35 wt % to about 85 wt %, or from about 40 wt % to about 85 wt %, or from about 45 wt % to about 85 wt %, or from about 50 wt % to about 85 wt %, or from about 55 wt % to about 85 wt %, or from about 60 wt % to about 85 wt %, or from about 65 wt % to about 85 wt %, or from about 70 wt % to about 85 wt %, or from about 75 wt % to about 85 wt %, or from about 80 wt % to about 85 wt %, or from about 10 wt % to about 80 wt %, or from about 15 wt % to about 80 wt %, or from about 20 wt % to about 80 wt %, or from about 25 wt % to about 80 wt %, or from about 30 wt % to about 80 wt %, or from about 35 wt % to about 80 wt %, or from about 40 wt % to about 80 wt %, or from about 45 wt % to about 80 wt %, or from about 50 wt % to about 80 wt %, or from about 55 wt % to about 80 wt %, or from about 60 wt % to about 80 wt %, or from about 65 wt % to about 80 wt %, or from about 70 wt % to about 80 wt %, or from about 75 wt % to about 80 wt %, or from about 10 wt % to about 75 wt %, or from about 15 wt % to about 75 wt %, or from about 20 wt % to about 75 wt %, or from about 25 wt % to about 75 wt %, or from about 30 wt % to about 75 wt %, or from about 35 wt % to about 75 wt %, or from about 40 wt % to about 75 wt %, or from about 45 wt % to about 75 wt %, or from about 50 wt % to about 75 wt %, or from about 55 wt % to about 75 wt %, or from about 60 wt % to about 75 wt %, or from about 65 wt % to about 75 wt %, or from about 70 wt % to about 75 wt %, or from about 10 wt % to about 70 wt %, or from about 15 wt % to about 70 wt %, or from about 20 wt % to about 70 wt %, or from about 25 wt % to about 70 wt %, or from about 30 wt % to about 70 wt %, or from about 35 wt % to about 70 wt %, or from about 40 wt % to about 70 wt %, or from about 45 wt % to about 70 wt %, or from about 50 wt % to about 70 wt %, or from about 55 wt % to about 70 wt %, or from about 60 wt % to about 70 wt %, or from about 65 wt % to about 70 wt %, or from about 10 wt % to about 65 wt %, or from about 15 wt % to about 65 wt %, or from about 20 wt % to about 65 wt %, or from about 25 wt % to about 65 wt %, or from about 30 wt % to about 65 wt %, or from about 35 wt % to about 65 wt %, or from about 40 wt % to about 65 wt %, or from about 45 wt % to about 65 wt %, or from about 50 wt % to about 65 wt %, or from about 55 wt % to about 65 wt %, or from about 60 wt % to about 65 wt %, or from about 10 wt % to about 60 wt %, or from about 15 wt % to about 60 wt %, or from about 20 wt % to about 60 wt %, or from about 25 wt % to about 60 wt %, or from about 30 wt % to about 60 wt %, or from about 35 wt % to about 60 wt %, or from about 40 wt % to about 60 wt %, or from about 45 wt % to about 60 wt %, or from about 50 wt % to about 60 wt %, or from about 55 wt % to about 60 wt %, or from about 10 wt % to about 55 wt %, or from about 15 wt % to about 55 wt %, or from about 20 wt % to about 55 wt %, or from about 25 wt % to about 55 wt %, or from about 30 wt % to about 55 wt %, or from about 35 wt % to about 55 wt %, or from about 40 wt % to about 55 wt %, or from about 45 wt % to about 55 wt %, or from about 50 wt % to about 55 wt %, or from about 10 wt % to about 50 wt %, or from about 15 wt % to about 50 wt %, or from about 20 wt % to about 50 wt %, or from about 25 wt % to about 50 wt %, or from about 30 wt % to about 50 wt %, or from about 35 wt % to about 50 wt %, or from about 40 wt % to about 50 wt %, or from about 45 wt % to about 50 wt %, or from about 10 wt % to about 45 wt %, or from about 15 wt % to about 45 wt %, or from about 20 wt % to about 45 wt %, or from about 25 wt % to about 45 wt %, or from about 30 wt % to about 45 wt %, or from about 35 wt % to about 45 wt %, or from about 40 wt % to about 45 wt %, or from about 40 wt % to about 45 wt %, or from about 10 wt % to about 40 wt %, or from about 15 wt % to about 40 wt %, or from about 20 wt % to about 40 wt %, or from about 25 wt % to about 40 wt %, or from about 30 wt % to about 40 wt %, or from about 35 wt % to about 40 wt %, or from about 10 wt % to about 35 wt %, or from about 15 wt % to about 35 wt %, or from about 20 wt % to about 35 wt %, or from about 25 wt % to about 35 wt %, or from about 30 wt % to about 35 wt %, or from about 10 wt % to about 30 wt %, or from about 15 wt % to about 30 wt %, or from about 20 wt % to about 30 wt %, or from about 25 wt % to about 30 wt %, or from about 10 wt % to about 25 wt %, or from about 15 wt % to about 25 wt %, or from about 20 wt % to about 25 wt %, or from about 10 wt % to about 20 wt %, or from about 15 wt % to about 20 wt %, or from about 10 wt % to about 15 wt %.

In an embodiment, the at least one soft segment may be, for example, present in the copolymer based on a total weight of the copolymer in an amount from about 1 wt % to about 60 wt %, or from about 5 wt % to about 60 wt %, or from about 10 wt % to about 60 wt %, or from about 15 wt % to about 60 wt %, or from about 20 wt % to about 60 wt %, or from about 25 wt % to about 60 wt %, or from about 30 wt % to about 60 wt %, or from about 35 wt % to about 60 wt %, or from about 40 wt % to about 60 wt %, or from about 45 wt % to about 60 wt %, or from about 50 wt % to about 60 wt %, or from about 55 wt % to about 60 wt %, or from about 1 wt % to about 55 wt %, or from about 5 wt % to about 55 wt %, or from about 10 wt % to about 55 wt %, or from about 15 wt % to about 55 wt %, or from about 20 wt % to about 55 wt %, or from about 25 wt % to about 55 wt %, or from about 30 wt % to about 55 wt %, or from about 35 wt % to about 55 wt %, or from about 40 wt % to about 55 wt %, or from about 45 wt % to about 55 wt %, or from about 50 wt % to about 55 wt %, or from about 1 wt % to about 50 wt %, or from about 5 wt % to about 50 wt %, or from about 10 wt % to about 50 wt %, or from about 15 wt % to about 50 wt %, or from about 20 wt % to about 50 wt %, or from about 25 wt % to about 50 wt %, or from about 30 wt % to about 50 wt %, or from about 35 wt % to about 50 wt %, or from about 40 wt % to about 50 wt %, or from about 45 wt % to about 50 wt %, or from about 1 wt % to about 45 wt %, or from about 5 wt % to about 45 wt %, or from about 10 wt % to about 45 wt %, or from about 15 wt % to about 45 wt %, or from about 20 wt % to about 45 wt %, or from about 25 wt % to about 45 wt %, or from about 30 wt % to about 45 wt %, or from about 35 wt % to about 45 wt %, or from about 40 wt % to about 45 wt %, or from about 1 wt % to about 40 wt %, or from about 5 wt % to about 40 wt %, or from about 10 wt % to about 40 wt %, or from about 15 wt % to about 40 wt %, or from about 20 wt % to about 40 wt %, or from about 25 wt % to about 40 wt %, or from about 30 wt % to about 40 wt %, or from about 35 wt % to about 40 wt %, or from about 1 wt % to about 35 wt %, or from about 5 wt % to about 35 wt %, or from about 10 wt % to about 35 wt %, or from about 15 wt % to about 35 wt %, or from about 20 wt % to about 35 wt %, or from about 25 wt % to about 35 wt %, or from about 30 wt % to about 35 wt %, or from about 1 wt % to about 30 wt %, or from about 5 wt % to about 30 wt %, or from about 10 wt % to about 30 wt %, or from about 15 wt % to about 30 wt %, or from about 20 wt % to about 30 wt %, or from about 25 wt % to about 30 wt %, or from about 1 wt % to about 25 wt %, or from about 5 wt % to about 25 wt %, or from about 10 wt % to about 25 wt %, or from about 15 wt % to about 25 wt %, or from about 20 wt % to about 25 wt %, or from about 1 wt % to about 20 wt %, or from about 5 wt % to about 20 wt %, or from about 10 wt % to about 20 wt %, or from about 15 wt % to about 20 wt %, or from about 1 wt % to about 15 wt %, or from about 5 wt % to about 15 wt %, or from about 10 wt % to about 15 wt %, or from about 1 wt % to about 10 wt %, or from about 5 wt % to about 10 wt %, or from about 1 wt % to about 5 wt %.

In an embodiment, a molar ratio of the switching segments to the soft segments of the copolymer may be, for example 1:1.

In an embodiment, the copolymer may be, for example, a high molecular weight, $M_w$. In an embodiment, the copolymer may have a molecular weight, $M_w$, for example, of from about 50,000 g/mol to about 1,000,000 g/mol, or from about 100,000 g/mol to about 1,000,000 g/mol, or from about 150,000 g/mol to about 1,000,000 g/mol, or from about 200,000 g/mol to about 1,000,000 g/mol, or from about 250,000 g/mol to about 1,000,000 g/mol, or from about 300,000 g/mol to about 1,000,000 g/mol, or from about 350,000 g/mol to about 1,000,000 g/mol, or from about 400,000 g/mol to about 1,000,000 g/mol, or from about 450,000 g/mol to about 1,000,000 g/mol, or from about 500,000 g/mol to about 1,000,000 g/mol, or from about 550,000 g/mol to about 1,000,000 g/mol, or from about 600,000 g/mol to about 1,000,000 g/mol, or from about 650,000 g/mol to about 1,000,000 g/mol, or from about 700,000 g/mol to about 1,000,000 g/mol, or from about 750,000 g/mol to about 1,000,000 g/mol, or from about 800,000 g/mol to about 1,000,000 g/mol, or from about 850,000 g/mol to about 1,000,000 g/mol, or from about 900,000 g/mol to about 1,000,000 g/mol, or from about 950,000 g/mol to about 1,000,000 g/mol, or from about 50,000 g/mol to about 950,000 g/mol, or from about 100,000 g/mol to about 950,000 g/mol, or from about 150,000 g/mol to about 950,000 g/mol, or from about 200,000 g/mol to about 950,000 g/mol, or from about 250,000 g/mol to about 950,000 g/mol, or from about 300,000 g/mol to about 950,000 g/mol, or from about 350,000 g/mol to about 950,000 g/mol, or from about 400,000 g/mol to about 950,000 g/mol, or from about 450,000 g/mol to about 950,000 g/mol, or from about 500,000 g/mol to about 950,000 g/mol, or from about 550,000 g/mol to about 950,000 g/mol, or from about 600,000 g/mol to about 950,000 g/mol, or from about 650,000 g/mol to about 950,000 g/mol, or from about 700,000 g/mol to about 950,000 g/mol, or from about 750,000 g/mol to about 950,000 g/mol, or from about 800,000 g/mol to about 950,000 g/mol, or from about 850,000 g/mol to about 950,000 g/mol, or from about 900,000 g/mol to about 950,000 g/mol, or from about 50,000 g/mol to about 900,000 g/mol, or from about 100,000 g/mol to about 900,000 g/mol, or from about 150,000 g/mol to about 900,000 g/mol, or from about 200,000 g/mol to about 900,000 g/mol, or from about 250,000 g/mol to about 900,000 g/mol, or from about 300,000 g/mol to about 900,000 g/mol, or from about 350,000 g/mol to about 900,000 g/mol, or from about 400,000 g/mol to about 900,000 g/mol, or from about 450,000 g/mol to about 900,000 g/mol, or from about 500,000 g/mol to about 900,000 g/mol, or from about 550,000 g/mol to about 900,000 g/mol, or from about 600,000 g/mol to about 900,000 g/mol, or from about 650,000 g/mol to about 900,000 g/mol, or from about 700,000 g/mol to about 900,000 g/mol, or from about 750,000 g/mol to about 900,000 g/mol, or from about 800,000 g/mol to about 900,000 g/mol, or from about 850,000 g/mol to about 900,000 g/mol, or from about 50,000 g/mol to about 850,000 g/mol, or from about 100,000 g/mol to about 850,000 g/mol, or from about 150,000 g/mol to about 850,000 g/mol, or from about 200,000 g/mol to about 850,000 g/mol, or from about 250,000 g/mol to about 850,000 g/mol, or from about 300,000 g/mol to about 850,000 g/mol, or from about 350,000 g/mol to about 850,000 g/mol, or from about 400,000 g/mol to about 850,000 g/mol, or from about 450,000 g/mol to about 850,000 g/mol, or from about 500,000 g/mol to about 850,000 g/mol, or from about 550,000 g/mol to about 850,000 g/mol, or from about 600,000 g/mol to about 850,000 g/mol, or from about 650,000 g/mol to about 850,000 g/mol, or from about 700,000 g/mol to about 850,000 g/mol, or from about 750,000 g/mol to about 850,000 g/mol, or from about 800,000 g/mol to about 850,000 g/mol, or from about 50,000 g/mol to about 800,000 g/mol, or from about 100,000 g/mol to about 800,000 g/mol, or from about 150,000 g/mol to about 800,000 g/mol, or from about 200,000 g/mol to about 800,000 g/mol, or from about 250,000 g/mol to about 800,000 g/mol, or from about 300,000 g/mol to about 800,000 g/mol, or from about 350,000 g/mol to about 800,000 g/mol, or from about 400,000 g/mol to about 800,000 g/mol, or from about 450,000 g/mol to about 800,000 g/mol, or from about 500,000 g/mol to about 800,000 g/mol, or from about 550,000 g/mol to about 800,000 g/mol, or from about 600,000 g/mol to about 800,000 g/mol, or from about 650,000 g/mol to about 800,000 g/mol, or from about 700,000 g/mol to about 800,000 g/mol, or from about 750,000 g/mol to about 800,000 g/mol, or from about 50,000 g/mol to about 750,000 g/mol, or from about 100,000 g/mol to about 750,000 g/mol, or from about 150,000 g/mol to about 750,000 g/mol, or from about 200,000 g/mol to about 750,000 g/mol, or from about 250,000 g/mol to about 750,000 g/mol, or from about 300,000 g/mol to about 750,000 g/mol, or from about 350,000 g/mol to about 750,000 g/mol, or from about 400,000 g/mol to about 750,000 g/mol, or from about 450,000 g/mol to about 750,000 g/mol, or from about 500,000 g/mol to about 750,000 g/mol, or from about 550,000 g/mol to about 750,000 g/mol, or from about 600,000 g/mol to about 750,000 g/mol, or from about 650,000 g/mol to about 750,000 g/mol, or from about 700,000 g/mol to about 750,000 g/mol, or from about 50,000 g/mol to about 700,000 g/mol, or from about 100,000 g/mol to about 700,000 g/mol, or from about 150,000 g/mol to about 700,000 g/mol, or from about 200,000 g/mol to about 700,000 g/mol, or from about 250,000 g/mol to about 700,000 g/mol, or from about 300,000 g/mol to about 700,000 g/mol, or from about 350,000 g/mol to about 700,000 g/mol, or from about 400,000 g/mol to about 700,000 g/mol, or from about 450,000 g/mol to about 700,000 g/mol, or from about 500,000 g/mol to about 700,000 g/mol, or from about 550,000 g/mol to about 700,000 g/mol, or from about 600,000 g/mol to about 700,000 g/mol, or from about 650,000 g/mol to about 700,000 g/mol, or from about 50,000 g/mol to about 650,000 g/mol, or from about 100,000 g/mol to about 650,000 g/mol, or from about 150,000 g/mol to about 650,000 g/mol, or from about 200,000 g/mol to about 650,000 g/mol, or from about 250,000 g/mol to about 650,000 g/mol, or from about 300,000 g/mol to about 650,000 g/mol, or from about 350,000 g/mol to about 650,000 g/mol, or from about 400,000 g/mol to about 650,000 g/mol, or from about 450,000 g/mol to about 650,000 g/mol, or from about 500,000 g/mol to about 650,000 g/mol, or from about 550,000 g/mol to about 650,000 g/mol, or from about 600,000 g/mol to about 650,000 g/mol, or from about 50,000 g/mol to about 600,000 g/mol, or from about 100,000 g/mol to about 600,000 g/mol, or from about 150,000 g/mol to about 600,000 g/mol, or from about 200,000 g/mol to about 600,000 g/mol, or from about 250,000 g/mol to about 600,000 g/mol, or from about 300,000 g/mol to about 600,000 g/mol, or from about 350,000 g/mol to about 600,000 g/mol, or from about 400,000 g/mol to about 600,000 g/mol, or from about 450,000 g/mol to about 600,000 g/mol, or from about 500,000 g/mol to about 600,000 g/mol, or from about 550,000 g/mol to about 600,000 g/mol, or from about 50,000 g/mol to about 550,000 g/mol, or from about 100,000 g/mol to about 550,000 g/mol, or from about 150,000 g/mol to about 550,000 g/mol, or from about 200,000 g/mol to about 550,000 g/mol, or from about 250,000 g/mol to about 550,000 g/mol, or from about 300,000 g/mol to about 550,000 g/mol, or from about 350,000 g/mol to about 550,000 g/mol, or from about 400,000 g/mol to about 550,000 g/mol, or from about 450,000 g/mol to about 550,000 g/mol, or from about 500,000 g/mol to about 550,000 g/mol, or from about 50,000 g/mol to about 550,000 g/mol, or from about 100,000 g/mol to about 550,000 g/mol, or from about 150,000 g/mol to about 550,000 g/mol, or from about 200,000 g/mol to about 550,000 g/mol, or from about 250,000 g/mol to about 550,000 g/mol, or from about 300,000 g/mol to about 550,000 g/mol, or from about 350,000 g/mol to about 550,000 g/mol, or from about 400,000 g/mol to about 550,000 g/mol, or from about 450,000 g/mol to about 550,000 g/mol, or from about 500,000 g/mol to about 550,000 g/mol, or from about 50,000 g/mol to about 500,000 g/mol, or from about 100,000 g/mol to about 500,000 g/mol, or from about 150,000 g/mol to about 500,000 g/mol, or from about 200,000 g/mol to about 500,000 g/mol, or from about 250,000 g/mol to about 500,000 g/mol, or from about 300,000 g/mol to about 500,000 g/mol, or from about 350,000 g/mol to about 500,000 g/mol, or from about 400,000 g/mol to about 500,000 g/mol, or from about 450,000 g/mol to about 500,000 g/mol, or from about 50,000 g/mol to about 450,000 g/mol, or from about 100,000 g/mol to about 450,000 g/mol, or from about 150,000 g/mol to about 450,000 g/mol, or from about 200,000 g/mol to about 450,000 g/mol, or from about 250,000 g/mol to about 450,000 g/mol, or from about 300,000 g/mol to about 450,000 g/mol, or from about 350,000 g/mol to about 450,000 g/mol, or from about 400,000 g/mol to about 450,000 g/mol, or from about 50,000 g/mol to about 400,000 g/mol, or from about 100,000 g/mol to about 400,000 g/mol, or from about 150,000 g/mol to about 400,000 g/mol, or from about 200,000 g/mol to about 400,000 g/mol; or from about 250,000 g/mol to about 400,000 g/mol, or from about 300,000 g/mol to about 400,000 g/mol, or from about 350,000 g/mol to about 400,000 g/mol, or from about 50,000 g/mol to about 350,000 g/mol, or from about 100,000 g/mol to about 350,000 g/mol, or from about 150,000 g/mol to about 350,000 g/mol, or from about 200,000 g/mol to about 350,000 g/mol, or from about 250,000 g/mol to about 350,000 g/mol, or from about 300,000 g/mol to about 350,000 g/mol, or from about 50,000 g/mol to about 300,000 g/mol, or from about 100,000 g/mol to about 300,000 g/mol, or from about 150,000 g/mol to about 300,000 g/mol, or from about 200,000 g/mol to about 300,000 g/mol, or from about 250,000 g/mol to about 300,000 g/mol, or from about 50,000 g/mol to about 250,000 g/mol, or from about 100,000 g/mol to about 250,000 g/mol, or from about 150,000 g/mol to about 250,000 g/mol, or from about 200,000 g/mol to about 250,000 g/mol, or from about 50,000 g/mol to about 200,000 g/mol, or from about 100,000 g/mol to about 200,000 g/mol, or from about 150,000 g/mol to about 200,000 g/mol, or from about 50,000 g/mol to about 150,000 g/mol, or from about 100,000 g/mol to about 150,000 g/mol, or from about 50,000 g/mol to about 100,000 g/mol, or from about 90,000 g/mol to about 300,000 g/mol, or from about 100,000 g/mol to about 300,000 g/mol, or from about 110,000 g/mol to about 300,000 g/mol, or from about 120,000 g/mol to about 300,000 g/mol, or from about 130,000 g/mol to about 300,000 g/mol, or from about 140,000 g/mol to about 300,000 g/mol, or from about 150,000 g/mol to about 300,000 g/mol, or from about 160,000 g/mol to about 300,000 g/mol, or from about 170,000 g/mol to about 300,000 g/mol, or from about 180,000 g/mol to about 300,000 g/mol, or from about 190,000 g/mol to about 300,000 g/mol, or from about 200,000 g/mol to about 300,000 g/mol, or from about 210,000 g/mol to about 300,000 g/mol, or from about 220,000 g/mol to about 300,000 g/mol, or from about 230,000 g/mol to about 300,000 g/mol, or from about 240,000 g/mol to about 300,000 g/mol, or from about 250,000 g/mol to about 300,000 g/mol, or from about 260,000 g/mol to about 300,000 g/mol, or from about 270,000 g/mol to about 300,000 g/mol, or from about 280,000 g/mol to about 300,000 g/mol, or from about 290,000 g/mol to about 300,000 g/mol, or from about 90,000 g/mol to about 290,000 g/mol, or from about 100,000 g/mol to about 290,000 g/mol, or from about 110,000 g/mol to about 290,000 g/mol, or from about 120,000 g/mol to about 290,000 g/mol, or from about 130,000 g/mol to about 290,000 g/mol, or from about 140,000 g/mol to about 290,000 g/mol, or from about 150,000 g/mol to about 290,000 g/mol, or from about 160,000 g/mol to about 290,000 g/mol, or from about 170,000 g/mol to about 290,000 g/mol, or from about 180,000 g/mol to about 290,000 g/mol, or from about 190,000 g/mol to about 290,000 g/mol, or from about 200,000 g/mol to about 290,000 g/mol, or from about 210,000 g/mol to about 290,000 g/mol, or from about 220,000 g/mol to about 290,000 g/mol, or from about 230,000 g/mol to about 290,000 g/mol, or from about 240,000 g/mol to about 290,000 g/mol, or from about 250,000 g/mol to about 290,000 g/mol, or from about 260,000 g/mol to about 290,000 g/mol, or from about 270,000 g/mol to about 290,000 g/mol, or from about 280,000 g/mol to about 290,000 g/mol, or from about 90,000 g/mol to about 280,000 g/mol, or from about 100,000 g/mol to about 280,000 g/mol, or from about 110,000 g/mol to about 280,000 g/mol, or from about 120,000 g/mol to about 280,000 g/mol, or from about 130,000 g/mol to about 280,000 g/mol, or from about 140,000 g/mol to about 280,000 g/mol, or from about 150,000 g/mol to about 280,000 g/mol, or from about 160,000 g/mol to about 280,000 g/mol, or from about 170,000 g/mol to about 280,000 g/mol, or from about 180,000 g/mol to about 280,000 g/mol, or from about 190,000 g/mol to about 280,000 g/mol, or from about 200,000 g/mol to about 280,000 g/mol, or from about 210,000 g/mol to about 280,000 g/mol, or from about 220,000 g/mol to about 280,000 g/mol, or from about 230,000 g/mol to about 280,000 g/mol, or from about 240,000 g/mol to about 280,000 g/mol, or from about 250,000 g/mol to about 280,000 g/mol, or from about 260,000 g/mol to about 280,000 g/mol, or from about 270,000 g/mol to about 280,000 g/mol, or from about 90,000 g/mol to about 270,000 g/mol, or from about 100,000 g/mol to about 270,000 g/mol, or from about 110,000 g/mol to about 270,000 g/mol, or from about 120,000 g/mol to about 270,000 g/mol, or from about 130,000 g/mol to about 270,000 g/mol, or from about 140,000 g/mol to about 270,000 g/mol, or from about 150,000 g/mol to about 270,000 g/mol, or from about 160,000 g/mol to about 270,000 g/mol, or from about 170,000 g/mol to about 270,000 g/mol, or from about 180,000 g/mol to about 270,000 g/mol, or from about 190,000 g/mol to about 270,000 g/mol, or from about 200,000 g/mol to about 270,000 g/mol, or from about 210,000 g/mol to about 270,000 g/mol, or from about 220,000 g/mol to about 270,000 g/mol, or from about 230,000 g/mol to about 270,000 g/mol, or from about 240,000 g/mol to about 270,000 g/mol, or from about 250,000 g/mol to about 270,000 g/mol, or from about 260,000 g/mol to about 270,000 g/mol, or from about 90,000 g/mol to about 260,000 g/mol, or from about 100,000 g/mol to about 260,000 g/mol, or from about 110,000 g/mol to about 260,000 g/mol, or from about 120,000 g/mol to about 260,000 g/mol, or from about 130,000 g/mol to about 260,000 g/mol, or from about 140,000 g/mol to about 260,000 g/mol, or from about 150,000 g/mol to about 260,000 g/mol, or from about 160,000 g/mol to about 260,000 g/mol, or from about 170,000 g/mol to about 260,000 g/mol, or from about 180,000 g/mol to about 260,000 g/mol, or from about 190,000 g/mol to about 260,000 g/mol, or from about 200,000 g/mol to about 260,000 g/mol, or from about 210,000 g/mol to about 260,000 g/mol, or from about 220,000 g/mol to about 260,000 g/mol, or from about 230,000 g/mol to about 260,000 g/mol, or from about 240,000 g/mol to about 260,000 g/mol, or from about 250,000 g/mol to about 260,000 g/mol, or from about 90,000 g/mol to about 250,000 g/mol, or from about 100,000 g/mol to about 250,000 g/mol, or from about 110,000 g/mol to about 250,000 g/mol, or from about 120,000 g/mol to about 250,000 g/mol, or from about 130,000 g/mol to about 250,000 g/mol, or from about 140,000 g/mol to about 250,000 g/mol, or from about 150,000 g/mol to about 250,000 g/mol, or from about 160,000 g/mol to about 250,000 g/mol, or from about 170,000 g/mol to about 250,000 g/mol, or from about 180,000 g/mol to about 250,000 g/mol, or from about 190,000 g/mol to about 250,000 g/mol, or from about 200,000 g/mol to about 250,000 g/mol, or from about 210,000 g/mol to about 250,000 g/mol, or from about 220,000 g/mol to about 250,000 g/mol, or from about 230,000 g/mol to about 250,000 g/mol, or from about 240,000 g/mol to about 250,000 g/mol, or from about 90,000 g/mol to about 240,000 g/mol, or from about 100,000 g/mol to about 240,000 g/mol, or from about 110,000 g/mol to about 240,000 g/mol, or from about 120,000 g/mol to about 240,000 g/mol, or from about 130,000 g/mol to about 240,000 g/mol, or from about 140,000 g/mol to about 240,000 g/mol, or from about 150,000 g/mol to about 240,000 g/mol, or from about 160,000 g/mol to about 240,000 g/mol, or from about 170,000 g/mol to about 240,000 g/mol, or from about 180,000 g/mol to about 240,000 g/mol, or from about 190,000 g/mol to about 240,000 g/mol, or from about 200,000 g/mol to about 240,000 g/mol, or from about 210,000 g/mol to about 240,000 g/mol, or from about 220,000 g/mol to about 240,000 g/mol, or from about 230,000 g/mol to about 240,000 g/mol, or from about 90,000 g/mol to about 230,000 g/mol, or from about 100,000 g/mol to about 230,000 g/mol, or from about 110,000 g/mol to about 230,000 g/mol, or from about 120,000 g/mol to about 230,000 g/mol, or from about 130,000 g/mol to about 230,000 g/mol, or from about 140,000 g/mol to about 230,000 g/mol, or from about 150,000 g/mol to about 230,000 g/mol, or from about 160,000 g/mol to about 230,000 g/mol, or from about 170,000 g/mol to about 230,000 g/mol, or from about 180,000 g/mol to about 230,000 g/mol, or from about 190,000 g/mol to about 230,000 g/mol, or from about 200,000 g/mol to about 230,000 g/mol, or from about 210,000 g/mol to about 230,000 g/mol, or from about 220,000 g/mol to about 230,000 g/mol, or from about 90,000 g/mol to about 220,000 g/mol, or from about 100,000 g/mol to about 220,000 g/mol, or from about 110,000 g/mol to about 220,000 g/mol, or from about 120,000 g/mol to about 220,000 g/mol, or from about 130,000 g/mol to about 220,000 g/mol, or from about 140,000 g/mol to about 220,000 g/mol, or from about 150,000 g/mol to about 220,000 g/mol, or from about 160,000 g/mol to about 220,000 g/mol, or from about 170,000 g/mol to about 220,000 g/mol, or from about 180,000 g/mol to about 220,000 g/mol, or from about 190,000 g/mol to about 220,000 g/mol, or from about 200,000 g/mol to about 220,000 g/mol, or from about 210,000 g/mol to about 220,000 g/mol, or from about 90,000 g/mol to about 210,000 g/mol, or from about 100,000 g/mol to about 210,000 g/mol, or from about 110,000 g/mol to about 210,000 g/mol, or from about 120,000 g/mol to about 210,000 g/mol, or from about 130,000 g/mol to about 210,000 g/mol, or from about 140,000 g/mol to about 210,000 g/mol, or from about 150,000 g/mol to about 210,000 g/mol, or from about 160,000 g/mol to about 210,000 g/mol, or from about 170,000 g/mol to about 210,000 g/mol, or from about 180,000 g/mol to about 210,000 g/mol, or from about 190,000 g/mol to about 210,000 g/mol, or from about 200,000 g/mol to about 210,000 g/mol, or from about 90,000 g/mol to about 200,000 g/mol, or from about 100,000 g/mol to about 200,000 g/mol, or from about 110,000 g/mol to about 200,000 g/mol, or from about 120,000 g/mol to about 200,000 g/mol, or from about 130,000 g/mol to about 200,000 g/mol, or from about 140,000 g/mol to about 200,000 g/mol, or from about 150,000 g/mol to about 200,000 g/mol, or from about 160,000 g/mol to about 200,000 g/mol, or from about 170,000 g/mol to about 200,000 g/mol, or from about 180,000 g/mol to about 200,000 g/mol, or from about 190,000 g/mol to about 200,000 g/mol, or from about 90,000 g/mol to about 190,000 g/mol, or from about 100,000 g/mol to about 190,000 g/mol, or from about 110,000 g/mol to about 190,000 g/mol, or from about 120,000 g/mol to about 190,000 g/mol, or from about 130,000 g/mol to about 190,000 g/mol, or from about 140,000 g/mol to about 190,000 g/mol, or from about 150,000 g/mol to about 190,000 g/mol, or from about 160,000 g/mol to about 190,000 g/mol, or from about 170,000 g/mol to about 190,000 g/mol, or from about 180,000 g/mol to about 190,000 g/mol, or from about 90,000 g/mol to about 180,000 g/mol, or from about 100,000 g/mol to about 180,000 g/mol, or from about 110,000 g/mol to about 180,000 g/mol, or from about 120,000 g/mol to about 180,000 g/mol, or from about 130,000 g/mol to about 180,000 g/mol, or from about 140,000 g/mol to about 180,000 g/mol, or from about 150,000 g/mol to about 180,000 g/mol, or from about 160,000 g/mol to about 180,000 g/mol, or from about 170,000 g/mol to about 180,000 g/mol, or from about 90,000 g/mol to about 170,000 g/mol, or from about 100,000 g/mol to about 170,000 g/mol, or from about 110,000 g/mol to about 170,000 g/mol, or from about 120,000 g/mol to about 170,000 g/mol, or from about 130,000 g/mol to about 170,000 g/mol, or from about 140,000 g/mol to about 170,000 g/mol, or from about 150,000 g/mol to about 170,000 g/mol, or from about 160,000 g/mol to about 170,000 g/mol, or from about 90,000 g/mol to about 160,000 g/mol, or from about 100,000 g/mol to about 160,000 g/mol, or from about 110,000 g/mol to about 160,000 g/mol, or from about 120,000 g/mol to about 160,000 g/mol, or from about 130,000 g/mol to about 160,000 g/mol, or from about 140,000 g/mol to about 160,000 g/mol, or from about 150,000 g/mol to about 160,000 g/mol, or from about 90,000 g/mol to about 150,000 g/mol, or from about 100,000 g/mol to about 150,000 g/mol, or from about 110,000 g/mol to about 150,000 g/mol, or from about 120,000 g/mol to about 150,000 g/mol, or from about 130,000 g/mol to about 150,000 g/mol, or from about 140,000 g/mol to about 150,000 g/mol, or from about 90,000 g/mol to about 140,000 g/mol, or from about 100,000 g/mol to about 140,000 g/mol, or from about 110,000 g/mol to about 140,000 g/mol, or from about 120,000 g/mol to about 140,000 g/mol, or from about 130,000 g/mol to about 140,000 g/mol, or from about 90,000 g/mol to about 130,000 g/mol, or from about 100,000 g/mol to about 130,000 g/mol, or from about 110,000 g/mol to about 130,000 g/mol, or from about 120,000 g/mol to about 130,000 g/mol, or from about 90,000 g/mol to about 120,000 g/mol, or from about 100,000 g/mol to about 120,000 g/mol, or from about 110,000 g/mol to about 120,000 g/mol, or from about 90,000 g/mol to about 110,000 g/mol, or from about 100,000 g/mol to about 110,000 g/mol, or from about 90,000 g/mol to about 100,000 g/mol.

In an embodiment, at least one of the switching segments may comprise, for example, cross-linking. In an embodiment, at least one of the switching segments may comprise, for example, physical cross-linking. In an embodiment, at least one of the switching segments may comprise, for example, cross-linking in the absence of chemical cross-linking. In an embodiment, the switching segment may comprise, for example, cross-linking in an amount from about 0.1 wt % to about 30 wt %, or from about 0.5 wt % to about 30 wt %, or from about 0.75 wt % to about 30 wt %, or from about 1 wt % to about 30 wt %, or from about 2 wt % to about 30 wt %, or from about 4 wt % to about 30 wt %, or from about 6 wt % to about 30 wt %, or from about 8 wt % to about 30 wt %, or from about 10 wt % to about 30 wt %, or from about 12 wt % to about 30 wt %, or from about 14 wt % to about 30 wt %, or from about 16 wt % to about 30 wt %, or from about 18 wt % to about 30 wt %, or from about 20 wt % to about 30 wt %, or from about 22 wt % to about 30 wt %, or from about 24 wt % to about 30 wt %, or from about 26 wt % to about 30 wt %, or from about 28 wt % to about 30 wt %, or from about 0.1 wt % to about 28 wt %, or from about 0.5 wt % to about 28 wt %, or from about 0.75 wt % to about 28 wt %, or from about 1 wt % to about 28 wt %, or from about 2 wt % to about 28 wt %, or from about 4 wt % to about 28 wt %, or from about 6 wt % to about 28 wt %, or from about 8 wt % to about 28 wt %, or from about 10 wt % to about 28 wt %, or from about 12 wt % to about 28 wt %, or from about 14 wt % to about 28 wt %, or from about 16 wt % to about 28 wt %, or from about 18 wt % to about 28 wt %, or from about 20 wt % to about 28 wt %, or from about 22 wt % to about 28 wt %, or from about 24 wt % to about 28 wt %, or from about 26 wt % to about 28 wt %, or from about 0.1 wt % to about 26 wt %, or from about 0.5 wt % to about 26 wt %, or from about 0.75 wt % to about 26 wt %, or from about 1 wt % to about 26 wt %, or from about 2 wt % to about 26 wt %, or from about 4 wt % to about 26 wt %, or from about 6 wt % to about 26 wt %, or from about 8 wt % to about 26 wt %, or from about 10 wt % to about 26 wt %, or from about 12 wt % to about 26 wt %, or from about 14 wt % to about 26 wt %, or from about 16 wt % to about 26 wt %, or from about 18 wt % to about 26 wt %, or from about 20 wt % to about 26 wt %, or from about 22 wt % to about 26 wt %, or from about 24 wt % to about 26 wt %, or from about 0.1 wt % to about 24 wt %, or from about 0.5 wt % to about 24 wt %, or from about 0.75 wt % to about 24 wt %, or from about 1 wt % to about 24 wt %, or from about 2 wt % to about 24 wt %, or from about 4 wt % to about 24 wt %, or from about 6 wt % to about 24 wt %, or from about 8 wt % to about 24 wt %, or from about 10 wt % to about 24 wt %, or from about 12 wt % to about 24 wt %, or from about 14 wt % to about 24 wt %, or from about 16 wt % to about 24 wt %, or from about 18 wt % to about 24 wt %, or from about 20 wt % to about 24 wt %, or from about 22 wt % to about 24 wt %, or from about 0.1 wt % to about 22 wt %, or from about 0.5 wt % to about 22 wt %, or from about 0.75 wt % to about 22 wt %, or from about 1 wt % to about 22 wt %, or from about 2 wt % to about 22 wt %, or from about 4 wt % to about 22 wt %, or from about 6 wt % to about 22 wt %, or from about 8 wt % to about 22 wt %, or from about 10 wt % to about 22 wt %, or from about 12 wt % to about 22 wt %, or from about 14 wt % to about 22 wt %, or from about 16 wt % to about 22 wt %, or from about 18 wt % to about 22 wt %, or from about 20 wt % to about 22 wt %, or from about 0.1 wt % to about 20 wt %, or from about 0.5 wt % to about 20 wt %, or from about 0.75 wt % to about 20 wt %, or from about 1 wt % to about 20 wt %, or from about 2 wt % to about 20 wt %, or from about 4 wt % to about 20 wt %, or from about 6 wt % to about 20 wt %, or from about 8 wt % to about 20 wt %, or from about 10 wt % to about 20 wt %, or from about 12 wt % to about 20 wt %, or from about 14 wt % to about 20 wt %, or from about 16 wt % to about 20 wt %, or from about 18 wt % to about 20 wt %, or from about 0.1 wt % to about 18 wt %, or from about 0.5 wt % to about 18 wt %, or from about 0.75 wt % to about 18 wt %, or from about 1 wt % to about 18 wt %, or from about 2 wt % to about 18 wt %, or from about 4 wt % to about 18 wt %, or from about 6 wt % to about 18 wt %, or from about 8 wt % to about 18 wt %, or from about 10 wt % to about 18 wt %, or from about 12 wt % to about 18 wt %, or from about 14 wt % to about 18 wt %, or from about 16 wt % to about 18 wt %, or from about 0.1 wt % to about 16 wt %, or from about 0.5 wt % to about 16 wt %, or from about 0.75 wt % to about 16 wt %, or from about 1 wt % to about 16 wt %, or from about 2 wt % to about 16 wt %, or from about 4 wt % to about 16 wt %, or from about 6 wt % to about 16 wt %, or from about 8 wt % to about 16 wt %, or from about 10 wt % to about 16 wt %, or from about 12 wt % to about 16 wt %, or from about 14 wt % to about 16 wt %, or from about 0.1 wt % to about 14 wt %, or from about 0.5 wt % to about 14 wt %, or from about 0.75 wt % to about 14 wt %, or from about 1 wt % to about 14 wt %, or from about 2 wt % to about 14 wt %, or from about 4 wt % to about 14 wt %, or from about 6 wt % to about 14 wt %, or from about 8 wt % to about 14 wt %, or from about 10 wt % to about 14 wt %, or from about 12 wt % to about 14 wt %, or from about 0.1 wt % to about 12 wt %, or from about 0.5 wt % to about 12 wt %, or from about 0.75 wt % to about 12 wt %, or from about 1 wt % to about 12 wt %, or from about 2 wt % to about 12 wt %, or from about 4 wt % to about 12 wt %, or from about 6 wt % to about 12 wt %, or from about 8 wt % to about 12 wt %, or from about 10 wt % to about 12 wt %, or from about 0.1 wt % to about 10 wt %, or from about 0.5 wt % to about 10 wt %, or from about 0.75 wt % to about 10 wt %, or from about 1 wt % to about 10 wt %, or from about 2 wt % to about 10 wt %, or from about 4 wt % to about 10 wt %, or from about 6 wt % to about 10 wt %, or from about 8 wt % to about 10 wt %, or from about 0.1 wt % to about 8 wt %, or from about 0.5 wt % to about 8 wt %, or from about 0.75 wt % to about 8 wt %, or from about 1 wt % to about 8 wt %, or from about 2 wt % to about 8 wt %, or from about 4 wt % to about 8 wt %, or from about 6 wt % to about 8 wt %, or from about 0.1 wt % to about 6 wt %, or from about 0.5 wt % to about 6 wt %, or from about 0.75 wt % to about 6 wt %, or from about 1 wt % to about 6 wt %, or from about 2 wt % to about 6 wt %, or from about 4 wt % to about 6 wt %, or from about 0.1 wt % to about 4 wt %, or from about 0.5 wt % to about 4 wt %, or from about 0.75 wt % to about 4 wt %, or from about 1 wt % to about 4 wt %, or from about 2 wt % to about 4 wt %, or from about 0.1 wt % to about 2 wt %, or from about 0.5 wt % to about 2 wt %, or from about 0.75 wt % to about 2 wt %, or from about 1 wt % to about 2 wt %, or from about 0.1 wt % to about 1 wt %, or from about 0.5 wt % to about 1 wt %, or from about 0.75 wt % to about 1 wt %, or from about 0.1 wt % to about 0.75 wt %, or from about 0.5 wt % to about 0.75 wt %, or from about 0.1 wt % to about 0.5 wt %. In an embodiment, the copolymer may comprise, for example, cross-linking. In an embodiment, the copolymer may comprise, for example, physical cross-linking. In an embodiment, the copolymer may comprise, for example, cross-linking in the absence of chemical cross-linking. In an embodiment, the copolymer may comprise, for example, cross-linking in an amount from about 0.1 wt % to about 30 wt %, or from about 0.5 wt % to about 30 wt %, or from about 0.75 wt % to about 30 wt %, or from about 1 wt % to about 30 wt %, or from about 2 wt % to about 30 wt %, or from about 4 wt % to about 30 wt %, or from about 6 wt % to about 30 wt %, or from about 8 wt % to about 30 wt %, or from about 10 wt % to about 30 wt %, or from about 12 wt % to about 30 wt %, or from about 14 wt % to about 30 wt %, or from about 16 wt % to about 30 wt %, or from about 18 wt % to about 30 wt %, or from about 20 wt % to about 30 wt %, or from about 22 wt % to about 30 wt %, or from about 24 wt % to about 30 wt %, or from about 26 wt % to about 30 wt %, or from about 28 wt % to about 30 wt %, or from about 0.1 wt % to about 28 wt %, or from about 0.5 wt % to about 28 wt %, or from about 0.75 wt % to about 28 wt %, or from about 1 wt % to about 28 wt %, or from about 2 wt % to about 28 wt %, or from about 4 wt % to about 28 wt %, or from about 6 wt % to about 28 wt %, or from about 8 wt % to about 28 wt %, or from about 10 wt % to about 28 wt %, or from about 12 wt % to about 28 wt %, or from about 14 wt % to about 28 wt %, or from about 16 wt % to about 28 wt %, or from about 18 wt % to about 28 wt %, or from about 20 wt % to about 28 wt %, or from about 22 wt % to about 28 wt %, or from about 24 wt % to about 28 wt %, or from about 26 wt % to about 28 wt %, or from about 0.1 wt % to about 26 wt %, or from about 0.5 wt % to about 26 wt %, or from about 0.75 wt % to about 26 wt %, or from about 1 wt % to about 26 wt %, or from about 2 wt % to about 26 wt %, or from about 4 wt % to about 26 wt %, or from about 6 wt % to about 26 wt %, or from about 8 wt % to about 26 wt %, or from about 10 wt % to about 26 wt %, or from about 12 wt % to about 26 wt %, or from about 14 wt % to about 26 wt %, or from about 16 wt % to about 26 wt %, or from about 18 wt % to about 26 wt %, or from about 20 wt % to about 26 wt %, or from about 22 wt % to about 26 wt %, or from about 24 wt % to about 26 wt %, or from about 0.1 wt % to about 24 wt %, or from about 0.5 wt % to about 24 wt %, or from about 0.75 wt % to about 24 wt %, or from about 1 wt % to about 24 wt %, or from about 2 wt % to about 24 wt %, or from about 4 wt % to about 24 wt %, or from about 6 wt % to about 24 wt %, or from about 8 wt % to about 24 wt %, or from about 10 wt % to about 24 wt %, or from about 12 wt % to about 24 wt %, or from about 14 wt % to about 24 wt %, or from about 16 wt % to about 24 wt %, or from about 18 wt % to about 24 wt %, or from about 20 wt % to about 24 wt %, or from about 22 wt % to about 24 wt %, or from about 0.1 wt % to about 22 wt %, or from about 0.5 wt % to about 22 wt %, or from about 0.75 wt % to about 22 wt %, or from about 1 wt % to about 22 wt %, or from about 2 wt % to about 22 wt %, or from about 4 wt % to about 22 wt %, or from about 6 wt % to about 22 wt %, or from about 8 wt % to about 22 wt %, or from about 10 wt % to about 22 wt %, or from about 12 wt % to about 22 wt %, or from about 14 wt % to about 22 wt %, or from about 16 wt % to about 22 wt %, or from about 18 wt % to about 22 wt %, or from about 20 wt % to about 22 wt %, or from about 0.1 wt % to about 20 wt %, or from about 0.5 wt % to about 20 wt %, or from about 0.75 wt % to about 20 wt %, or from about 1 wt % to about 20 wt %, or from about 2 wt % to about 20 wt %, or from about 4 wt % to about 20 wt %, or from about 6 wt % to about 20 wt %, or from about 8 wt % to about 20 wt %, or from about 10 wt % to about 20 wt %, or from about 12 wt % to about 20 wt %, or from about 14 wt % to about 20 wt %, or from about 16 wt % to about 20 wt %, or from about 18 wt % to about 20 wt %, or from about 0.1 wt % to about 18 wt %, or from about 0.5 wt % to about 18 wt %, or from about 0.75 wt % to about 18 wt %, or from about 1 wt % to about 18 wt %, or from about 2 wt % to about 18 wt %, or from about 4 wt % to about 18 wt %, or from about 6 wt % to about 18 wt %, or from about 8 wt % to about 18 wt %, or from about 10 wt % to about 18 wt %, or from about 12 wt % to about 18 wt %, or from about 14 wt % to about 18 wt %, or from about 16 wt % to about 18 wt %, or from about 0.1 wt % to about 16 wt %, or from about 0.5 wt % to about 16 wt %, or from about 0.75 wt % to about 16 wt %, or from about 1 wt % to about 16 wt %, or from about 2 wt % to about 16 wt %, or from about 4 wt % to about 16 wt %, or from about 6 wt % to about 16 wt %, or from about 8 wt % to about 16 wt %, or from about 10 wt % to about 16 wt %, or from about 12 wt % to about 16 wt %, or from about 14 wt % to about 16 wt %, or from about 0.1 wt % to about 14 wt %, or from about 0.5 wt % to about 14 wt %, or from about 0.75 wt % to about 14 wt %, or from about 1 wt % to about 14 wt %, or from about 2 wt % to about 14 wt %, or from about 4 wt % to about 14 wt %, or from about 6 wt % to about 14 wt %, or from about 8 wt % to about 14 wt %, or from about 10 wt % to about 14 wt %, or from about 12 wt % to about 14 wt %, or from about 0.1 wt % to about 12 wt %, or from about 0.5 wt % to about 12 wt %, or from about 0.75 wt % to about 12 wt %, or from about 1 wt % to about 12 wt %, or from about 2 wt % to about 12 wt %, or from about 4 wt % to about 12 wt %, or from about 6 wt % to about 12 wt %, or from about 8 wt % to about 12 wt %, or from about 10 wt % to about 12 wt %, or from about 0.1 wt % to about 10 wt %, or from about 0.5 wt % to about 10 wt %, or from about 0.75 wt % to about 10 wt %, or from about 1 wt % to about 10 wt %, or from about 2 wt % to about 10 wt %, or from about 4 wt % to about 10 wt %, or from about 6 wt % to about 10 wt %, or from about 8 wt % to about 10 wt %, or from about 0.1 wt % to about 8 wt %, or from about 0.5 wt % to about 8 wt %, or from about 0.75 wt % to about 8 wt %, or from about 1 wt % to about 8 wt %, or from about 2 wt % to about 8 wt %, or from about 4 wt % to about 8 wt %, or from about 6 wt % to about 8 wt %, or from about 0.1 wt % to about 6 wt %, or from about 0.5 wt % to about 6 wt %, or from about 0.75 wt % to about 6 wt %, or from about 1 wt % to about 6 wt %, or from about 2 wt % to about 6 wt %, or from about 4 wt % to about 6 wt %, or from about 0.1 wt % to about 4 wt %, or from about 0.5 wt % to about 4 wt %, or from about 0.75 wt % to about 4 wt %, or from about 1 wt % to about 4 wt %, or from about 2 wt % to about 4 wt %, or from about 0.1 wt % to about 2 wt %, or from about 0.5 wt % to about 2 wt %, or from about 0.75 wt % to about 2 wt %, or from about 1 wt % to about 2 wt %, or from about 0.1 wt % to about 1 wt %, or from about 0.5 wt % to about 1 wt %, or from about 0.75 wt % to about 1 wt %, or from about 0.1 wt % to about 0.75 wt %, or from about 0.5 wt % to about 0.75 wt %, or from about 0.1 wt % to about 0.5 wt %.

In an embodiment, the copolymer may have solution processability. As used herein, the phrase "solution processability" is used as it is normally understood to a person of skill in the art and often refers to the ability of a copolymer to dissolve in a solvent, leading to the formation of a homogeneous solution. In an embodiment, the copolymer may be, for example, soluble in a solvent. In an embodiment, the solvent may be, for example, an organic solvent. In an embodiment, the solvent may be, for example, a polar solvent. In an embodiment, the solvent may be, for example, chloroform, tetrahydrofuran, N,N-dimethylformamide, 1,4-dioxane or any combination thereof. In an embodiment, the solvent may be, for example, chloroform. In an embodiment, the solvent may be, for example, tetrahydrofuran. In an embodiment, the solvent may be, for example, N,N-dimethylformamide. In an embodiment, the solvent may be, for example, 1,4-dioxane.

In an embodiment, the copolymer may have, for example, a response time. As used herein, the phrase "response time" is used as it is normally understood to a person of skill in the art and often refers to the time for the copolymer to transform back to the first shape from the second shape after application of the second stimulus. In an embodiment, the copolymer may have, for example, a short response time. In an embodiment, the copolymer may have, for example, a response time of less than about 10 s. In an embodiment, the copolymer may have, for example, a response time of less than about 2 s. In an embodiment, the copolymer may have, for example, a response time of from about 0.1 s to about 10 s, or from about 0.2 s to about 10 s, or from about 0.3 s to about 10 s, or from about 0.4 s to about 10 s, or from about 0.5 s to about 10 s, or from about 0.6 s to about 10 s, or from about 0.7 s to about 10 s, or from about 0.8 s to about 10 s, or from about 0.9 s to about 10 s, or from about 1.0 s to about 10 s, or from about 1.1 s to about 10 s, or from about 1.2 s to about 10 s, or from about 1.3 s to about 10 s, or from about 1.4 s to about 10 s, or from about 1.5 s to about 10 s, or from about 1.6 s to about 10 s, or from about 1.7 s to about 10 s, or from about 1.8 s to about 10 s, or from about 1.9 s to about 10 s, or from about 2.0 s to about 10 s, or from about 2.1 s to about 10 s, or from about 2.2 s to about 10 s, or from about 2.3 s to about 10 s, or from about 2.4 s to about 10 s, or from about 2.5 s to about 10 s, or from about 2.6 s to about 10 s, or from about 2.7 s to about 10 s, or from about 2.8 s to about 10 s, or from about 2.9 s to about 10 s, or from about 3.0 s to about 10 s, or from about 3.1 s to about 10 s, or from about 3.2 s to about 10 s, or from about 3.3 s to about 10 s, or from about 3.4 s to about 10 s, or from about 3.4 s to about 10 s, or from about 3.5 s to about 10 s, or from about 3.6 s to about 10 s, or from about 3.7 s to about 10 s, or from about 3.8 s to about 10 s, or from about 3.9 s to about 10 s, or from about 4.0 s to about 10 s, or from about 4.1 s to about 10 s, or from about 4.2 s to about 10 s, or from about 4.3 s to about 10 s, or from about 4.4 s to about 10 s, or from about 4.5 s to about 10 s, or from about 4.6 s to about 10 s, or from about 4.7 s to about 10 s, or from about 4.8 s to about 10 s, or from about 4.9 s to about 10 s, or from about 5.0 s to about 10 s, or from about 5.1 s to about 10 s, or from about 5.2 s to about 10 s, or from about 5.3 s to about 10 s, or from about 5.4 s to about 10 s, or from about 5.5 s to about 10 s, or from about 5.6 s to about 10 s, or from about 5.7 s to about 10 s, or from about 5.8 s to about 10 s, or from about 5.9 s to about 10 s, or from about 6.0 s to about 10 s, or from about 6.1 s to about 10 s, or from about 6.2 s to about 10 s, or from about 6.3 s to about 10 s, or from about 6.4 s to about 10 s, or from about 6.5 s to about 10 s, or from about 6.6 s to about 10 s, or from about 6.7 s to about 10 s, or from about 6.8 s to about 10 s, or from about 6.9 s to about 10 s, or from about 7.0 s to about 10 s, or from about 7.1 s to about 10 s, or from about 7.2 s to about 10 s, or from about 7.3 s to about 10 s, or from about 7.4 s to about 10 s, or from about 7.5 s to about 10 s, or from about 7.6 s to about 10 s, or from about 7.7 s to about 10 s, or from about 7.8 s to about 10 s, or from about 7.9 s to about 10 s, or from about 8.0 s to about 10 s, or from about 8.1 s to about 10 s, or from about 8.2 s to about 10 s, or from about 8.3 s to about 10 s, or from about 8.4 s to about 10 s, or from about 8.5 s to about 10 s, or from about 8.6 s to about 10 s, or from about 8.7 s to about 10 s, or from about 8.8 s to about 10 s, or from about 8.9 s to about 10 s, or from about 9.0 s to about 10 s, or from about 9.1 s to about 10 s, or from about 9.2 s to about 10 s, or from about 9.3 s to about 10 s, or from about 9.4 s to about 10 s, or from about 9.5 s to about 10 s, or from about 9.6 s to about 10 s, or from about 9.7 s to about 10 s, or from about 9.8 s to about 10 s, or from about 9.9 s to about 10 s, or from about 0.1 s to about 9.9 s, or from about 0.2 s to about 9.9 s, or from about 0.3 s to about 9.9 s, or from about 0.4 s to about 9.9 s, or from about 0.5 s to about 9.9 s, or from about 0.6 s to about 9.9 s, or from about 0.7 s to about 9.9 s, or from about 0.8 s to about 9.9 s, or from about 0.9 s to about 9.9 s, or from about 1.0 s to about 9.9 s, or from about 1.1 s to about 9.9 s, or from about 1.2 s to about 9.9 s, or from about 1.3 s to about 9.9 s, or from about 1.4 s to about 9.9 s, or from about 1.5 s to about 9.9 s, or from about 1.6 s to about 9.9 s, or from about 1.7 s to about 9.9 s, or from about 1.8 s to about 9.9 s, or from about 1.9 s to about 9.9 s, or from about 2.0 s to about 9.9 s, or from about 2.1 s to about 9.9 s, or from about 2.2 s to about 9.9 s, or from about 2.3 s to about 9.9 s, or from about 2.4 s to about 9.9 s, or from about 2.5 s to about 9.9 s, or from about 2.6 s to about 9.9 s, or from about 2.7 s to about 9.9 s, or from about 2.8 s to about 9.9 s, or from about 2.9 s to about 9.9 s, or from about 3.0 s to about 9.9 s, or from about 3.1 s to about 9.9 s, or from about 3.2 s to about 9.9 s, or from about 3.3 s to about 9.9 s, or from about 3.4 s to about 9.9 s, or from about 3.4 s to about 9.9 s, or from about 3.5 s to about 9.9 s, or from about 3.6 s to about 9.9 s, or from about 3.7 s to about 9.9 s, or from about 3.8 s to about 9.9 s, or from about 3.9 s to about 9.9 s, or from about 4.0 s to about 9.9 s, or from about 4.1 s to about 9.9 s, or from about 4.2 s to about 9.9 s, or from about 4.3 s to about 9.9 s, or from about 4.4 s to about 9.9 s, or from about 4.5 s to about 9.9 s, or from about 4.6 s to about 9.9 s, or from about 4.7 s to about 9.9 s, or from about 4.8 s to about 9.9 s, or from about 4.9 s to about 9.9 s, or from about 5.0 s to about 9.9 s, or from about 5.1 s to about 9.9 s, or from about 5.2 s to about 9.9 s, or from about 5.3 s to about 9.9 s, or from about 5.4 s to about 9.9 s, or from about 5.5 s to about 9.9 s, or from about 5.6 s to about 9.9 s, or from about 5.7 s to about 9.9 s, or from about 5.8 s to about 9.9 s, or from about 5.9 s to about 9.9 s, or from about 6.0 s to about 9.9 s, or from about 6.1 s to about 9.9 s, or from about 6.2 s to about 9.9 s, or from about 6.3 s to about 9.9 s, or from about 6.4 s to about 9.9 s, or from about 6.5 s to about 9.9 s, or from about 6.6 s to about 9.9 s, or from about 6.7 s to about 9.9 s, or from about 6.8 s to about 9.9 s, or from about 6.9 s to about 9.9 s, or from about 7.0 s to about 9.9 s, or from about 7.1 s to about 9.9 s, or from about 7.2 s to about 9.9 s, or from about 7.3 s to about 9.9 s, or from about 7.4 s to about 9.9 s, or from about 7.5 s to about 9.9 s, or from about 7.6 s to about 9.9 s, or from about 7.7 s to about 9.9 s, or from about 7.8 s to about 9.9 s, or from about 7.9 s to about 9.9 s, or from about 8.0 s to about 9.9 s, or from about 8.1 s to about 9.9 s, or from about 8.2 s to about 9.9 s, or from about 8.3 s to about 9.9 s, or from about 8.4 s to about 9.9 s, or from about 8.5 s to about 9.9 s, or from about 8.6 s to about 9.9 s, or from about 8.7 s to about 9.9 s, or from about 8.8 s to about 9.9 s, or from about 8.9 s to about 9.9 s, or from about 9.0 s to about 9.9 s, or from about 9.1 s to about 9.9 s, or from about 9.2 s to about 9.9 s, or from about 9.3 s to about 9.9 s, or from about 9.4 s to about 9.9 s, or from about 9.5 s to about 9.9 s, or from about 9.6 s to about 9.9 s, or from about 9.7 s to about 9.9 s, or from about 9.8 s to about 9.9 s, or from about 0.1 s to about 9.8 s, or from about 0.2 s to about 9.8 s, or from about 0.3 s to about 9.8 s, or from about 0.4 s to about 9.8 s, or from about 0.5 s to about 9.8 s, or from about 0.6 s to about 9.8 s, or from about 0.7 s to about 9.8 s, or from about 0.8 s to about 9.8 s, or from about 0.9 s to about 9.8 s, or from about 1.0 s to about 9.8 s, or from about 1.1 s to about 9.8 s, or from about 1.2 s to about 9.8 s, or from about 1.3 s to about 9.8 s, or from about 1.4 s to about 9.8 s, or from about 1.5 s to about 9.8 s, or from about 1.6 s to about 9.8 s, or from about 1.7 s to about 9.8 s, or from about 1.8 s to about 9.8 s, or from about 1.9 s to about 9.8 s, or from about 2.0 s to about 9.8 s, or from about 2.1 s to about 9.8 s, or from about 2.2 s to about 9.8 s, or from about 2.3 s to about 9.8 s, or from about 2.4 s to about 9.8 s, or from about 2.5 s to about 9.8 s, or from about 2.6 s to about 9.8 s, or from about 2.7 s to about 9.8 s, or from about 2.8 s to about 9.8 s, or from about 2.9 s to about 9.8 s, or from about 3.0 s to about 9.8 s, or from about 3.1 s to about 9.8 s, or from about 3.2 s to about 9.8 s, or from about 3.3 s to about 9.8 s, or from about 3.4 s to about 9.8 s, or from about 3.4 s to about 9.8 s, or from about 3.5 s to about 9.8 s, or from about 3.6 s to about 9.8 s, or from about 3.7 s to about 9.8 s, or from about 3.8 s to about 9.8 s, or from about 3.9 s to about 9.8 s, or from about 4.0 s to about 9.8 s, or from about 4.1 s to about 9.8 s, or from about 4.2 s to about 9.8 s, or from about 4.3 s to about 9.8 s, or from about 4.4 s to about 9.8 s, or from about 4.5 s to about 9.8 s, or from about 4.6 s to about 9.8 s, or from about 4.7 s to about 9.8 s, or from about 4.8 s to about 9.8 s, or from about 4.9 s to about 9.8 s, or from about 5.0 s to about 9.8 s, or from about 5.1 s to about 9.8 s, or from about 5.2 s to about 9.8 s, or from about 5.3 s to about 9.8 s, or from about 5.4 s to about 9.8 s, or from about 5.5 s to about 9.8 s, or from about 5.6 s to about 9.8 s, or from about 5.7 s to about 9.8 s, or from about 5.8 s to about 9.8 s, or from about 5.9 s to about 9.8 s, or from about 6.0 s to about 9.8 s, or from about 6.1 s to about 9.8 s, or from about 6.2 s to about 9.8 s, or from about 6.3 s to about 9.8 s, or from about 6.4 s to about 9.8 s, or from about 6.5 s to about 9.8 s, or from about 6.6 s to about 9.8 s, or from about 6.7 s to about 9.8 s, or from about 6.8 s to about 9.8 s, or from about 6.9 s to about 9.8 s, or from about 7.0 s to about 9.8 s, or from about 7.1 s to about 9.8 s, or from about 7.2 s to about 9.8 s, or from about 7.3 s to about 9.8 s, or from about 7.4 s to about 9.8 s, or from about 7.5 s to about 9.8 s, or from about 7.6 s to about 9.8 s, or from about 7.7 s to about 9.8 s, or from about 7.8 s to about 9.8 s, or from about 7.9 s to about 9.8 s, or from about 8.0 s to about 9.8 s, or from about 8.1 s to about 9.8 s, or from about 8.2 s to about 9.8 s, or from about 8.3 s to about 9.8 s, or from about 8.4 s to about 9.8 s, or from about 8.5 s to about 9.8 s, or from about 8.6 s to about 9.8 s, or from about 8.7 s to about 9.8 s, or from about 8.8 s to about 9.8 s, or from about 8.9 s to about 9.8 s, or from about 9.0 s to about 9.8 s, or from about 9.1 s to about 9.8 s, or from about 9.2 s to about 9.8 s, or from about 9.3 s to about 9.8 s, or from about 9.4 s to about 9.8 s, or from about 9.5 s to about 9.8 s, or from about 9.6 s to about 9.8 s, or from about 9.7 s to about 9.8 s, or from about 0.1 s to about 9.7 s, or from about 0.2 s to about 9.7 s, or from about 0.3 s to about 9.7 s, or from about 0.4 s to about 9.7 s, or from about 0.5 s to about 9.7 s, or from about 0.6 s to about 9.7 s, or from about 0.7 s to about 9.7 s, or from about 0.8 s to about 9.7 s, or from about 0.9 s to about 9.7 s, or from about 1.0 s to about 9.7 s, or from about 1.1 s to about 9.7 s, or from about 1.2 s to about 9.7 s, or from about 1.3 s to about 9.7 s, or from about 1.4 s to about 9.7 s, or from about 1.5 s to about 9.7 s, or from about 1.6 s to about 9.7 s, or from about 1.7 s to about 9.7 s, or from about 1.8 s to about 9.7 s, or from about 1.9 s to about 9.7 s, or from about 2.0 s to about 9.7 s, or from about 2.1 s to about 9.7 s, or from about 2.2 s to about 9.7 s, or from about 2.3 s to about 9.7 s, or from about 2.4 s to about 9.7 s, or from about 2.5 s to about 9.7 s, or from about 2.6 s to about 9.7 s, or from about 2.7 s to about 9.7 s, or from about 2.8 s to about 9.7 s, or from about 2.9 s to about 9.7 s, or from about 3.0 s to about 9.7 s, or from about 3.1 s to about 9.7 s, or from about 3.2 s to about 9.7 s, or from about 3.3 s to about 9.7 s, or from about 3.4 s to about 9.7 s, or from about 3.4 s to about 9.7 s, or from about 3.5 s to about 9.7 s, or from about 3.6 s to about 9.7 s, or from about 3.7 s to about 9.7 s, or from about 3.8 s to about 9.7 s, or from about 3.9 s to about 9.7 s, or from about 4.0 s to about 9.7 s, or from about 4.1 s to about 9.7 s, or from about 4.2 s to about 9.7 s, or from about 4.3 s to about 9.7 s, or from about 4.4 s to about 9.7 s, or from about 4.5 s to about 9.7 s, or from about 4.6 s to about 9.7 s, or from about 4.7 s to about 9.7 s, or from about 4.8 s to about 9.7 s, or from about 4.9 s to about 9.7 s, or from about 5.0 s to about 9.7 s, or from about 5.1 s to about 9.7 s, or from about 5.2 s to about 9.7 s, or from about 5.3 s to about 9.7 s, or from about 5.4 s to about 9.7 s, or from about 5.5 s to about 9.7 s, or from about 5.6 s to about 9.7 s, or from about 5.7 s to about 9.7 s, or from about 5.8 s to about 9.7 s, or from about 5.9 s to about 9.7 s, or from about 6.0 s to about 9.7 s, or from about 6.1 s to about 9.7 s, or from about 6.2 s to about 9.7 s, or from about 6.3 s to about 9.7 s, or from about 6.4 s to about 9.7 s, or from about 6.5 s to about 9.7 s, or from about 6.6 s to about 9.7 s, or from about 6.7 s to about 9.7 s, or from about 6.8 s to about 9.7 s, or from about 6.9 s to about 9.7 s, or from about 7.0 s to about 9.7 s, or from about 7.1 s to about 9.7 s, or from about 7.2 s to about 9.7 s, or from about 7.3 s to about 9.7 s, or from about 7.4 s to about 9.7 s, or from about 7.5 s to about 9.7 s, or from about 7.6 s to about 9.7 s, or from about 7.7 s to about 9.7 s, or from about 7.8 s to about 9.7 s, or from about 7.9 s to about 9.7 s, or from about 8.0 s to about 9.7 s, or from about 8.1 s to about 9.7 s, or from about 8.2 s to about 9.7 s, or from about 8.3 s to about 9.7 s, or from about 8.4 s to about 9.7 s, or from about 8.5 s to about 9.7 s, or from about 8.6 s to about 9.7 s, or from about 8.7 s to about 9.7 s, or from about 8.8 s to about 9.7 s, or from about 8.9 s to about 9.7 s, or from about 9.0 s to about 9.7 s, or from about 9.1 s to about 9.7 s, or from about 9.2 s to about 9.7 s, or from about 9.3 s to about 9.7 s, or from about 9.4 s to about 9.7 s, or from about 9.5 s to about 9.7 s, or from about 9.6 s to about 9.7 s, or from about 0.1 s to about 9.6 s, or from about 0.2 s to about 9.6 s, or from about 0.3 s to about 9.6 s, or from about 0.4 s to about 9.6 s, or from about 0.5 s to about 9.6 s, or from about 0.6 s to about 9.6 s, or from about 0.7 s to about 9.6 s, or from about 0.8 s to about 9.6 s, or from about 0.9 s to about 9.6 s, or from about 1.0 s to about 9.6 s, or from about 1.1 s to about 9.6 s, or from about 1.2 s to about 9.6 s, or from about 1.3 s to about 9.6 s, or from about 1.4 s to about 9.6 s, or from about 1.5 s to about 9.6 s, or from about 1.6 s to about 9.6 s, or from about 1.7 s to about 9.6 s, or from about 1.8 s to about 9.6 s, or from about 1.9 s to about 9.6 s, or from about 2.0 s to about 9.6 s, or from about 2.1 s to about 9.6 s, or from about 2.2 s to about 9.6 s, or from about 2.3 s to about 9.6 s, or from about 2.4 s to about 9.6 s, or from about 2.5 s to about 9.6 s, or from about 2.6 s to about 9.6 s, or from about 2.7 s to about 9.6 s, or from about 2.8 s to about 9.6 s, or from about 2.9 s to about 9.6 s, or from about 3.0 s to about 9.6 s, or from about 3.1 s to about 9.6 s, or from about 3.2 s to about 9.6 s, or from about 3.3 s to about 9.6 s, or from about 3.4 s to about 9.6 s, or from about 3.4 s to about 9.6 s, or from about 3.5 s to about 9.6 s, or from about 3.6 s to about 9.6 s, or from about 3.7 s to about 9.6 s, or from about 3.8 s to about 9.6 s, or from about 3.9 s to about 9.6 s, or from about 4.0 s to about 9.6 s, or from about 4.1 s to about 9.6 s, or from about 4.2 s to about 9.6 s, or from about 4.3 s to about 9.6 s, or from about 4.4 s to about 9.6 s, or from about 4.5 s to about 9.6 s, or from about 4.6 s to about 9.6 s, or from about 4.7 s to about 9.6 s, or from about 4.8 s to about 9.6 s, or from about 4.9 s to about 9.6 s, or from about 5.0 s to about 9.6 s, or from about 5.1 s to about 9.6 s, or from about 5.2 s to about 9.6 s, or from about 5.3 s to about 9.6 s, or from about 5.4 s to about 9.6 s, or from about 5.5 s to about 9.6 s, or from about 5.6 s to about 9.6 s, or from about 5.7 s to about 9.6 s, or from about 5.8 s to about 9.6 s, or from about 5.9 s to about 9.6 s, or from about 6.0 s to about 9.6 s, or from about 6.1 s to about 9.6 s, or from about 6.2 s to about 9.6 s, or from about 6.3 s to about 9.6 s, or from about 6.4 s to about 9.6 s, or from about 6.5 s to about 9.6 s, or from about 6.6 s to about 9.6 s, or from about 6.7 s to about 9.6 s, or from about 6.8 s to about 9.6 s, or from about 6.9 s to about 9.6 s, or from about 7.0 s to about 9.6 s, or from about 7.1 s to about 9.6 s, or from about 7.2 s to about 9.6 s, or from about 7.3 s to about 9.6 s, or from about 7.4 s to about 9.6 s, or from about 7.5 s to about 9.6 s, or from about 7.6 s to about 9.6 s, or from about 7.7 s to about 9.6 s, or from about 7.8 s to about 9.6 s, or from about 7.9 s to about 9.6 s, or from about 8.0 s to about 9.6 s, or from about 8.1 s to about 9.6 s, or from about 8.2 s to about 9.6 s, or from about 8.3 s to about 9.6 s, or from about 8.4 s to about 9.6 s, or from about 8.5 s to about 9.6 s, or from about 8.6 s to about 9.6 s, or from about 8.7 s to about 9.6 s, or from about 8.8 s to about 9.6 s, or from about 8.9 s to about 9.6 s, or from about 9.0 s to about 9.6 s, or from about 9.1 s to about 9.6 s, or from about 9.2 s to about 9.6 s, or from about 9.3 s to about 9.6 s, or from about 9.4 s to about 9.6 s, or from about 9.5 s to about 9.6 s, or from about 0.1 s to about 9.5 s, or from about 0.2 s to about 9.5 s, or from about 0.3 s to about 9.5 s, or from about 0.4 s to about 9.5 s, or from about 0.5 s to about 9.5 s, or from about 0.6 s to about 9.5 s, or from about 0.7 s to about 9.5 s, or from about 0.8 s to about 9.5 s, or from about 0.9 s to about 9.5 s, or from about 1.0 s to about 9.5 s, or from about 1.1 s to about 9.5 s, or from about 1.2 s to about 9.5 s, or from about 1.3 s to about 9.5 s, or from about 1.4 s to about 9.5 s, or from about 1.5 s to about 9.5 s, or from about 1.6 s to about 9.5 s, or from about 1.7 s to about 9.5 s, or from about 1.8 s to about 9.5 s, or from about 1.9 s to about 9.5 s, or from about 2.0 s to about 9.5 s, or from about 2.1 s to about 9.5 s, or from about 2.2 s to about 9.5 s, or from about 2.3 s to about 9.5 s, or from about 2.4 s to about 9.5 s, or from about 2.5 s to about 9.5 s, or from about 2.6 s to about 9.5 s, or from about 2.7 s to about 9.5 s, or from about 2.8 s to about 9.5 s, or from about 2.9 s to about 9.5 s, or from about 3.0 s to about 9.5 s, or from about 3.1 s to about 9.5 s, or from about 3.2 s to about 9.5 s, or from about 3.3 s to about 9.5 s, or from about 3.4 s to about 9.5 s, or from about 3.4 s to about 9.5 s, or from about 3.5 s to about 9.5 s, or from about 3.6 s to about 9.5 s, or from about 3.7 s to about 9.5 s, or from about 3.8 s to about 9.5 s, or from about 3.9 s to about 9.5 s, or from about 4.0 s to about 9.5 s, or from about 4.1 s to about 9.5 s, or from about 4.2 s to about 9.5 s, or from about 4.3 s to about 9.5 s, or from about 4.4 s to about 9.5 s, or from about 4.5 s to about 9.5 s, or from about 4.6 s to about 9.5 s, or from about 4.7 s to about 9.5 s, or from about 4.8 s to about 9.5 s, or from about 4.9 s to about 9.5 s, or from about 5.0 s to about 9.5 s, or from about 5.1 s to about 9.5 s, or from about 5.2 s to about 9.5 s, or from about 5.3 s to about 9.5 s, or from about 5.4 s to about 9.5 s, or from about 5.5 s to about 9.5 s, or from about 5.6 s to about 9.5 s, or from about 5.7 s to about 9.5 s, or from about 5.8 s to about 9.5 s, or from about 5.9 s to about 9.5 s, or from about 6.0 s to about 9.5 s, or from about 6.1 s to about 9.5 s, or from about 6.2 s to about 9.5 s, or from about 6.3 s to about 9.5 s, or from about 6.4 s to about 9.5 s, or from about 6.5 s to about 9.5 s, or from about 6.6 s to about 9.5 s, or from about 6.7 s to about 9.5 s, or from about 6.8 s to about 9.5 s, or from about 6.9 s to about 9.5 s, or from about 7.0 s to about 9.5 s, or from about 7.1 s to about 9.5 s, or from about 7.2 s to about 9.5 s, or from about 7.3 s to about 9.5 s, or from about 7.4 s to about 9.5 s, or from about 7.5 s to about 9.5 s, or from about 7.6 s to about 9.5 s, or from about 7.7 s to about 9.5 s, or from about 7.8 s to about 9.5 s, or from about 7.9 s to about 9.5 s, or from about 8.0 s to about 9.5 s, or from about 8.1 s to about 9.5 s, or from about 8.2 s to about 9.5 s, or from about 8.3 s to about 9.5 s, or from about 8.4 s to about 9.5 s, or from about 8.5 s to about 9.5 s, or from about 8.6 s to about 9.5 s, or from about 8.7 s to about 9.5 s, or from about 8.8 s to about 9.5 s, or from about 8.9 s to about 9.5 s, or from about 9.0 s to about 9.5 s, or from about 9.1 s to about 9.5 s, or from about 9.2 s to about 9.5 s, or from about 9.3 s to about 9.5 s, or from about 9.4 s to about 9.5 s, or from about 0.1 s to about 9.4 s, or from about 0.2 to about 9.4 s, or from about 0.3 s to about 9.4 s, or from about 0.4 s to about 9.4 s, or from about 0.5 s to about 9.4 s, or from about 0.6 s to about 9.4 s, or from about 0.7 s to about 9.4 s, or from about 0.8 s to about 9.4 s, or from about 0.9 s to about 9.4 s, or from about 1.0 s to about 9.4 s, or from about 1.1 s to about 9.4 s, or from about 1.2 s to about 9.4 s, or from about 1.3 s to about 9.4 s, or from about 1.4 s to about 9.4 s, or from about 1.5 s to about 9.4 s, or from about 1.6 s to about 9.4 s, or from about 1.7 s to about 9.4 s, or from about 1.8 s to about 9.4 s, or from about 1.9 s to about 9.4 s, or from about 2.0 s to about 9.4 s, or from about 2.1 s to about 9.4 s, or from about 2.2 s to about 9.4 s, or from about 2.3 s to about 9.4 s, or from about 2.4 s to about 9.4 s, or from about 2.5 s to about 9.4 s, or from about 2.6 s to about 9.4 s, or from about 2.7 s to about 9.4 s, or from about 2.8 s to about 9.4 s, or from about 2.9 s to about 9.4 s, or from about 3.0 s to about 9.4 s, or from about 3.1 s to about 9.4 s, or from about 3.2 s to about 9.4 s, or from about 3.3 s to about 9.4 s, or from about 3.4 s to about 9.4 s, or from about 3.4 s to about 9.4 s, or from about 3.5 s to about 9.4 s, or from about 3.6 s to about 9.4 s, or from about 3.7 s to about 9.4 s, or from about 3.8 s to about 9.4 s, or from about 3.9 s to about 9.4 s, or from about 4.0 s to about 9.4 s, or from about 4.1 s to about 9.4 s, or from about 4.2 s to about 9.4 s, or from about 4.3 s to about 9.4 s, or from about 4.4 s to about 9.4 s, or from about 4.5 s to about 9.4 s, or from about 4.6 s to about 9.4 s, or from about 4.7 s to about 9.4 s, or from about 4.8 s to about 9.4 s, or from about 4.9 s to about 9.4 s, or from about 5.0 s to about 9.4 s, or from about 5.1 s to about 9.4 s, or from about 5.2 s to about 9.4 s, or from about 5.3 s to about 9.4 s, or from about 5.4 s to about 9.4 s, or from about 5.5 s to about 9.4 s, or from about 5.6 s to about 9.4 s, or from about 5.7 s to about 9.4 s, or from about 5.8 s to about 9.4 s, or from about 5.9 s to about 9.4 s, or from about 6.0 s to about 9.4 s, or from about 6.1 s to about 9.4 s, or from about 6.2 s to about 9.4 s, or from about 6.3 s to about 9.4 s, or from about 6.4 s to about 9.4 s, or from about 6.5 s to about 9.4 s, or from about 6.6 s to about 9.4 s, or from about 6.7 s to about 9.4 s, or from about 6.8 s to about 9.4 s, or from about 6.9 s to about 9.4 s, or from about 7.0 s to about 9.4 s, or from about 7.1 s to about 9.4 s, or from about 7.2 s to about 9.4 s, or from about 7.3 s to about 9.4 s, or from about 7.4 s to about 9.4 s, or from about 7.5 s to about 9.4 s, or from about 7.6 s to about 9.4 s, or from about 7.7 s to about 9.4 s, or from about 7.8 s to about 9.4 s, or from about 7.9 s to about 9.4 s, or from about 8.0 s to about 9.4 s, or from about 8.1 s to about 9.4 s, or from about 8.2 s to about 9.4 s, or from about 8.3 s to about 9.4 s, or from about 8.4 s to about 9.4 s, or from about 8.5 s to about 9.4 s, or from about 8.6 s to about 9.4 s, or from about 8.7 s to about 9.4 s, or from about 8.8 s to about 9.4 s, or from about 8.9 s to about 9.4 s, or from about 9.0 s to about 9.4 s, or from about 9.1 s to about 9.4 s, or from about 9.2 s to about 9.4 s, or from about 9.3 s to about 9.4 s, or from about 0.1 s to about 9.3 s, or from about 0.2 s to about 9.3 s, or from about 0.3 s to about 9.3 s, or from about 0.4 s to about 9.3 s, or from about 0.5 s to about 9.3 s, or from about 0.6 s to about 9.3 s, or from about 0.7 s to about 9.3 s, or from about 0.8 s to about 9.3 s, or from about 0.9 s to about 9.3 s, or from about 1.0 s to about 9.3 s, or from about 1.1 s to about 9.3 s, or from about 1.2 s to about 9.3 s, or from about 1.3 s to about 9.3 s, or from about 1.4 s to about 9.3 s, or from about 1.5 s to about 9.3 s, or from about 1.6 s to about 9.3 s, or from about 1.7 s to about 9.3 s, or from about 1.8 s to about 9.3 s, or from about 1.9 s to about 9.3 s, or from about 2.0 s to about 9.3 s, or from about 2.1 s to about 9.3 s, or from about 2.2 s to about 9.3 s, or from about 2.3 s to about 9.3 s, or from about 2.4 s to about 9.3 s, or from about 2.5 s to about 9.3 s, or from about 2.6 s to about 9.3 s, or from about 2.7 s to about 9.3 s, or from about 2.8 s to about 9.3 s, or from about 2.9 s to about 9.3 s, or from about 3.0 s to about 9.3 s, or from about 3.1 s to about 9.3 s, or from about 3.2 s to about 9.3 s, or from about 3.3 s to about 9.3 s, or from about 3.4 s to about 9.3 s, or from about 3.4 s to about 9.3 s, or from about 3.5 s to about 9.3 s, or from about 3.6 s to about 9.3 s, or from about 3.7 s to about 9.3 s, or from about 3.8 s to about 9.3 s, or from about 3.9 s to about 9.3 s, or from about 4.0 s to about 9.3 s, or from about 4.1 s to about 9.3 s, or from about 4.2 s to about 9.3 s, or from about 4.3 s to about 9.3 s, or from about 4.4 s to about 9.3 s, or from about 4.5 s to about 9.3 s, or from about 4.6 s to about 9.3 s, or from about 4.7 s to about 9.3 s, or from about 4.8 s to about 9.3 s, or from about 4.9 s to about 9.3 s, or from about 5.0 s to about 9.3 s, or from about 5.1 s to about 9.3 s, or from about 5.2 s to about 9.3 s, or from about 5.3 s to about 9.3 s, or from about 5.4 s to about 9.3 s, or from about 5.5 s to about 9.3 s, or from about 5.6 s to about 9.3 s, or from about 5.7 s to about 9.3 s, or from about 5.8 s to about 9.3 s, or from about 5.9 s to about 9.3 s, or from about 6.0 s to about 9.3 s, or from about 6.1 s to about 9.3 s, or from about 6.2 s to about 9.3 s, or from about 6.3 s to about 9.3 s, or from about 6.4 s to about 9.3 s, or from about 6.5 s to about 9.3 s, or from about 6.6 s to about 9.3 s, or from about 6.7 s to about 9.3 s, or from about 6.8 s to about 9.3 s, or from about 6.9 s to about 9.3 s, or from about 7.0 s to about 9.3 s, or from about 7.1 s to about 9.3 s, or from about 7.2 s to about 9.3 s, or from about 7.3 s to about 9.3 s, or from about 7.4 s to about 9.3 s, or from about 7.5 s to about 9.3 s, or from about 7.6 s to about 9.3 s, or from about 7.7 s to about 9.3 s, or from about 7.8 s to about 9.3 s, or from about 7.9 s to about 9.3 s, or from about 8.0 s to about 9.3 s, or from about 8.1 s to about 9.3 s, or from about 8.2 s to about 9.3 s, or from about 8.3 s to about 9.3 s, or from about 8.4 s to about 9.3 s, or from about 8.5 s to about 9.3 s, or from about 8.6 s to about 9.3 s, or from about 8.7 s to about 9.3 s, or from about 8.8 s to about 9.3 s, or from about 8.9 s to about 9.3 s, or from about 9.0 s to about 9.3 s, or from about 9.1 s to about 9.3 s, or from about 9.2 s to about 9.3 s, or from about 0.1 s to about 9.2 s, or from about 0.2 s to about 9.2 s, or from about 0.3 s to about 9.2 s, or from about 0.4 s to about 9.2 s, or from about 0.5 s to about 9.2 s, or from about 0.6 s to about 9.2 s, or from about 0.7 s to about 9.2 s, or from about 0.8 s to about 9.2 s, or from about 0.9 s to about 9.2 s, or from about 1.0 s to about 9.2 s, or from about 1.1 s to about 9.2 s, or from about 1.2 s to about 9.2 s, or from about 1.3 s to about 9.2 s, or from about 1.4 s to about 9.2 s, or from about 1.5 s to about 9.2 s, or from about 1.6 s to about 9.2 s, or from about 1.7 s to about 9.2 s, or from about 1.8 s to about 9.2 s, or from about 1.9 s to about 9.2 s, or from about 2.0 s to about 9.2 s, or from about 2.1 s to about 9.2 s, or from about 2.2 s to about 9.2 s, or from about 2.3 s to about 9.2 s, or from about 2.4 s to about 9.2 s, or from about 2.5 s to about 9.2 s, or from about 2.6 s to about 9.2 s, or from about 2.7 s to about 9.2 s, or from about 2.8 s to about 9.2 s, or from about 2.9 s to about 9.2 s, or from about 3.0 s to about 9.2 s, or from about 3.1 s to about 9.2 s, or from about 3.2 s to about 9.2 s, or from about 3.3 s to about 9.2 s, or from about 3.4 s to about 9.2 s, or from about 3.4 s to about 9.2 s, or from about 3.5 s to about 9.2 s, or from about 3.6 s to about 9.2 s, or from about 3.7 s to about 9.2 s, or from about 3.8 s to about 9.2 s, or from about 3.9 s to about 9.2 s, or from about 4.0 s to about 9.2 s, or from about 4.1 s to about 9.2 s, or from about 4.2 s to about 9.2 s, or from about 4.3 s to about 9.2 s, or from about 4.4 s to about 9.2 s, or from about 4.5 s to about 9.2 s, or from about 4.6 s to about 9.2 s, or from about 4.7 s to about 9.2 s, or from about 4.8 s to about 9.2 s, or from about 4.9 s to about 9.2 s, or from about 5.0 s to about 9.2 s, or from about 5.1 s to about 9.2 s, or from about 5.2 s to about 9.2 s, or from about 5.3 s to about 9.2 s, or from about 5.4 s to about 9.2 s, or from about 5.5 s to about 9.2 s, or from about 5.6 s to about 9.2 s, or from about 5.7 s to about 9.2 s, or from about 5.8 s to about 9.2 s, or from about 5.9 s to about 9.2 s, or from about 6.0 s to about 9.2 s, or from about 6.1 s to about 9.2 s, or from about 6.2 s to about 9.2 s, or from about 6.3 s to about 9.2 s, or from about 6.4 s to about 9.2 s, or from about 6.5 s to about 9.2 s, or from about 6.6 s to about 9.2 s, or from about 6.7 s to about 9.2 s, or from about 6.8 s to about 9.2 s, or from about 6.9 s to about 9.2 s, or from about 7.0 s to about 9.2 s, or from about 7.1 s to about 9.2 s, or from about 7.2 s to about 9.2 s, or from about 7.3 s to about 9.2 s, or from about 7.4 s to about 9.2 s, or from about 7.5 s to about 9.2 s, or from about 7.6 s to about 9.2 s, or from about 7.7 s to about 9.2 s, or from about 7.8 s to about 9.2 s, or from about 7.9 s to about 9.2 s, or from about 8.0 s to about 9.2 s, or from about 8.1 s to about 9.2 s, or from about 8.2 s to about 9.2 s, or from about 8.3 s to about 9.2 s, or from about 8.4 s to about 9.2 s, or from about 8.5 s to about 9.2 s, or from about 8.6 s to about 9.2 s, or from about 8.7 s to about 9.2 s, or from about 8.8 s to about 9.2 s, or from about 8.9 s to about 9.2 s, or from about 9.0 s to about 9.2 s, or from about 9.1 s to about 9.2 s, or from about 0.1 s to about 9.1 s, or from about 0.2 s to about 9.1 s, or from about 0.3 s to about 9.1 s, or from about 0.4 s to about 9.1 s, or from about 0.5 s to about 9.1 s, or from about 0.6 s to about 9.1 s, or from about 0.7 s to about 9.1 s, or from about 0.8 s to about 9.1 s, or from about 0.9 s to about 9.1 s, or from about 1.0 s to about 9.1 s, or from about 1.1 s to about 9.1 s, or from about 1.2 s to about 9.1 s, or from about 1.3 s to about 9.1 s, or from about 1.4 s to about 9.1 s, or from about 1.5 s to about 9.1 s, or from about 1.6 s to about 9.1 s, or from about 1.7 s to about 9.1 s, or from about 1.8 s to about 9.1 s, or from about 1.9 s to about 9.1 s, or from about 2.0 s to about 9.1 s, or from about 2.1 s to about 9.1 s, or from about 2.2 s to about 9.1 s, or from about 2.3 s to about 9.1 s, or from about 2.4 s to about 9.1 s, or from about 2.5 s to about 9.1 s, or from about 2.6 s to about 9.1 s, or from about 2.7 s to about 9.1 s, or from about 2.8 s to about 9.1 s, or from about 2.9 s to about 9.1 s, or from about 3.0 s to about 9.1 s, or from about 3.1 s to about 9.1 s, or from about 3.2 s to about 9.1 s, or from about 3.3 s to about 9.1 s, or from about 3.4 s to about 9.1 s, or from about 3.4 s to about 9.1 s, or from about 3.5 s to about 9.1 s, or from about 3.6 s to about 9.1 s, or from about 3.7 s to about 9.1 s, or from about 3.8 s to about 9.1 s, or from about 3.9 s to about 9.1 s, or from about 4.0 s to about 9.1 s, or from about 4.1 s to about 9.1 s, or from about 4.2 s to about 9.1 s, or from about 4.3 s to about 9.1 s, or from about 4.4 s to about 9.1 s, or from about 4.5 s to about 9.1 s, or from about 4.6 s to about 9.1 s, or from about 4.7 s to about 9.1 s, or from about 4.8 s to about 9.1 s, or from about 4.9 s to about 9.1 s, or from about 5.0 s to about 9.1 s, or from about 5.1 s to about 9.1 s, or from about 5.2 s to about 9.1 s, or from about 5.3 s to about 9.1 s, or from about 5.4 s to about 9.1 s, or from about 5.5 s to about 9.1 s, or from about 5.6 s to about 9.1 s, or from about 5.7 s to about 9.1 s, or from about 5.8 s to about 9.1 s, or from about 5.9 s to about 9.1 s, or from about 6.0 s to about 9.1 s, or from about 6.1 s to about 9.1 s, or from about 6.2 s to about 9.1 s, or from about 6.3 s to about 9.1 s, or from about 6.4 s to about 9.1 s, or from about 6.5 s to about 9.1 s, or from about 6.6 s to about 9.1 s, or from about 6.7 s to about 9.1 s, or from about 6.8 s to about 9.1 s, or from about 6.9 s to about 9.1 s, or from about 7.0 s to about 9.1 s, or from about 7.1 s to about 9.1 s, or from about 7.2 s to about 9.1 s, or from about 7.3 s to about 9.1 s, or from about 7.4 s to about 9.1 s, or from about 7.5 s to about 9.1 s, or from about 7.6 s to about 9.1 s, or from about 7.7 s to about 9.1 s, or from about 7.8 s to about 9.1 s, or from about 7.9 s to about 9.1 s, or from about 8.0 s to about 9.1 s, or from about 8.1 s to about 9.1 s, or from about 8.2 s to about 9.1 s, or from about 8.3 s to about 9.1 s, or from about 8.4 s to about 9.1 s, or from about 8.5 s to about 9.1 s, or from about 8.6 s to about 9.1 s, or from about 8.7 s to about 9.1 s, or from about 8.8 s to about 9.1 s, or from about 8.9 s to about 9.1 s, or from about 9.0 s to about 9.1 s, or from about 0.1 s to about 9.0 s, or from about 0.2 s to about 9.0 s, or from about 0.3 s to about 9.0 s, or from about 0.4 s to about 9.0 s, or from about 0.5 s to about 9.0 s, or from about 0.6 s to about 9.0 s, or from about 0.7 s to about 9.0 s, or from about 0.8 s to about 9.0 s, or from about 0.9 s to about 9.0 s, or from about 1.0 s to about 9.0 s, or from about 1.1 s to about 9.0 s, or from about 1.2 s to about 9.0 s, or from about 1.3 s to about 9.0 s, or from about 1.4 s to about 9.0 s, or from about 1.5 s to about 9.0 s, or from about 1.6 s to about 9.0 s, or from about 1.7 s to about 9.0 s, or from about 1.8 s to about 9.0 s, or from about 1.9 s to about 9.0 s, or from about 2.0 s to about 9.0 s, or from about 2.1 s to about 9.0 s, or from about 2.2 s to about 9.0 s, or from about 2.3 s to about 9.0 s, or from about 2.4 s to about 9.0 s, or from about 2.5 s to about 9.0 s, or from about 2.6 s to about 9.0 s, or from about 2.7 s to about 9.0 s, or from about 2.8 s to about 9.0 s, or from about 2.9 s to about 9.0 s, or from about 3.0 s to about 9.0 s, or from about 3.1 s to about 9.0 s, or from about 3.2 s to about 9.0 s, or from about 3.3 s to about 9.0 s, or from about 3.4 s to about 9.0 s, or from about 3.4 s to about 9.0 s, or from about 3.5 s to about 9.0 s, or from about 3.6 s to about 9.0 s, or from about 3.7 s to about 9.0 s, or from about 3.8 s to about 9.0 s, or from about 3.9 s to about 9.0 s, or from about 4.0 s to about 9.0 s, or from about 4.1 s to about 9.0 s, or from about 4.2 s to about 9.0 s, or from about 4.3 s to about 9.0 s, or from about 4.4 s to about 9.0 s, or from about 4.5 s to about 9.0 s, or from about 4.6 s to about 9.0 s, or from about 4.7 s to about 9.0 s, or from about 4.8 s to about 9.0 s, or from about 4.9 s to about 9.0 s, or from about 5.0 s to about 9.0 s, or from about 5.1 s to about 9.0 s, or from about 5.2 s to about 9.0 s, or from about 5.3 s to about 9.0 s, or from about 5.4 s to about 9.0 s, or from about 5.5 s to about 9.0 s, or from about 5.6 s to about 9.0 s, or from about 5.7 s to about 9.0 s, or from about 5.8 s to about 9.0 s, or from about 5.9 s to about 9.0 s, or from about 6.0 s to about 9.0 s, or from about 6.1 s to about 9.0 s, or from about 6.2 s to about 9.0 s, or from about 6.3 s to about 9.0 s, or from about 6.4 s to about 9.0 s, or from about 6.5 s to about 9.0 s, or from about 6.6 s to about 9.0 s, or from about 6.7 s to about 9.0 s, or from about 6.8 s to about 9.0 s, or from about 6.9 s to about 9.0 s, or from about 7.0 s to about 9.0 s, or from about 7.1 s to about 9.0 s, or from about 7.2 s to about 9.0 s, or from about 7.3 s to about 9.0 s, or from about 7.4 s to about 9.0 s, or from about 7.5 s to about 9.0 s, or from about 7.6 s to about 9.0 s, or from about 7.7 s to about 9.0 s, or from about 7.8 s to about 9.0 s, or from about 7.9 s to about 9.0 s, or from about 8.0 s to about 9.0 s, or from about 8.1 s to about 9.0 s, or from about 8.2 s to about 9.0 s, or from about 8.3 s to about 9.0 s, or from about 8.4 s to about 9.0 s, or from about 8.5 s to about 9.0 s, or from about 8.6 s to about 9.0 s, or from about 8.7 s to about 9.0 s, or from about 8.8 s to about 9.0 s, or from about 8.9 s to about 9.0 s, or from about 0.1 s to about 8.9 s, or from about 0.2 s to about 8.9 s, or from about 0.3 s to about 8.9 s, or from about 0.4 s to about 8.9 s, or from about 0.5 s to about 8.9 s, or from about 0.6 s to about 8.9 s, or from about 0.7 s to about 8.9 s, or from about 0.8 s to about 8.9 s, or from about 0.9 s to about 8.9 s, or from about 1.0 s to about 8.9 s, or from about 1.1 s to about 8.9 s, or from about 1.2 s to about 8.9 s, or from about 1.3 s to about 8.9 s, or from about 1.4 s to about 8.9 s, or from about 1.5 s to about 8.9 s, or from about 1.6 s to about 8.9 s, or from about 1.7 s to about 8.9 s, or from about 1.8 s to about 8.9 s, or from about 1.9 s to about 8.9 s, or from about 2.0 s to about 8.9 s, or from about 2.1 s to about 8.9 s, or from about 2.2 s to about 8.9 s, or from about 2.3 s to about 8.9 s, or from about 2.4 s to about 8.9 s, or from about 2.5 s to about 8.9 s, or from about 2.6 s to about 8.9 s, or from about 2.7 s to about 8.9 s, or from about 2.8 s to about 8.9 s, or from about 2.9 s to about 8.9 s, or from about 3.0 s to about 8.9 s, or from about 3.1 s to about 8.9 s, or from about 3.2 s to about 8.9 s, or from about 3.3 s to about 8.9 s, or from about 3.4 s to about 8.9 s, or from about 3.4 s to about 8.9 s, or from about 3.5 s to about 8.9 s, or from about 3.6 s to about 8.9 s, or from about 3.7 s to about 8.9 s, or from about 3.8 s to about 8.9 s, or from about 3.9 s to about 8.9 s, or from about 4.0 s to about 8.9 s, or from about 4.1 s to about 8.9 s, or from about 4.2 s to about 8.9 s, or from about 4.3 s to about 8.9 s, or from about 4.4 s to about 8.9 s, or from about 4.5 s to about 8.9 s, or from about 4.6 s to about 8.9 s, or from about 4.7 s to about 8.9 s, or from about 4.8 s to about 8.9 s, or from about 4.9 s to about 8.9 s, or from about 5.0 s to about 8.9 s, or from about 5.1 s to about 8.9 s, or from about 5.2 s to about 8.9 s, or from about 5.3 s to about 8.9 s, or from about 5.4 s to about 8.9 s, or from about 5.5 s to about 8.9 s, or from about 5.6 s to about 8.9 s, or from about 5.7 s to about 8.9 s, or from about 5.8 s to about 8.9 s, or from about 5.9 s to about 8.9 s, or from about 6.0 s to about 8.9 s, or from about 6.1 s to about 8.9 s, or from about 6.2 s to about 8.9 s, or from about 6.3 s to about 8.9 s, or from about 6.4 s to about 8.9 s, or from about 6.5 s to about 8.9 s, or from about 6.6 s to about 8.9 s, or from about 6.7 s to about 8.9 s, or from about 6.8 s to about 8.9 s, or from about 6.9 s to about 8.9 s, or from about 7.0 s to about 8.9 s, or from about 7.1 s to about 8.9 s, or from about 7.2 s to about 8.9 s, or from about 7.3 s to about 8.9 s, or from about 7.4 s to about 8.9 s, or from about 7.5 s to about 8.9 s, or from about 7.6 s to about 8.9 s, or from about 7.7 s to about 8.9 s, or from about 7.8 s to about 8.9 s, or from about 7.9 s to about 8.9 s, or from about 8.0 s to about 8.9 s, or from about 8.1 s to about 8.9 s, or from about 8.2 s to about 8.9 s, or from about 8.3 s to about 8.9 s, or from about 8.4 s to about 8.9 s, or from about 8.5 s to about 8.9 s, or from about 8.6 s to about 8.9 s, or from about 8.7 s to about 8.9 s, or from about 8.8 s to about 8.9 s, or from about 0.1 s to about 8.8 s, or from about 0.2 s to about 8.8 s, or from about 0.3 s to about 8.8 s, or from about 0.4 s to about 8.8 s, or from about 0.5 s to about 8.8 s, or from about 0.6 s to about 8.8 s, or from about 0.7 s to about 8.8 s, or from about 0.8 s to about 8.8 s, or from about 0.9 s to about 8.8 s, or from about 1.0 s to about 8.8 s, or from about 1.1 s to about 8.8 s, or from about 1.2 s to about 8.8 s, or from about 1.3 s to about 8.8 s, or from about 1.4 s to about 8.8 s, or from about 1.5 s to about 8.8 s, or from about 1.6 s to about 8.8 s, or from about 1.7 s to about 8.8 s, or from about 1.8 s to about 8.8 s, or from about 1.9 s to about 8.8 s, or from about 2.0 s to about 8.8 s, or from about 2.1 s to about 8.8 s, or from about 2.2 s to about 8.8 s, or from about 2.3 s to about 8.8 s, or from about 2.4 s to about 8.8 s, or from about 2.5 s to about 8.8 s, or from about 2.6 s to about 8.8 s, or from about 2.7 s to about 8.8 s, or from about 2.8 s to about 8.8 s, or from about 2.9 s to about 8.8 s, or from about 3.0 s to about 8.8 s, or from about 3.1 s to about 8.8 s, or from about 3.2 s to about 8.8 s, or from about 3.3 s to about 8.8 s, or from about 3.4 s to about 8.8 s, or from about 3.4 s to about 8.8 s, or from about 3.5 s to about 8.8 s, or from about 3.6 s to about 8.8 s, or from about 3.7 s to about 8.8 s, or from about 3.8 s to about 8.8 s, or from about 3.9 s to about 8.8 s, or from about 4.0 s to about 8.8 s, or from about 4.1 s to about 8.8 s, or from about 4.2 s to about 8.8 s, or from about 4.3 s to about 8.8 s, or from about 4.4 s to about 8.8 s, or from about 4.5 s to about 8.8 s, or from about 4.6 s to about 8.8 s, or from about 4.7 s to about 8.8 s, or from about 4.8 s to about 8.8 s, or from about 4.9 s to about 8.8 s, or from about 5.0 s to about 8.8 s, or from about 5.1 s to about 8.8 s, or from about 5.2 s to about 8.8 s, or from about 5.3 s to about 8.8 s, or from about 5.4 s to about 8.8 s, or from about 5.5 s to about 8.8 s, or from about 5.6 s to about 8.8 s, or from about 5.7 s to about 8.8 s, or from about 5.8 s to about 8.8 s, or from about 5.9 s to about 8.8 s, or from about 6.0 s to about 8.8 s, or from about 6.1 s to about 8.8 s, or from about 6.2 s to about 8.8 s, or from about 6.3 s to about 8.8 s, or from about 6.4 s to about 8.8 s, or from about 6.5 s to about 8.8 s, or from about 6.6 s to about 8.8 s, or from about 6.7 s to about 8.8 s, or from about 6.8 s to about 8.8 s, or from about 6.9 s to about 8.8 s, or from about 7.0 s to about 8.8 s, or from about 7.1 s to about 8.8 s, or from about 7.2 s to about 8.8 s, or from about 7.3 s to about 8.8 s, or from about 7.4 s to about 8.8 s, or from about 7.5 s to about 8.8 s, or from about 7.6 s to about 8.8 s, or from about 7.7 s to about 8.8 s, or from about 7.8 s to about 8.8 s, or from about 7.9 s to about 8.8 s, or from about 8.0 s to about 8.8 s, or from about 8.1 s to about 8.8 s, or from about 8.2 s to about 8.8 s, or from about 8.3 s to about 8.8 s, or from about 8.4 s to about 8.8 s, or from about 8.5 s to about 8.8 s, or from about 8.6 s to about 8.8 s, or from about 8.7 s to about 8.8 s, or from about 0.1 to about 8.7 s, or from about 0.2 s to about 8.7 s, or from about 0.3 s to about 8.7 s, or from about 0.4 s to about 8.7 s, or from about 0.5 s to about 8.7 s, or from about 0.6 s to about 8.7 s, or from about 0.7 s to about 8.7 s, or from about 0.8 s to about 8.7 s, or from about 0.9 s to about 8.7 s, or from about 1.0 s to about 8.7 s, or from about 1.1 s to about 8.7 s, or from about 1.2 s to about 8.7 s, or from about 1.3 s to about 8.7 s, or from about 1.4 s to about 8.7 s, or from about 1.5 s to about 8.7 s, or from about 1.6 s to about 8.7 s, or from about 1.7 s to about 8.7 s, or from about 1.8 s to about 8.7 s, or from about 1.9 s to about 8.7 s, or from about 2.0 s to about 8.7 s, or from about 2.1 s to about 8.7 s, or from about 2.2 s to about 8.7 s, or from about 2.3 s to about 8.7 s, or from about 2.4 s to about 8.7 s, or from about 2.5 s to about 8.7 s, or from about 2.6 s to about 8.7 s, or from about 2.7 s to about 8.7 s, or from about 2.8 s to about 8.7 s, or from about 2.9 s to about 8.7 s, or from about 3.0 s to about 8.7 s, or from about 3.1 s to about 8.7 s, or from about 3.2 s to about 8.7 s, or from about 3.3 s to about 8.7 s, or from about 3.4 s to about 8.7 s, or from about 3.4 s to about 8.7 s, or from about 3.5 s to about 8.7 s, or from about 3.6 s to about 8.7 s, or from about 3.7 s to about 8.7 s, or from about 3.8 s to about 8.7 s, or from about 3.9 s to about 8.7 s, or from about 4.0 s to about 8.7 s, or from about 4.1 s to about 8.7 s, or from about 4.2 s to about 8.7 s, or from about 4.3 s to about 8.7 s, or from about 4.4 s to about 8.7 s, or from about 4.5 s to about 8.7 s, or from about 4.6 s to about 8.7 s, or from about 4.7 s to about 8.7 s, or from about 4.8 s to about 8.7 s, or from about 4.9 s to about 8.7 s, or from about 5.0 s to about 8.7 s, or from about 5.1 s to about 8.7 s, or from about 5.2 s to about 8.7 s, or from about 5.3 s to about 8.7 s, or from about 5.4 s to about 8.7 s, or from about 5.5 s to about 8.7 s, or from about 5.6 s to about 8.7 s, or from about 5.7 s to about 8.7 s, or from about 5.8 s to about 8.7 s, or from about 5.9 s to about 8.7 s, or from about 6.0 to about 8.7 s, or from about 6.1 s to about 8.7 s, or from about 6.2 s to about 8.7 s, or from about 6.3 s to about 8.7 s, or from about 6.4 s to about 8.7 s, or from about 6.5 s to about 8.7 s, or from about 6.6 s to about 8.7 s, or from about 6.7 s to about 8.7 s, or from about 6.8 s to about 8.7 s, or from about 6.9 s to about 8.7 s, or from about 7.0 s to about 8.7 s, or from about 7.1 s to about 8.7 s, or from about 7.2 s to about 8.7 s, or from about 7.3 s to about 8.7 s, or from about 7.4 s to about 8.7 s, or from about 7.5 s to about 8.7 s, or from about 7.6 s to about 8.7 s, or from about 7.7 s to about 8.7 s, or from about 7.8 s to about 8.7 s, or from about 7.9 s to about 8.7 s, or from about 8.0 s to about 8.7 s, or from about 8.1 s to about 8.7 s, or from about 8.2 s to about 8.7 s, or from about 8.3 s to about 8.7 s, or from about 8.4 s to about 8.7 s, or from about 8.5 s to about 8.7 s, or from about 8.6 s to about 8.7 s, or from about 0.1 s to about 8.6 s, or from about 0.2 s to about 8.6 s, or from about 0.3 s to about 8.6 s, or from about 0.4 s to about 8.6 s, or from about 0.5 s to about 8.6 s, or from about 0.6 s to about 8.6 s, or from about 0.7 s to about 8.6 s, or from about 0.8 s to about 8.6 s, or from about 0.9 s to about 8.6 s, or from about 1.0 s to about 8.6 s, or from about 1.1 s to about 8.6 s, or from about 1.2 s to about 8.6 s, or from about 1.3 s to about 8.6 s, or from about 1.4 s to about 8.6 s, or from about 1.5 s to about 8.6 s, or from about 1.6 s to about 8.6 s, or from about 1.7 s to about 8.6 s, or from about 1.8 s to about 8.6 s, or from about 1.9 s to about 8.6 s, or from about 2.0 s to about 8.6 s, or from about 2.1 s to about 8.6 s, or from about 2.2 s to about 8.6 s, or from about 2.3 s to about 8.6 s, or from about 2.4 s to about 8.6 s, or from about 2.5 s to about 8.6 s, or from about 2.6 s to about 8.6 s, or from about 2.7 s to about 8.6 s, or from about 2.8 s to about 8.6 s, or from about 2.9 s to about 8.6 s, or from about 3.0 s to about 8.6 s, or from about 3.1 s to about 8.6 s, or from about 3.2 s to about 8.6 s, or from about 3.3 s to about 8.6 s, or from about 3.4 s to about 8.6 s, or from about 3.4 s to about 8.6 s, or from about 3.5 s to about 8.6 s, or from about 3.6 s to about 8.6 s, or from about 3.7 s to about 8.6 s, or from about 3.8 s to about 8.6 s, or from about 3.9 s to about 8.6 s, or from about 4.0 s to about 8.6 s, or from about 4.1 s to about 8.6 s, or from about 4.2 s to about 8.6 s, or from about 4.3 s to about 8.6 s, or from about 4.4 s to about 8.6 s, or from about 4.5 s to about 8.6 s, or from about 4.6 s to about 8.6 s, or from about 4.7 s to about 8.6 s, or from about 4.8 s to about 8.6 s, or from about 4.9 s to about 8.6 s, or from about 5.0 s to about 8.6 s, or from about 5.1 s to about 8.6 s, or from about 5.2 s to about 8.6 s, or from about 5.3 s to about 8.6 s, or from about 5.4 s to about 8.6 s, or from about 5.5 s to about 8.6 s, or from about 5.6 s to about 8.6 s, or from about 5.7 s to about 8.6 s, or from about 5.8 s to about 8.6 s, or from about 5.9 s to about 8.6 s, or from about 6.0 s to about 8.6 s, or from about 6.1 s to about 8.6 s, or from about 6.2 s to about 8.6 s, or from about 6.3 s to about 8.6 s, or from about 6.4 s to about 8.6 s, or from about 6.5 s to about 8.6 s, or from about 6.6 s to about 8.6 s, or from about 6.7 s to about 8.6 s, or from about 6.8 s to about 8.6 s, or from about 6.9 s to about 8.6 s, or from about 7.0 s to about 8.6 s, or from about 7.1 s to about 8.6 s, or from about 7.2 s to about 8.6 s, or from about 7.3 s to about 8.6 s, or from about 7.4 s to about 8.6 s, or from about 7.5 s to about 8.6 s, or from about 7.6 s to about 8.6 s, or from about 7.7 s to about 8.6 s, or from about 7.8 s to about 8.6 s, or from about 7.9 s to about 8.6 s, or from about 8.0 s to about 8.6 s, or from about 8.1 s to about 8.6 s, or from about 8.2 s to about 8.6 s, or from about 8.3 s to about 8.6 s, or from about 8.4 s to about 8.6 s, or from about 8.5 s to about 8.6 s, or from about 0.1 s to about 8.5 s, or from about 0.2 s to about 8.5 s, or from about 0.3 s to about 8.5 s, or from about 0.4 s to about 8.5 s, or from about 0.5 s to about 8.5 s, or from about 0.6 s to about 8.5 s, or from about 0.7 s to about 8.5 s, or from about 0.8 s to about 8.5 s, or from about 0.9 s to about 8.5 s, or from about 1.0 s to about 8.5 s, or from about 1.1 s to about 8.5 s, or from about 1.2 s to about 8.5 s, or from about 1.3 s to about 8.5 s, or from about 1.4 s to about 8.5 s, or from about 1.5 s to about 8.5 s, or from about 1.6 s to about 8.5 s, or from about 1.7 s to about 8.5 s, or from about 1.8 s to about 8.5 s, or from about 1.9 s to about 8.5 s, or from about 2.0 s to about 8.5 s, or from about 2.1 s to about 8.5 s, or from about 2.2 s to about 8.5 s, or from about 2.3 s to about 8.5 s, or from about 2.4 s to about 8.5 s, or from about 2.5 s to about 8.5 s, or from about 2.6 s to about 8.5 s, or from about 2.7 s to about 8.5 s, or from about 2.8 s to about 8.5 s, or from about 2.9 s to about 8.5 s, or from about 3.0 s to about 8.5 s, or from about 3.1 s to about 8.5 s, or from about 3.2 s to about 8.5 s, or from about 3.3 s to about 8.5 s, or from about 3.4 s to about 8.5 s, or from about 3.4 s to about 8.5 s, or from about 3.5 s to about 8.5 s, or from about 3.6 s to about 8.5 s, or from about 3.7 s to about 8.5 s, or from about 3.8 s to about 8.5 s, or from about 3.9 s to about 8.5 s, or from about 4.0 s to about 8.5 s, or from about 4.1 s to about 8.5 s, or from about 4.2 s to about 8.5 s, or from about 4.3 s to about 8.5 s, or from about 4.4 s to about 8.5 s, or from about 4.5 s to about 8.5 s, or from about 4.6 s to about 8.5 s, or from about 4.7 s to about 8.5 s, or from about 4.8 s to about 8.5 s, or from about 4.9 s to about 8.5 s, or from about 5.0 s to about 8.5 s, or from about 5.1 s to about 8.5 s, or from about 5.2 s to about 8.5 s, or from about 5.3 s to about 8.5 s, or from about 5.4 s to about 8.5 s, or from about 5.5 s to about 8.5 s, or from about 5.6 s to about 8.5 s, or from about 5.7 s to about 8.5 s, or from about 5.8 s to about 8.5 s, or from about 5.9 s to about 8.5 s, or from about 6.0 s to about 8.5 s, or from about 6.1 s to about 8.5 s, or from about 6.2 s to about 8.5 s, or from about 6.3 s to about 8.5 s, or from about 6.4 s to about 8.5 s, or from about 6.5 s to about 8.5 s, or from about 6.6 s to about 8.5 s, or from about 6.7 s to about 8.5 s, or from about 6.8 s to about 8.5 s, or from about 6.9 s to about 8.5 s, or from about 7.0 s to about 8.5 s, or from about 7.1 s to about 8.5 s, or from about 7.2 s to about 8.5 s, or from about 7.3 s to about 8.5 s, or from about 7.4 s to about 8.5 s, or from about 7.5 s to about 8.5 s, or from about 7.6 s to about 8.5 s, or from about 7.7 s to about 8.5 s, or from about 7.8 s to about 8.5 s, or from about 7.9 s to about 8.5 s, or from about 8.0 s to about 8.5 s, or from about 8.1 s to about 8.5 s, or from about 8.2 s to about 8.5 s, or from about 8.3 s to about 8.5 s, or from about 8.4 s to about 8.5 s, or from about 0.1 s to about 8.4 s, or from about 0.2 s to about 8.4 s, or from about 0.3 s to about 8.4 s, or from about 0.4 s to about 8.4 s, or from about 0.5 s to about 8.4 s, or from about 0.6 s to about 8.4 s, or from about 0.7 s to about 8.4 s, or from about 0.8 s to about 8.4 s, or from about 0.9 s to about 8.4 s, or from about 1.0 s to about 8.4 s, or from about 1.1 s to about 8.4 s, or from about 1.2 s to about 8.4 s, or from about 1.3 s to about 8.4 s, or from about 1.4 s to about 8.4 s, or from about 1.5 s to about 8.4 s, or from about 1.6 s to about 8.4 s, or from about 1.7 s to about 8.4 s, or from about 1.8 s to about 8.4 s, or from about 1.9 s to about 8.4 s, or from about 2.0 s to about 8.4 s, or from about 2.1 s to about 8.4 s, or from about 2.2 s to about 8.4 s, or from about 2.3 s to about 8.4 s, or from about 2.4 s to about 8.4 s, or from about 2.5 s to about 8.4 s, or from about 2.6 s to about 8.4 s, or from about 2.7 s to about 8.4 s, or from about 2.8 s to about 8.4 s, or from about 2.9 s to about 8.4 s, or from about 3.0 s to about 8.4 s, or from about 3.1 s to about 8.4 s, or from about 3.2 s to about 8.4 s, or from about 3.3 s to about 8.4 s, or from about 3.4 s to about 8.4 s, or from about 3.4 s to about 8.4 s, or from about 3.5 s to about 8.4 s, or from about 3.6 s to about 8.4 s, or from about 3.7 s to about 8.4 s, or from about 3.8 s to about 8.4 s, or from about 3.9 s to about 8.4 s, or from about 4.0 s to about 8.4 s, or from about 4.1 s to about 8.4 s, or from about 4.2 s to about 8.4 s, or from about 4.3 s to about 8.4 s, or from about 4.4 s to about 8.4 s, or from about 4.5 s to about 8.4 s, or from about 4.6 s to about 8.4 s, or from about 4.7 s to about 8.4 s, or from about 4.8 s to about 8.4 s, or from about 4.9 s to about 8.4 s, or from about 5.0 s to about 8.4 s, or from about 5.1 s to about 8.4 s, or from about 5.2 s to about 8.4 s, or from about 5.3 s to about 8.4 s, or from about 5.4 s to about 8.4 s, or from about 5.5 s to about 8.4 s, or from about 5.6 s to about 8.4 s, or from about 5.7 s to about 8.4 s, or from about 5.8 s to about 8.4 s, or from about 5.9 s to about 8.4 s, or from about 6.0 s to about 8.4 s, or from about 6.1 s to about 8.4 s, or from about 6.2 s to about 8.4 s, or from about 6.3 s to about 8.4 s, or from about 6.4 s to about 8.4 s, or from about 6.5 s to about 8.4 s, or from about 6.6 s to about 8.4 s, or from about 6.7 s to about 8.4 s, or from about 6.8 s to about 8.4 s, or from about 6.9 s to about 8.4 s, or from about 7.0 s to about 8.4 s, or from about 7.1 s to about 8.4 s, or from about 7.2 s to about 8.4 s, or from about 7.3 s to about 8.4 s, or from about 7.4 s to about 8.4 s, or from about 7.5 s to about 8.4 s, or from about 7.6 s to about 8.4 s, or from about 7.7 s to about 8.4 s, or from about 7.8 s to about 8.4 s, or from about 7.9 s to about 8.4 s, or from about 8.0 s to about 8.4 s, or from about 8.1 s to about 8.4 s, or from about 8.2 s to about 8.4 s, or from about 8.3 s to about 8.4 s, or from about 0.1 s to about 8.3 s, or from about 0.2 s to about 8.3 s, or from about 0.3 s to about 8.3 s, or from about 0.4 s to about 8.3 s, or from about 0.5 s to about 8.3 s, or from about 0.6 s to about 8.3 s, or from about 0.7 s to about 8.3 s, or from about 0.8 s to about 8.3 s, or from about 0.9 s to about 8.3 s, or from about 1.0 s to about 8.3 s, or from about 1.1 s to about 8.3 s, or from about 1.2 s to about 8.3 s, or from about 1.3 s to about 8.3 s, or from about 1.4 s to about 8.3 s, or from about 1.5 s to about 8.3 s, or from about 1.6 s to about 8.3 s, or from about 1.7 s to about 8.3 s, or from about 1.8 s to about 8.3 s, or from about 1.9 s to about 8.3 s, or from about 2.0 s to about 8.3 s, or from about 2.1 s to about 8.3 s, or from about 2.2 s to about 8.3 s, or from about 2.3 s to about 8.3 s, or from about 2.4 s to about 8.3 s, or from about 2.5 s to about 8.3 s, or from about 2.6 s to about 8.3 s, or from about 2.7 s to about 8.3 s, or from about 2.8 s to about 8.3 s, or from about 2.9 s to about 8.3 s, or from about 3.0 s to about 8.3 s, or from about 3.1 s to about 8.3 s, or from about 3.2 s to about 8.3 s, or from about 3.3 s to about 8.3 s, or from about 3.4 s to about 8.3 s, or from about 3.4 s to about 8.3 s, or from about 3.5 s to about 8.3 s, or from about 3.6 s to about 8.3 s, or from about 3.7 s to about 8.3 s, or from about 3.8 s to about 8.3 s, or from about 3.9 s to about 8.3 s, or from about 4.0 s to about 8.3 s, or from about 4.1 s to about 8.3 s, or from about 4.2 s to about 8.3 s, or from about 4.3 s to about 8.3 s, or from about 4.4 s to about 8.3 s, or from about 4.5 s to about 8.3 s, or from about 4.6 s to about 8.3 s, or from about 4.7 s to about 8.3 s, or from about 4.8 s to about 8.3 s, or from about 4.9 s to about 8.3 s, or from about 5.0 s to about 8.3 s, or from about 5.1 s to about 8.3 s, or from about 5.2 s to about 8.3 s, or from about 5.3 s to about 8.3 s, or from about 5.4 s to about 8.3 s, or from about 5.5 s to about 8.3 s, or from about 5.6 s to about 8.3 s, or from about 5.7 s to about 8.3 s, or from about 5.8 s to about 8.3 s, or from about 5.9 s to about 8.3 s, or from about 6.0 s to about 8.3 s, or from about 6.1 s to about 8.3 s, or from about 6.2 s to about 8.3 s, or from about 6.3 s to about 8.3 s, or from about 6.4 s to about 8.3 s, or from about 6.5 s to about 8.3 s, or from about 6.6 s to about 8.3 s, or from about 6.7 s to about 8.3 s, or from about 6.8 s to about 8.3 s, or from about 6.9 s to about 8.3 s, or from about 7.0 s to about 8.3 s, or from about 7.1 s to about 8.3 s, or from about 7.2 s to about 8.3 s, or from about 7.3 s to about 8.3 s, or from about 7.4 s to about 8.3 s, or from about 7.5 s to about 8.3 s, or from about 7.6 s to about 8.3 s, or from about 7.7 s to about 8.3 s, or from about 7.8 s to about 8.3 s, or from about 7.9 s to about 8.3 s, or from about 8.0 s to about 8.3 s, or from about 8.1 s to about 8.3 s, or from about 8.2 s to about 8.3 s, or from about 0.1 s to about 8.2 s, or from about 0.2 s to about 8.2 s, or from about 0.3 s to about 8.2 s, or from about 0.4 s to about 8.2 s, or from about 0.5 s to about 8.2 s, or from about 0.6 s to about 8.2 s, or from about 0.7 s to about 8.2 s, or from about 0.8 s to about 8.2 s, or from about 0.9 s to about 8.2 s, or from about 1.0 s to about 8.2 s, or from about 1.1 s to about 8.2 s, or from about 1.2 s to about 8.2 s, or from about 1.3 s to about 8.2 s, or from about 1.4 s to about 8.2 s, or from about 1.5 s to about 8.2 s, or from about 1.6 s to about 8.2 s, or from about 1.7 s to about 8.2 s, or from about 1.8 s to about 8.2 s, or from about 1.9 s to about 8.2 s, or from about 2.0 s to about 8.2 s, or from about 2.1 s to about 8.2 s, or from about 2.2 s to about 8.2 s, or from about 2.3 s to about 8.2 s, or from about 2.4 s to about 8.2 s, or from about 2.5 s to about 8.2 s, or from about 2.6 s to about 8.2 s, or from about 2.7 s to about 8.2 s, or from about 2.8 s to about 8.2 s, or from about 2.9 s to about 8.2 s, or from about 3.0 s to about 8.2 s, or from about 3.1 s to about 8.2 s, or from about 3.2 s to about 8.2 s, or from about 3.3 s to about 8.2 s, or from about 3.4 s to about 8.2 s, or from about 3.4 s to about 8.2 s, or from about 3.5 s to about 8.2 s, or from about 3.6 s to about 8.2 s, or from about 3.7 s to about 8.2 s, or from about 3.8 s to about 8.2 s, or from about 3.9 s to about 8.2 s, or from about 4.0 s to about 8.2 s, or from about 4.1 s to about 8.2 s, or from about 4.2 s to about 8.2 s, or from about 4.3 s to about 8.2 s, or from about 4.4 s to about 8.2 s, or from about 4.5 s to about 8.2 s, or from about 4.6 s to about 8.2 s, or from about 4.7 s to about 8.2 s, or from about 4.8 s to about 8.2 s, or from about 4.9 s to about 8.2 s, or from about 5.0 s to about 8.2 s, or from about 5.1 s to about 8.2 s, or from about 5.2 s to about 8.2 s, or from about 5.3 s to about 8.2 s, or from about 5.4 s to about 8.2 s, or from about 5.5 s to about 8.2 s, or from about 5.6 s to about 8.2 s, or from about 5.7 s to about 8.2 s, or from about 5.8 s to about 8.2 s, or from about 5.9 s to about 8.2 s, or from about 6.0 s to about 8.2 s, or from about 6.1 s to about 8.2 s, or from about 6.2 s to about 8.2 s, or from about 6.3 s to about 8.2 s, or from about 6.4 s to about 8.2 s, or from about 6.5 s to about 8.2 s, or from about 6.6 s to about 8.2 s, or from about 6.7 s to about 8.2 s, or from about 6.8 s to about 8.2 s, or from about 6.9 s to about 8.2 s, or from about 7.0 s to about 8.2 s, or from about 7.1 s to about 8.2 s, or from about 7.2 s to about 8.2 s, or from about 7.3 s to about 8.2 s, or from about 7.4 s to about 8.2 s, or from about 7.5 s to about 8.2 s, or from about 7.6 s to about 8.2 s, or from about 7.7 s to about 8.2 s, or from about 7.8 s to about 8.2 s, or from about 7.9 s to about 8.2 s, or from about 8.0 s to about 8.2 s, or from about 8.1 s to about 8.2 s, or from about 0.1 s to about 8.1 s, or from about 0.2 s to about 8.1 s, or from about 0.3 s to about 8.1 s, or from about 0.4 s to about 8.1 s, or from about 0.5 s to about 8.1 s, or from about 0.6 s to about 8.1 s, or from about 0.7 s to about 8.1 s, or from about 0.8 s to about 8.1 s, or from about 0.9 s to about 8.1 s, or from about 1.0 s to about 8.1 s, or from about 1.1 s to about 8.1 s, or from about 1.2 s to about 8.1 s, or from about 1.3 s to about 8.1 s, or from about 1.4 s to about 8.1 s, or from about 1.5 s to about 8.1 s, or from about 1.6 s to about 8.1 s, or from about 1.7 s to about 8.1 s, or from about 1.8 s to about 8.1 s, or from about 1.9 s to about 8.1 s, or from about 2.0 s to about 8.1 s, or from about 2.1 s to about 8.1 s, or from about 2.2 s to about 8.1 s, or from about 2.3 s to about 8.1 s, or from about 2.4 s to about 8.1 s, or from about 2.5 s to about 8.1 s, or from about 2.6 s to about 8.1 s, or from about 2.7 s to about 8.1 s, or from about 2.8 s to about 8.1 s, or from about 2.9 s to about 8.1 s, or from about 3.0 s to about 8.1 s, or from about 3.1 s to about 8.1 s, or from about 3.2 s to about 8.1 s, or from about 3.3 s to about 8.1 s, or from about 3.4 s to about 8.1 s, or from about 3.4 s to about 8.1 s, or from about 3.5 s to about 8.1 s, or from about 3.6 s to about 8.1 s, or from about 3.7 s to about 8.1 s, or from about 3.8 s to about 8.1 s, or from about 3.9 s to about 8.1 s, or from about 4.0 s to about 8.1 s, or from about 4.1 s to about 8.1 s, or from about 4.2 s to about 8.1 s, or from about 4.3 s to about 8.1 s, or from about 4.4 s to about 8.1 s, or from about 4.5 s to about 8.1 s, or from about 4.6 s to about 8.1 s, or from about 4.7 s to about 8.1 s, or from about 4.8 s to about 8.1 s, or from about 4.9 s to about 8.1 s, or from about 5.0 s to about 8.1 s, or from about 5.1 s to about 8.1 s, or from about 5.2 s to about 8.1 s, or from about 5.3 s to about 8.1 s, or from about 5.4 s to about 8.1 s, or from about 5.5 s to about 8.1 s, or from about 5.6 s to about 8.1 s, or from about 5.7 s to about 8.1 s, or from about 5.8 s to about 8.1 s, or from about 5.9 s to about 8.1 s, or from about 6.0 s to about 8.1 s, or from about 6.1 s to about 8.1 s, or from about 6.2 s to about 8.1 s, or from about 6.3 s to about 8.1 s, or from about 6.4 s to about 8.1 s, or from about 6.5 s to about 8.1 s, or from about 6.6 s to about 8.1 s, or from about 6.7 s to about 8.1 s, or from about 6.8 s to about 8.1 s, or from about 6.9 s to about 8.1 s, or from about 7.0 s to about 8.1 s, or from about 7.1 s to about 8.1 s, or from about 7.2 s to about 8.1 s, or from about 7.3 s to about 8.1 s, or from about 7.4 s to about 8.1 s, or from about 7.5 s to about 8.1 s, or from about 7.6 s to about 8.1 s, or from about 7.7 s to about 8.1 s, or from about 7.8 s to about 8.1 s, or from about 7.9 s to about 8.1 s, or from about 8.0 s to about 8.1 s, or from about 0.1 s to about 8.0 s, or from about 0.2 s to about 8.0 s, or from about 0.3 s to about 8.0 s, or from about 0.4 s to about 8.0 s, or from about 0.5 s to about 8.0 s, or from about 0.6 s to about 8.0 s, or from about 0.7 s to about 8.0 s, or from about 0.8 s to about 8.0 s, or from about 0.9 s to about 8.0 s, or from about 1.0 s to about 8.0 s, or from about 1.1 s to about 8.0 s, or from about 1.2 s to about 8.0 s, or from about 1.3 s to about 8.0 s, or from about 1.4 s to about 8.0 s, or from about 1.5 s to about 8.0 s, or from about 1.6 s to about 8.0 s, or from about 1.7 s to about 8.0 s, or from about 1.8 s to about 8.0 s, or from about 1.9 s to about 8.0 s, or from about 2.0 s to about 8.0 s, or from about 2.1 s to about 8.0 s, or from about 2.2 s to about 8.0 s, or from about 2.3 s to about 8.0 s, or from about 2.4 s to about 8.0 s, or from about 2.5 s to about 8.0 s, or from about 2.6 s to about 8.0 s, or from about 2.7 s to about 8.0 s, or from about 2.8 s to about 8.0 s, or from about 2.9 s to about 8.0 s, or from about 3.0 s to about 8.0 s, or from about 3.1 s to about 8.0 s, or from about 3.2 s to about 8.0 s, or from about 3.3 s to about 8.0 s, or from about 3.4 s to about 8.0 s, or from about 3.4 s to about 8.0 s, or from about 3.5 s to about 8.0 s, or from about 3.6 s to about 8.0 s, or from about 3.7 s to about 8.0 s, or from about 3.8 s to about 8.0 s, or from about 3.9 s to about 8.0 s, or from about 4.0 s to about 8.0 s, or from about 4.1 s to about 8.0 s, or from about 4.2 s to about 8.0 s, or from about 4.3 s to about 8.0 s, or from about 4.4 s to about 8.0 s, or from about 4.5 s to about 8.0 s, or from about 4.6 s to about 8.0 s, or from about 4.7 s to about 8.0 s, or from about 4.8 s to about 8.0 s, or from about 4.9 s to about 8.0 s, or from about 5.0 s to about 8.0 s, or from about 5.1 s to about 8.0 s, or from about 5.2 s to about 8.0 s, or from about 5.3 s to about 8.0 s, or from about 5.4 s to about 8.0 s, or from about 5.5 s to about 8.0 s, or from about 5.6 s to about 8.0 s, or from about 5.7 s to about 8.0 s, or from about 5.8 s to about 8.0 s, or from about 5.9 s to about 8.0 s, or from about 6.0 s to about 8.0 s, or from about 6.1 s to about 8.0 s, or from about 6.2 s to about 8.0 s, or from about 6.3 s to about 8.0 s, or from about 6.4 s to about 8.0 s, or from about 6.5 s to about 8.0 s, or from about 6.6 s to about 8.0 s, or from about 6.7 s to about 8.0 s, or from about 6.8 s to about 8.0 s, or from about 6.9 s to about 8.0 s, or from about 7.0 s to about 8.0 s, or from about 7.1 s to about 8.0 s, or from about 7.2 s to about 8.0 s, or from about 7.3 s to about 8.0 s, or from about 7.4 s to about 8.0 s, or from about 7.5 s to about 8.0 s, or from about 7.6 s to about 8.0 s, or from about 7.7 s to about 8.0 s, or from about 7.8 s to about 8.0 s, or from about 7.9 s to about 8.0 s, or from about 0.1 s to about 7.9 s, or from about 0.2 s to about 7.9 s, or from about 0.3 s to about 7.9 s, or from about 0.4 s to about 7.9 s, or from about 0.5 s to about 7.9 s, or from about 0.6 s to about 7.9 s, or from about 0.7 s to about 7.9 s, or from about 0.8 s to about 7.9 s, or from about 0.9 s to about 7.9 s, or from about 1.0 s to about 7.9 s, or from about 1.1 s to about 7.9 s, or from about 1.2 s to about 7.9 s, or from about 1.3 s to about 7.9 s, or from about 1.4 s to about 7.9 s, or from about 1.5 s to about 7.9 s, or from about 1.6 s to about 7.9 s, or from about 1.7 s to about 7.9 s, or from about 1.8 s to about 7.9 s, or from about 1.9 s to about 7.9 s, or from about 2.0 s to about 7.9 s, or from about 2.1 s to about 7.9 s, or from about 2.2 s to about 7.9 s, or from about 2.3 s to about 7.9 s, or from about 2.4 s to about 7.9 s, or from about 2.5 s to about 7.9 s, or from about 2.6 s to about 7.9 s, or from about 2.7 s to about 7.9 s, or from about 2.8 s to about 7.9 s, or from about 2.9 s to about 7.9 s, or from about 3.0 s to about 7.9 s, or from about 3.1 s to about 7.9 s, or from about 3.2 s to about 7.9 s, or from about 3.3 s to about 7.9 s, or from about 3.4 s to about 7.9 s, or from about 3.4 s to about 7.9 s, or from about 3.5 s to about 7.9 s, or from about 3.6 s to about 7.9 s, or from about 3.7 s to about 7.9 s, or from about 3.8 s to about 7.9 s, or from about 3.9 s to about 7.9 s, or from about 4.0 s to about 7.9 s, or from about 4.1 s to about 7.9 s, or from about 4.2 s to about 7.9 s, or from about 4.3 s to about 7.9 s, or from about 4.4 s to about 7.9 s, or from about 4.5 s to about 7.9 s, or from about 4.6 s to about 7.9 s, or from about 4.7 s to about 7.9 s, or from about 4.8 s to about 7.9 s, or from about 4.9 s to about 7.9 s, or from about 5.0 s to about 7.9 s, or from about 5.1 s to about 7.9 s, or from about 5.2 s to about 7.9 s, or from about 5.3 s to about 7.9 s, or from about 5.4 s to about 7.9 s, or from about 5.5 s to about 7.9 s, or from about 5.6 s to about 7.9 s, or from about 5.7 s to about 7.9 s, or from about 5.8 s to about 7.9 s, or from about 5.9 s to about 7.9 s, or from about 6.0 s to about 7.9 s, or from about 6.1 s to about 7.9 s, or from about 6.2 s to about 7.9 s, or from about 6.3 s to about 7.9 s, or from about 6.4 s to about 7.9 s, or from about 6.5 s to about 7.9 s, or from about 6.6 s to about 7.9 s, or from about 6.7 s to about 7.9 s, or from about 6.8 s to about 7.9 s, or from about 6.9 s to about 7.9 s, or from about 7.0 s to about 7.9 s, or from about 7.1 s to about 7.9 s, or from about 7.2 s to about 7.9 s, or from about 7.3 s to about 7.9 s, or from about 7.4 s to about 7.9 s, or from about 7.5 s to about 7.9 s, or from about 7.6 s to about 7.9 s, or from about 7.7 s to about 7.9 s, or from about 7.8 s to about 7.9 s, or from about 0.1 s to about 7.8 s, or from about 0.2 s to about 7.8 s, or from about 0.3 s to about 7.8 s, or from about 0.4 s to about 7.8 s, or from about 0.5 s to about 7.8 s, or from about 0.6 s to about 7.8 s, or from about 0.7 s to about 7.8 s, or from about 0.8 s to about 7.8 s, or from about 0.9 s to about 7.8 s, or from about 1.0 s to about 7.8 s, or from about 1.1 s to about 7.8 s, or from about 1.2 s to about 7.8 s, or from about 1.3 s to about 7.8 s, or from about 1.4 s to about 7.8 s, or from about 1.5 s to about 7.8 s, or from about 1.6 s to about 7.8 s, or from about 1.7 s to about 7.8 s, or from about 1.8 s to about 7.8 s, or from about 1.9 s to about 7.8 s, or from about 2.0 s to about 7.8 s, or from about 2.1 s to about 7.8 s, or from about 2.2 s to about 7.8 s, or from about 2.3 s to about 7.8 s, or from about 2.4 s to about 7.8 s, or from about 2.5 s to about 7.8 s, or from about 2.6 s to about 7.8 s, or from about 2.7 s to about 7.8 s, or from about 2.8 s to about 7.8 s, or from about 2.9 s to about 7.8 s, or from about 3.0 s to about 7.8 s, or from about 3.1 s to about 7.8 s, or from about 3.2 s to about 7.8 s, or from about 3.3 s to about 7.8 s, or from about 3.4 s to about 7.8 s, or from about 3.4 s to about 7.8 s, or from about 3.5 s to about 7.8 s, or from about 3.6 s to about 7.8 s, or from about 3.7 s to about 7.8 s, or from about 3.8 s to about 7.8 s, or from about 3.9 s to about 7.8 s, or from about 4.0 s to about 7.8 s, or from about 4.1 s to about 7.8 s, or from about 4.2 s to about 7.8 s, or from about 4.3 s to about 7.8 s, or from about 4.4 s to about 7.8 s, or from about 4.5 s to about 7.8 s, or from about 4.6 s to about 7.8 s, or from about 4.7 s to about 7.8 s, or from about 4.8 s to about 7.8 s, or from about 4.9 s to about 7.8 s, or from about 5.0 s to about 7.8 s, or from about 5.1 s to about 7.8 s, or from about 5.2 s to about 7.8 s, or from about 5.3 s to about 7.8 s, or from about 5.4 s to about 7.8 s, or from about 5.5 s to about 7.8 s, or from about 5.6 s to about 7.8 s, or from about 5.7 s to about 7.8 s, or from about 5.8 s to about 7.8 s, or from about 5.9 s to about 7.8 s, or from about 6.0 s to about 7.8 s, or from about 6.1 s to about 7.8 s, or from about 6.2 s to about 7.8 s, or from about 6.3 s to about 7.8 s, or from about 6.4 s to about 7.8 s, or from about 6.5 s to about 7.8 s, or from about 6.6 s to about 7.8 s, or from about 6.7 s to about 7.8 s, or from about 6.8 s to about 7.8 s, or from about 6.9 s to about 7.8 s, or from about 7.0 s to about 7.8 s, or from about 7.1 s to about 7.8 s, or from about 7.2 s to about 7.8 s, or from about 7.3 s to about 7.8 s, or from about 7.4 s to about 7.8 s, or from about 7.5 s to about 7.8 s, or from about 7.6 s to about 7.8 s, or from about 7.7 s to about 7.8 s, or from about 0.1 s to about 7.7 s, or from about 0.2 s to about 7.7 s, or from about 0.3 s to about 7.7 s, or from about 0.4 s to about 7.7 s, or from about 0.5 s to about 7.7 s, or from about 0.6 s to about 7.7 s, or from about 0.7 s to about 7.7 s, or from about 0.8 s to about 7.7 s, or from about 0.9 s to about 7.7 s, or from about 1.0 s to about 7.7 s, or from about 1.1 s to about 7.7 s, or from about 1.2 s to about 7.7 s, or from about 1.3 s to about 7.7 s, or from about 1.4 s to about 7.7 s, or from about 1.5 s to about 7.7 s, or from about 1.6 s to about 7.7 s, or from about 1.7 s to about 7.7 s, or from about 1.8 s to about 7.7 s, or from about 1.9 s to about 7.7 s, or from about 2.0 s to about 7.7 s, or from about 2.1 s to about 7.7 s, or from about 2.2 s to about 7.7 s, or from about 2.3 s to about 7.7 s, or from about 2.4 s to about 7.7 s, or from about 2.5 s to about 7.7 s, or from about 2.6 s to about 7.7 s, or from about 2.7 s to about 7.7 s, or from about 2.8 s to about 7.7 s, or from about 2.9 s to about 7.7 s, or from about 3.0 s to about 7.7 s, or from about 3.1 s to about 7.7 s, or from about 3.2 s to about 7.7 s, or from about 3.3 s to about 7.7 s, or from about 3.4 s to about 7.7 s, or from about 3.4 s to about 7.7 s, or from about 3.5 s to about 7.7 s, or from about 3.6 s to about 7.7 s, or from about 3.7 s to about 7.7 s, or from about 3.8 s to about 7.7 s, or from about 3.9 s to about 7.7 s, or from about 4.0 s to about 7.7 s, or from about 4.1 s to about 7.7 s, or from about 4.2 s to about 7.7 s, or from about 4.3 s to about 71 s, or from about 4.4 s to about 7.7 s, or from about 4.5 s to about 7.7 s, or from about 4.6 s to about 7.7 s, or from about 4.7 s to about 7.7 s, or from about 4.8 s to about 7.7 s, or from about 4.9 s to about 7.7 s, or from about 5.0 s to about 7.7 s, or from about 5.1 s to about 7.7 s, or from about 5.2 s to about 7.7 s, or from about 5.3 s to about 7.7 s, or from about 5.4 s to about 7.7 s, or from about 5.5 s to about 7.7 s, or from about 5.6 s to about 7.7 s, or from about 5.7 s to about 7.7 s, or from about 5.8 s to about 7.7 s, or from about 5.9 s to about 7.7 s, or from about 6.0 s to about 7.7 s, or from about 6.1 s to about 7.7 s, or from about 6.2 s to about 7.7 s, or from about 6.3 s to about 7.7 s, or from about 6.4 s to about 7.7 s, or from about 6.5 s to about 7.7 s, or from about 6.6 s to about 7.7 s, or from about 6.7 s to about 7.7 s, or from about 6.8 s to about 7.7 s, or from about 6.9 s to about 7.7 s, or from about 7.0 s to about 7.7 s, or from about 7.1 s to about 7.7 s, or from about 7.2 s to about 7.7 s, or from about 7.3 s to about 7.7 s, or from about 7.4 s to about 7.7 s, or from about 7.5 s to about 7.7 s, or from about 7.6 s to about 7.7 s, or from about 0.1 s to about 7.6 s, or from about 0.2 s to about 7.6 s, or from about 0.3 s to about 7.6 s, or from about 0.4 s to about 7.6 s, or from about 0.5 s to about 7.6 s, or from about 0.6 s to about 7.6 s, or from about 0.7 s to about 7.6 s, or from about 0.8 s to about 7.6 s, or from about 0.9 s to about 7.6 s, or from about 1.0 s to about 7.6 s, or from about 1.1 s to about 7.6 s, or from about 1.2 s to about 7.6 s, or from about 1.3 s to about 7.6 s, or from about 1.4 s to about 7.6 s, or from about 1.5 s to about 7.6 s, or from about 1.6 s to about 7.6 s, or from about 1.7 s to about 7.6 s, or from about 1.8 s to about 7.6 s, or from about 1.9 s to about 7.6 s, or from about 2.0 s to about 7.6 s, or from about 2.1 s to about 7.6 s, or from about 2.2 s to about 7.6 s, or from about 2.3 s to about 7.6 s, or from about 2.4 s to about 7.6 s, or from about 2.5 s to about 7.6 s, or from about 2.6 s to about 7.6 s, or from about 2.7 s to about 7.6 s, or from about 2.8 s to about 7.6 s, or from about 2.9 s to about 7.6 s, or from about 3.0 s to about 7.6 s, or from about 3.1 s to about 7.6 s, or from about 3.2 s to about 7.6 s, or from about 3.3 s to about 7.6 s, or from about 3.4 s to about 7.6 s, or from about 3.4 s to about 7.6 s, or from about 3.5 s to about 7.6 s, or from about 3.6 s to about 7.6 s, or from about 3.7 s to about 7.6 s, or from about 3.8 s to about 7.6 s, or from about 3.9 s to about 7.6 s, or from about 4.0 s to about 7.6 s, or from about 4.1 s to about 7.6 s, or from about 4.2 s to about 7.6 s, or from about 4.3 s to about 7.6 s, or from about 4.4 s to about 7.6 s, or from about 4.5 s to about 7.6 s, or from about 4.6 s to about 7.6 s, or from about 4.7 s to about 7.6 s, or from about 4.8 s to about 7.6 s, or from about 4.9 s to about 7.6 s, or from about 5.0 s to about 7.6 s, or from about 5.1 s to about 7.6 s, or from about 5.2 s to about 7.6 s, or from about 5.3 s to about 7.6 s, or from about 5.4 s to about 7.6 s, or from about 5.5 s to about 7.6 s, or from about 5.6 s to about 7.6 s, or from about 5.7 s to about 7.6 s, or from about 5.8 s to about 7.6 s, or from about 5.9 s to about 7.6 s, or from about 6.0 s to about 7.6 s, or from about 6.1 s to about 7.6 s, or from about 6.2 s to about 7.6 s, or from about 6.3 s to about 7.6 s, or from about 6.4 s to about 7.6 s, or from about 6.5 s to about 7.6 s, or from about 6.6 s to about 7.6 s, or from about 6.7 s to about 7.6 s, or from about 6.8 s to about 7.6 s, or from about 6.9 s to about 7.6 s, or from about 7.0 s to about 7.6 s, or from about 7.1 s to about 7.6 s, or from about 7.2 s to about 7.6 s, or from about 7.3 s to about 7.6 s, or from about 7.4 s to about 7.6 s, or from about 7.5 s to about 7.6 s, or from about 0.1 s to about 7.5 s, or from about 0.2 s to about 7.5 s, or from about 0.3 s to about 7.5 s, or from about 0.4 s to about 7.5 s, or from about 0.5 s to about 7.5 s, or from about 0.6 s to about 7.5 s, or from about 0.7 s to about 7.5 s, or from about 0.8 s to about 7.5 s, or from about 0.9 s to about 7.5 s, or from about 1.0 s to about 7.5 s, or from about 1.1 s to about 7.5 s, or from about 1.2 s to about 7.5 s, or from about 1.3 s to about 7.5 s, or from about 1.4 s to about 7.5 s, or from about 1.5 s to about 7.5 s, or from about 1.6 s to about 7.5 s, or from about 1.7 s to about 7.5 s, or from about 1.8 s to about 7.5 s, or from about 1.9 s to about 7.5 s, or from about 2.0 s to about 7.5 s, or from about 2.1 s to about 7.5 s, or from about 2.2 s to about 7.5 s, or from about 2.3 s to about 7.5 s, or from about 2.4 s to about 7.5 s, or from about 2.5 s to about 7.5 s, or from about 2.6 s to about 7.5 s, or from about 2.7 s to about 7.5 s, or from about 2.8 s to about 7.5 s, or from about 2.9 s to about 7.5 s, or from about 3.0 s to about 7.5 s, or from about 3.1 s to about 7.5 s, or from about 3.2 s to about 7.5 s, or from about 3.3 s to about 7.5 s, or from about 3.4 s to about 7.5 s, or from about 3.4 s to about 7.5 s, or from about 3.5 s to about 7.5 s, or from about 3.6 s to about 7.5 s, or from about 3.7 s to about 7.5 s, or from about 3.8 s to about 7.5 s, or from about 3.9 s to about 7.5 s, or from about 4.0 s to about 7.5 s, or from about 4.1 s to about 7.5 s, or from about 4.2 s to about 7.5 s, or from about 4.3 s to about 7.5 s, or from about 4.4 s to about 7.5 s, or from about 4.5 s to about 7.5 s, or from about 4.6 s to about 7.5 s, or from about 4.7 s to about 7.5 s, or from about 4.8 s to about 7.5 s, or from about 4.9 s to about 7.5 s, or from about 5.0 s to about 7.5 s, or from about 5.1 s to about 7.5 s, or from about 5.2 s to about 7.5 s, or from about 5.3 s to about 7.5 s, or from about 5.4 s to about 7.5 s, or from about 5.5 s to about 7.5 s, or from about 5.6 s to about 7.5 s, or from about 5.7 s to about 7.5 s, or from about 5.8 s to about 7.5 s, or from about 5.9 s to about 7.5 s, or from about 6.0 s to about 7.5 s, or from about 6.1 s to about 7.5 s, or from about 6.2 s to about 7.5 s, or from about 6.3 s to about 7.5 s, or from about 6.4 s to about 7.5 s, or from about 6.5 s to about 7.5 s, or from about 6.6 s to about 7.5 s, or from about 6.7 s to about 7.5 s, or from about 6.8 s to about 7.5 s, or from about 6.9 s to about 7.5 s, or from about 7.0 s to about 7.5 s, or from about 7.1 s to about 7.5 s, or from about 7.2 s to about 7.5 s, or from about 7.3 s to about 7.5 s, or from about 7.4 s to about 7.5 s, or from about 0.1 s to about 7.4 s, or from about 0.2 s to about 7.4 s, or from about 0.3 s to about 7.4 s, or from about 0.4 s to about 7.4 s, or from about 0.5 s to about 7.4 s, or from about 0.6 s to about 7.4 s, or from about 0.7 s to about 7.4 s, or from about 0.8 s to about 7.4 s, or from about 0.9 s to about 7.4 s, or from about 1.0 s to about 7.4 s, or from about 1.1 s to about 7.4 s, or from about 1.2 s to about 7.4 s, or from about 1.3 s to about 7.4 s, or from about 1.4 s to about 7.4 s, or from about 1.5 s to about 7.4 s, or from about 1.6 s to about 7.4 s, or from about 1.7 s to about 7.4 s, or from about 1.8 s to about 7.4 s, or from about 1.9 s to about 7.4 s, or from about 2.0 s to about 7.4 s, or from about 2.1 s to about 7.4 s, or from about 2.2 s to about 7.4 s, or from about 2.3 s to about 7.4 s, or from about 2.4 s to about 7.4 s, or from about 2.5 s to about 7.4 s, or from about 2.6 s to about 7.4 s, or from about 2.7 s to about 7.4 s, or from about 2.8 s to about 7.4 s, or from about 2.9 s to about 7.4 s, or from about 3.0 s to about 7.4 s, or from about 3.1 s to about 7.4 s, or from about 3.2 s to about 7.4 s, or from about 3.3 s to about 7.4 s, or from about 3.4 s to about 7.4 s, or from about 3.4 s to about 7.4 s, or from about 3.5 s to about 7.4 s, or from about 3.6 s to about 7.4 s, or from about 3.7 s to about 7.4 s, or from about 3.8 s to about 7.4 s, or from about 3.9 s to about 7.4 s, or from about 4.0 s to about 7.4 s, or from about 4.1 s to about 7.4 s, or from about 4.2 s to about 7.4 s, or from about 4.3 s to about 7.4 s, or from about 4.4 s to about 7.4 s, or from about 4.5 s to about 7.4 s, or from about 4.6 s to about 7.4 s, or from about 4.7 s to about 7.4 s, or from about 4.8 s to about 7.4 s, or from about 4.9 s to about 7.4 s, or from about 5.0 s to about 7.4 s, or from about 5.1 s to about 7.4 s, or from about 5.2 s to about 7.4 s, or from about 5.3 s to about 7.4 s, or from about 5.4 s to about 7.4 s, or from about 5.5 s to about 7.4 s, or from about 5.6 s to about 7.4 s, or from about 5.7 s to about 7.4 s, or from about 5.8 s to about 7.4 s, or from about 5.9 s to about 7.4 s, or from about 6.0 s to about 7.4 s, or from about 6.1 s to about 7.4 s, or from about 6.2 s to about 7.4 s, or from about 6.3 s to about 7.4 s, or from about 6.4 s to about 7.4 s, or from about 6.5 s to about 7.4 s, or from about 6.6 s to about 7.4 s, or from about 6.7 s to about 7.4 s, or from about 6.8 s to about 7.4 s, or from about 6.9 s to about 7.4 s, or from about 7.0 s to about 7.4 s, or from about 7.1 s to about 7.4 s, or from about 7.2 s to about 7.4 s, or from about 7.3 s to about 7.4 s, or from about 0.1 s to about 7.3 s, or from about 0.2 s to about 7.3 s, or from about 0.3 s to about 7.3 s, or from about 0.4 s to about 7.3 s, or from about 0.5 s to about 7.3 s, or from about 0.6 s to about 7.3 s, or from about 0.7 s to about 7.3 s, or from about 0.8 s to about 7.3 s, or from about 0.9 s to about 7.3 s, or from about 1.0 s to about 7.3 s, or from about 1.1 s to about 7.3 s, or from about 1.2 s to about 7.3 s, or from about 1.3 s to about 7.3 s, or from about 1.4 s to about 7.3 s, or from about 1.5 s to about 7.3 s, or from about 1.6 s to about 7.3 s, or from about 1.7 s to about 7.3 s, or from about 1.8 s to about 7.3 s, or from about 1.9 s to about 7.3 s, or from about 2.0 s to about 7.3 s, or from about 2.1 s to about 7.3 s, or from about 2.2 s to about 7.3 s, or from about 2.3 s to about 7.3 s, or from about 2.4 s to about 7.3 s, or from about 2.5 s to about 7.3 s, or from about 2.6 s to about 7.3 s, or from about 2.7 s to about 7.3 s, or from about 2.8 s to about 7.3 s, or from about 2.9 s to about 7.3 s, or from about 3.0 s to about 7.3 s, or from about 3.1 s to about 7.3 s, or from about 3.2 s to about 7.3 s, or from about 3.3 s to about 7.3 s, or from about 3.4 s to about 7.3 s, or from about 3.4 s to about 7.3 s, or from about 3.5 s to about 7.3 s, or from about 3.6 s to about 7.3 s, or from about 3.7 s to about 7.3 s, or from about 3.8 s to about 7.3 s, or from about 3.9 s to about 7.3 s, or from about 4.0 s to about 7.3 s, or from about 4.1 s to about 7.3 s, or from about 4.2 s to about 7.3 s, or from about 4.3 s to about 7.3 s, or from about 4.4 s to about 7.3 s, or from about 4.5 s to about 7.3 s, or from about 4.6 s to about 7.3 s, or from about 4.7 s to about 7.3 s, or from about 4.8 s to about 7.3 s, or from about 4.9 s to about 7.3 s, or from about 5.0 s to about 7.3 s, or from about 5.1 s to about 7.3 s, or from about 5.2 s to about 7.3 s, or from about 5.3 s to about 7.3 s, or from about 5.4 s to about 7.3 s, or from about 5.5 s to about 7.3 s, or from about 5.6 s to about 7.3 s, or from about 5.7 s to about 7.3 s, or from about 5.8 s to about 7.3 s, or from about 5.9 s to about 7.3 s, or from about 6.0 s to about 7.3 s, or from about 6.1 s to about 7.3 s, or from about 6.2 s to about 7.3 s, or from about 6.3 s to about 7.3 s, or from about 6.4 s to about 7.3 s, or from about 6.5 s to about 7.3 s, or from about 6.6 s to about 7.3 s, or from about 6.7 s to about 7.3 s, or from about 6.8 s to about 7.3 s, or from about 6.9 s to about 7.3 s, or from about 7.0 s to about 7.3 s, or from about 7.1 s to about 7.3 s, or from about 7.2 s to about 7.3 s, or from about 0.1 s to about 7.2 s, or from about 0.2 s to about 7.2 s, or from about 0.3 s to about 7.2 s, or from about 0.4 s to about 7.2 s, or from about 0.5 s to about 7.2 s, or from about 0.6 s to about 7.2 s, or from about 0.7 s to about 7.2 s, or from about 0.8 s to about 7.2 s, or from about 0.9 s to about 7.2 s, or from about 1.0 s to about 7.2 s, or from about 1.1 s to about 7.2 s, or from about 1.2 s to about 7.2 s, or from about 1.3 s to about 7.2 s, or from about 1.4 s to about 7.2 s, or from about 1.5 s to about 7.2 s, or from about 1.6 s to about 7.2 s, or from about 1.7 s to about 7.2 s, or from about 1.8 s to about 7.2 s, or from about 1.9 s to about 7.2 s, or from about 2.0 s to about 7.2 s, or from about 2.1 s to about 7.2 s, or from about 2.2 s to about 7.2 s, or from about 2.3 s to about 7.2 s, or from about 2.4 s to about 7.2 s, or from about 2.5 s to about 7.2 s, or from about 2.6 s to about 7.2 s, or from about 2.7 s to about 7.2 s, or from about 2.8 s to about 7.2 s, or from about 2.9 s to about 7.2 s, or from about 3.0 s to about 7.2 s, or from about 3.1 s to about 7.2 s, or from about 3.2 s to about 7.2 s, or from about 3.3 s to about 7.2 s, or from about 3.4 s to about 7.2 s, or from about 3.4 s to about 7.2 s, or from about 3.5 s to about 7.2 s, or from about 3.6 s to about 7.2 s, or from about 3.7 s to about 7.2 s, or from about 3.8 s to about 7.2 s, or from about 3.9 s to about 7.2 s, or from about 4.0 s to about 7.2 s, or from about 4.1 s to about 7.2 s, or from about 4.2 s to about 7.2 s, or from about 4.3 s to about 7.2 s, or from about 4.4 s to about 7.2 s, or from about 4.5 s to about 7.2 s, or from about 4.6 s to about 7.2 s, or from about 4.7 s to about 7.2 s, or from about 4.8 s to about 7.2 s, or from about 4.9 s to about 7.2 s, or from about 5.0 s to about 7.2 s, or from about 5.1 s to about 7.2 s, or from about 5.2 s to about 7.2 s, or from about 5.3 s to about 7.2 s, or from about 5.4 s to about 7.2 s, or from about 5.5 s to about 7.2 s, or from about 5.6 s to about 7.2 s, or from about 5.7 s to about 7.2 s, or from about 5.8 s to about 7.2 s, or from about 5.9 s to about 7.2 s, or from about 6.0 s to about 7.2 s, or from about 6.1 s to about 7.2 s, or from about 6.2 s to about 7.2 s, or from about 6.3 s to about 7.2 s, or from about 6.4 s to about 7.2 s, or from about 6.5 s to about 7.2 s, or from about 6.6 s to about 7.2 s, or from about 6.7 s to about 7.2 s, or from about 6.8 s to about 7.2 s, or from about 6.9 s to about 7.2 s, or from about 7.0 s to about 7.2 s, or from about 7.1 s to about 7.2 s, or from about 0.1 s to about 7.1 s, or from about 0.2 s to about 7.1 s, or from about 0.3 s to about 7.1 s, or from about 0.4 s to about 7.1 s, or from about 0.5 s to about 7.1 s, or from about 0.6 s to about 7.1 s, or from about 0.7 s to about 7.1 s, or from about 0.8 s to about 7.1 s, or from about 0.9 s to about 7.1 s, or from about 1.0 s to about 7.1 s, or from about 1.1 s to about 7.1 s, or from about 1.2 s to about 7.1 s, or from about 1.3 s to about 7.1 s, or from about 1.4 s to about 7.1 s, or from about 1.5 s to about 7.1 s, or from about 1.6 s to about 7.1 s, or from about 1.7 s to about 7.1 s, or from about 1.8 s to about 7.1 s, or from about 1.9 s to about 7.1 s, or from about 2.0 s to about 7.1 s, or from about 2.1 s to about 7.1 s, or from about 2.2 s to about 7.1 s, or from about 2.3 s to about 7.1 s, or from about 2.4 s to about 7.1 s, or from about 2.5 s to about 7.1 s, or from about 2.6 s to about 7.1 s, or from about 2.7 s to about 7.1 s, or from about 2.8 s to about 7.1 s, or from about 2.9 s to about 7.1 s, or from about 3.0 s to about 7.1 s, or from about 3.1 s to about 7.1 s, or from about 3.2 s to about 7.1 s, or from about 3.3 s to about 7.1 s, or from about 3.4 s to about 7.1 s, or from about 3.4 s to about 7.1 s, or from about 3.5 s to about 7.1 s, or from about 3.6 s to about 7.1 s, or from about 3.7 s to about 7.1 s, or from about 3.8 s to about 7.1 s, or from about 3.9 s to about 7.1 s, or from about 4.0 s to about 7.1 s, or from about 4.1 s to about 7.1 s, or from about 4.2 s to about 7.1 s, or from about 4.3 s to about 7.1 s, or from about 4.4 s to about 7.1 s, or from about 4.5 s to about 7.1 s, or from about 4.6 s to about 7.1 s, or from about 4.7 s to about 7.1 s, or from about 4.8 s to about 7.1 s, or from about 4.9 s to about 7.1 s, or from about 5.0 s to about 7.1 s, or from about 5.1 s to about 7.1 s, or from about 5.2 s to about 7.1 s, or from about 5.3 s to about 7.1 s, or from about 5.4 s to about 7.1 s, or from about 5.5 s to about 7.1 s, or from about 5.6 s to about 7.1 s, or from about 5.7 s to about 7.1 s, or from about 5.8 s to about 7.1 s, or from about 5.9 s to about 7.1 s, or from about 6.0 s to about 7.1 s, or from about 6.1 s to about 7.1 s, or from about 6.2 s to about 7.1 s, or from about 6.3 s to about 7.1 s, or from about 6.4 s to about 7.1 s, or from about 6.5 s to about 7.1 s, or from about 6.6 s to about 7.1 s, or from about 6.7 s to about 7.1 s, or from about 6.8 s to about 7.1 s, or from about 6.9 s to about 7.1 s, or from about 7.0 s to about 7.1 s, or from about 0.1 s to about 7.0 s, or from about 0.2 s to about 7.0 s, or from about 0.3 s to about 7.0 s, or from about 0.4 s to about 7.0 s, or from about 0.5 s to about 7.0 s, or from about 0.6 s to about 7.0 s, or from about 0.7 s to about 7.0 s, or from about 0.8 s to about 7.0 s, or from about 0.9 s to about 7.0 s, or from about 1.0 s to about 7.0 s, or from about 1.1 s to about 7.0 s, or from about 1.2 s to about 7.0 s, or from about 1.3 s to about 7.0 s, or from about 1.4 s to about 7.0 s, or from about 1.5 s to about 7.0 s, or from about 1.6 s to about 7.0 s, or from about 1.7 s to about 7.0 s, or from about 1.8 s to about 7.0 s, or from about 1.9 s to about 7.0 s, or from about 2.0 s to about 7.0 s, or from about 2.1 s to about 7.0 s, or from about 2.2 s to about 7.0 s, or from about 2.3 s to about 7.0 s, or from about 2.4 s to about 7.0 s, or from about 2.5 s to about 7.0 s, or from about 2.6 s to about 7.0 s, or from about 2.7 s to about 7.0 s, or from about 2.8 s to about 7.0 s, or from about 2.9 s to about 7.0 s, or from about 3.0 s to about 7.0 s, or from about 3.1 s to about 7.0 s, or from about 3.2 s to about 7.0 s, or from about 3.3 s to about 7.0 s, or from about 3.4 s to about 7.0 s, or from about 3.4 s to about 7.0 s, or from about 3.5 s to about 7.0 s, or from about 3.6 s to about 7.0 s, or from about 3.7 s to about 7.0 s, or from about 3.8 s to about 7.0 s, or from about 3.9 s to about 7.0 s, or from about 4.0 s to about 7.0 s, or from about 4.1 s to about 7.0 s, or from about 4.2 s to about 7.0 s, or from about 4.3 s to about 7.0 s, or from about 4.4 s to about 7.0 s, or from about 4.5 s to about 7.0 s, or from about 4.6 s to about 7.0 s, or from about 4.7 s to about 7.0 s, or from about 4.8 s to about 7.0 s, or from about 4.9 s to about 7.0 s, or from about 5.0 s to about 7.0 s, or from about 5.1 s to about 7.0 s, or from about 5.2 s to about 7.0 s, or from about 5.3 s to about 7.0 s, or from about 5.4 s to about 7.0 s, or from about 5.5 s to about 7.0 s, or from about 5.6 s to about 7.0 s, or from about 5.7 s to about 7.0 s, or from about 5.8 s to about 7.0 s, or from about 5.9 s to about 7.0 s, or from about 6.0 s to about 7.0 s, or from about 6.1 s to about 7.0 s, or from about 6.2 s to about 7.0 s, or from about 6.3 s to about 7.0 s, or from about 6.4 s to about 7.0 s, or from about 6.5 s to about 7.0 s, or from about 6.6 s to about 7.0 s, or from about 6.7 s to about 7.0 s, or from about 6.8 s to about 7.0 s, or from about 6.9 s to about 7.0 s, or from about 0.1 s to about 6.9 s, or from about 0.2 s to about 6.9 s, or from about 0.3 s to about 6.9 s, or from about 0.4 s to about 6.9 s, or from about 0.5 s to about 6.9 s, or from about 0.6 s to about 6.9 s, or from about 0.7 s to about 6.9 s, or from about 0.8 s to about 6.9 s, or from about 0.9 s to about 6.9 s, or from about 1.0 s to about 6.9 s, or from about 1.1 s to about 6.9 s, or from about 1.2 s to about 6.9 s, or from about 1.3 s to about 6.9 s, or from about 1.4 s to about 6.9 s, or from about 1.5 s to about 6.9 s, or from about 1.6 s to about 6.9 s, or from about 1.7 s to about 6.9 s, or from about 1.8 s to about 6.9 s, or from about 1.9 s to about 6.9 s, or from about 2.0 s to about 6.9 s, or from about 2.1 s to about 6.9 s, or from about 2.2 s to about 6.9 s, or from about 2.3 s to about 6.9 s, or from about 2.4 s to about 6.9 s, or from about 2.5 s to about 6.9 s, or from about 2.6 s to about 6.9 s, or from about 2.7 s to about 6.9 s, or from about 2.8 s to about 6.9 s, or from about 2.9 s to about 6.9 s, or from about 3.0 s to about 6.9 s, or from about 3.1 s to about 6.9 s, or from about 3.2 s to about 6.9 s, or from about 3.3 s to about 6.9 s, or from about 3.4 s to about 6.9 s, or from about 3.4 s to about 6.9 s, or from about 3.5 s to about 6.9 s, or from about 3.6 s to about 6.9 s, or from about 3.7 s to about 6.9 s, or from about 3.8 s to about 6.9 s, or from about 3.9 s to about 6.9 s, or from about 4.0 s to about 6.9 s, or from about 4.1 s to about 6.9 s, or from about 4.2 s to about 6.9 s, or from about 4.3 s to about 6.9 s, or from about 4.4 s to about 6.9 s, or from about 4.5 s to about 6.9 s, or from about 4.6 s to about 6.9 s, or from about 4.7 s to about 6.9 s, or from about 4.8 s to about 6.9 s, or from about 4.9 s to about 6.9 s, or from about 5.0 s to about 6.9 s, or from about 5.1 s to about 6.9 s, or from about 5.2 s to about 6.9 s, or from about 5.3 s to about 6.9 s, or from about 5.4 s to about 6.9 s, or from about 5.5 s to about 6.9 s, or from about 5.6 s to about 6.9 s, or from about 5.7 s to about 6.9 s, or from about 5.8 s to about 6.9 s, or from about 5.9 s to about 6.9 s, or from about 6.0 s to about 6.9 s, or from about 6.1 s to about 6.9 s, or from about 6.2 s to about 6.9 s, or from about 6.3 s to about 6.9 s, or from about 6.4 s to about 6.9 s, or from about 6.5 s to about 6.9 s, or from about 6.6 s to about 6.9 s, or from about 6.7 s to about 6.9 s, or from about 6.8 s to about 6.9 s, or from about 0.1 s to about 6.8 s, or from about 0.2 s to about 6.8 s, or from about 0.3 s to about 6.8 s, or from about 0.4 s to about 6.8 s, or from about 0.5 s to about 6.8 s, or from about 0.6 s to about 6.8 s, or from about 0.7 s to about 6.8 s, or from about 0.8 s to about 6.8 s, or from about 0.9 s to about 6.8 s, or from about 1.0 s to about 6.8 s, or from about 1.1 s to about 6.8 s, or from about 1.2 s to about 6.8 s, or from about 1.3 s to about 6.8 s, or from about 1.4 s to about 6.8 s, or from about 1.5 s to about 6.8 s, or from about 1.6 s to about 6.8 s, or from about 1.7 s to about 6.8 s, or from about 1.8 s to about 6.8 s, or from about 1.9 s to about 6.8 s, or from about 2.0 s to about 6.8 s, or from about 2.1 s to about 6.8 s, or from about 2.2 s to about 6.8 s, or from about 2.3 s to about 6.8 s, or from about 2.4 s to about 6.8 s, or from about 2.5 s to about 6.8 s, or from about 2.6 s to about 6.8 s, or from about 2.7 s to about 6.8 s, or from about 2.8 s to about 6.8 s, or from about 2.9 s to about 6.8 s, or from about 3.0 s to about 6.8 s, or from about 3.1 s to about 6.8 s, or from about 3.2 s to about 6.8 s, or from about 3.3 s to about 6.8 s, or from about 3.4 s to about 6.8 s, or from about 3.4 s to about 6.8 s, or from about 3.5 s to about 6.8 s, or from about 3.6 s to about 6.8 s, or from about 3.7 s to about 6.8 s, or from about 3.8 s to about 6.8 s, or from about 3.9 s to about 6.8 s, or from about 4.0 s to about 6.8 s, or from about 4.1 s to about 6.8 s, or from about 4.2 s to about 6.8 s, or from about 4.3 s to about 6.8 s, or from about 4.4 s to about 6.8 s, or from about 4.5 s to about 6.8 s, or from about 4.6 s to about 6.8 s, or from about 4.7 s to about 6.8 s, or from about 4.8 s to about 6.8 s, or from about 4.9 s to about 6.8 s, or from about 5.0 s to about 6.8 s, or from about 5.1 s to about 6.8 s, or from about 5.2 s to about 6.8 s, or from about 5.3 s to about 6.8 s, or from about 5.4 s to about 6.8 s, or from about 5.5 s to about 6.8 s, or from about 5.6 s to about 6.8 s, or from about 5.7 s to about 6.8 s, or from about 5.8 s to about 6.8 s, or from about 5.9 s to about 6.8 s, or from about 6.0 s to about 6.8 s, or from about 6.1 s to about 6.8 s, or from about 6.2 s to about 6.8 s, or from about 6.3 s to about 6.8 s, or from about 6.4 s to about 6.8 s, or from about 6.5 s to about 6.8 s, or from about 6.6 s to about 6.8 s, or from about 6.7 s to about 6.8 s, or from about 0.1 s to about 6.7 s, or from about 0.2 s to about 6.7 s, or from about 0.3 s to about 6.7 s, or from about 0.4 s to about 6.7 s, or from about 0.5 s to about 6.7 s, or from about 0.6 s to about 6.7 s, or from about 0.7 s to about 6.7 s, or from about 0.8 s to about 6.7 s, or from about 0.9 s to about 6.7 s, or from about 1.0 s to about 6.7 s, or from about 1.1 s to about 6.7 s, or from about 1.2 s to about 6.7 s, or from about 1.3 s to about 6.7 s, or from about 1.4 s to about 6.7 s, or from about 1.5 s to about 6.7 s, or from about 1.6 s to about 6.7 s, or from about 1.7 s to about 6.7 s, or from about 1.8 s to about 6.7 s, or from about 1.9 s to about 6.7 s, or from about 2.0 s to about 6.7 s, or from about 2.1 s to about 6.7 s, or from about 2.2 s to about 6.7 s, or from about 2.3 s to about 6.7 s, or from about 2.4 s to about 6.7 s, or from about 2.5 s to about 6.7 s, or from about 2.6 s to about 6.7 s, or from about 2.7 s to about 6.7 s, or from about 2.8 s to about 6.7 s, or from about 2.9 s to about 6.7 s, or from about 3.0 s to about 6.7 s, or from about 3.1 s to about 6.7 s, or from about 3.2 s to about 6.7 s, or from about 3.3 s to about 6.7 s, or from about 3.4 s to about 6.7 s, or from about 3.4 s to about 6.7 s, or from about 3.5 s to about 6.7 s, or from about 3.6 s to about 6.7 s, or from about 3.7 s to about 6.7 s, or from about 3.8 s to about 6.7 s, or from about 3.9 s to about 6.7 s, or from about 4.0 s to about 6.7 s, or from about 4.1 s to about 6.7 s, or from about 4.2 s to about 6.7 s, or from about 4.3 s to about 6.7 s, or from about 4.4 s to about 6.7 s, or from about 4.5 s to about 6.7 s, or from about 4.6 s to about 6.7 s, or from about 4.7 s to about 6.7 s, or from about 4.8 s to about 6.7 s, or from about 4.9 s to about 6.7 s, or from about 5.0 s to about 6.7 s, or from about 5.1 s to about 6.7 s, or from about 5.2 s to about 6.7 s, or from about 5.3 s to about 6.7 s, or from about 5.4 s to about 6.7 s, or from about 5.5 s to about 6.7 s, or from about 5.6 s to about 6.7 s, or from about 5.7 s to about 6.7 s, or from about 5.8 s to about 6.7 s, or from about 5.9 s to about 6.7 s, or from about 6.0 s to about 6.7 s, or from about 6.1 s to about 6.7 s, or from about 6.2 s to about 6.7 s, or from about 6.3 s to about 6.7 s, or from about 6.4 s to about 6.7 s, or from about 6.5 s to about 6.7 s, or from about 6.6 s to about 6.7 s, or from about 0.1 s to about 6.6 s, or from about 0.2 s to about 6.6 s, or from about 0.3 s to about 6.6 s, or from about 0.4 s to about 6.6 s, or from about 0.5 s to about 6.6 s, or from about 0.6 s to about 6.6 s, or from about 0.7 s to about 6.6 s, or from about 0.8 s to about 6.6 s, or from about 0.9 s to about 6.6 s, or from about 1.0 s to about 6.6 s, or from about 1.1 s to about 6.6 s, or from about 1.2 s to about 6.6 s, or from about 1.3 s to about 6.6 s, or from about 1.4 s to about 6.6 s, or from about 1.5 s to about 6.6 s, or from about 1.6 s to about 6.6 s, or from about 1.7 s to about 6.6 s, or from about 1.8 s to about 6.6 s, or from about 1.9 s to about 6.6 s, or from about 2.0 s to about 6.6 s, or from about 2.1 s to about 6.6 s, or from about 2.2 s to about 6.6 s, or from about 2.3 s to about 6.6 s, or from about 2.4 s to about 6.6 s, or from about 2.5 s to about 6.6 s, or from about 2.6 s to about 6.6 s, or from about 2.7 s to about 6.6 s, or from about 2.8 s to about 6.6 s, or from about 2.9 s to about 6.6 s, or from about 3.0 s to about 6.6 s, or from about 3.1 s to about 6.6 s, or from about 3.2 s to about 6.6 s, or from about 3.3 s to about 6.6 s, or from about 3.4 s to about 6.6 s, or from about 3.4 s to about 6.6 s, or from about 3.5 s to about 6.6 s, or from about 3.6 s to about 6.6 s, or from about 3.7 s to about 6.6 s, or from about 3.8 s to about 6.6 s, or from about 3.9 s to about 6.6 s, or from about 4.0 s to about 6.6 s, or from about 4.1 s to about 6.6 s, or from about 4.2 s to about 6.6 s, or from about 4.3 s to about 6.6 s, or from about 4.4 s to about 6.6 s, or from about 4.5 s to about 6.6 s, or from about 4.6 s to about 6.6 s, or from about 4.7 s to about 6.6 s, or from about 4.8 s to about 6.6 s, or from about 4.9 s to about 6.6 s, or from about 5.0 s to about 6.6 s, or from about 5.1 s to about 6.6 s, or from about 5.2 s to about 6.6 s, or from about 5.3 s to about 6.6 s, or from about 5.4 s to about 6.6 s, or from about 5.5 s to about 6.6 s, or from about 5.6 s to about 6.6 s, or from about 5.7 s to about 6.6 s, or from about 5.8 s to about 6.6 s, or from about 5.9 s to about 6.6 s, or from about 6.0 s to about 6.6 s, or from about 6.1 s to about 6.6 s, or from about 6.2 s to about 6.6 s, or from about 6.3 s to about 6.6 s, or from about 6.4 s to about 6.6 s, or from about 6.5 s to about 6.6 s, or from about 0.1 s to about 6.5 s, or from about 0.2 s to about 6.5 s, or from about 0.3 s to about 6.5 s, or from about 0.4 s to about 6.5 s, or from about 0.5 s to about 6.5 s, or from about 0.6 s to about 6.5 s, or from about 0.7 s to about 6.5 s, or from about 0.8 s to about 6.5 s, or from about 0.9 s to about 6.5 s, or from about 1.0 s to about 6.5 s, or from about 1.1 s to about 6.5 s, or from about 1.2 s to about 6.5 s, or from about 1.3 s to about 6.5 s, or from about 1.4 s to about 6.5 s, or from about 1.5 s to about 6.5 s, or from about 1.6 s to about 6.5 s, or from about 1.7 s to about 6.5 s, or from about 1.8 s to about 6.5 s, or from about 1.9 s to about 6.5 s, or from about 2.0 s to about 6.5 s, or from about 2.1 s to about 6.5 s, or from about 2.2 s to about 6.5 s, or from about 2.3 s to about 6.5 s, or from about 2.4 s to about 6.5 s, or from about 2.5 s to about 6.5 s, or from about 2.6 s to about 6.5 s, or from about 2.7 s to about 6.5 s, or from about 2.8 s to about 6.5 s, or from about 2.9 s to about 6.5 s, or from about 3.0 s to about 6.5 s, or from about 3.1 s to about 6.5 s, or from about 3.2 s to about 6.5 s, or from about 3.3 s to about 6.5 s, or from about 3.4 s to about 6.5 s, or from about 3.5 s to about 6.5 s, or from about 3.6 s to about 6.5 s, or from about 3.7 s to about 6.5 s, or from about 3.8 s to about 6.5 s, or from about 3.9 s to about 6.5 s, or from about 4.0 s to about 6.5 s, or from about 4.1 s to about 6.5 s, or from about 4.2 s to about 6.5 s, or from about 4.3 s to about 6.5 s, or from about 4.4 s to about 6.5 s, or from about 4.5 s to about 6.5 s, or from about 4.6 s to about 6.5 s, or from about 4.7 s to about 6.5 s, or from about 4.8 s to about 6.5 s, or from about 4.9 s to about 6.5 s, or from about 5.0 s to about 6.5 s, or from about 5.1 s to about 6.5 s, or from about 5.2 s to about 6.5 s, or from about 5.3 s to about 6.5 s, or from about 5.4 s to about 6.5 s, or from about 5.5 s to about 6.5 s, or from about 5.6 s to about 6.5 s, or from about 5.7 s to about 6.5 s, or from about 5.8 s to about 6.5 s, or from about 5.9 s to about 6.5 s, or from about 6.0 s to about 6.5 s, or from about 6.1 s to about 6.5 s, or from about 6.2 s to about 6.5 s, or from about 6.3 s to about 6.5 s, or from about 6.4 s to about 6.5 s, or from about 0.1 s to about 6.4 s, or from about 0.2 s to about 6.4 s, or from about 0.3 s to about 6.4 s, or from about 0.4 s to about 6.4 s, or from about 0.5 s to about 6.4 s, or from about 0.6 s to about 6.4 s, or from about 0.7 s to about 6.4 s, or from about 0.8 s to about 6.4 s, or from about 0.9 s to about 6.4 s, or from about 1.0 s to about 6.4 s, or from about 1.1 s to about 6.4 s, or from about 1.2 s to about 6.4 s, or from about 1.3 s to about 6.4 s, or from about 1.4 s to about 6.4 s, or from about 1.5 s to about 6.4 s, or from about 0.1.6 s to about 6.4 s, or from about 1.7 s to about 6.4 s, or from about 1.8 s to about 6.4 s, or from about 1.9 s to about 6.4 s, or from about 2.0 s to about 6.4 s, or from about 2.1 s to about 6.4 s, or from about 2.2 s to about 6.4 s, or from about 2.3 s to about 6.4 s, or from about 2.4 s to about 6.4 s, or from about 2.5 s to about 6.4 s, or from about 2.6 s to about 6.4 s, or from about 2.7 s to about 6.4 s, or from about 2.8 s to about 6.4 s, or from about 2.9 s to about 6.4 s, or from about 3.0 s to about 6.4 s, or from about 3.1 s to about 6.4 s, or from about 3.2 s to about 6.4 s, or from about 3.3 s to about 6.4 s, or from about 3.4 s to about 6.4 s, or from about 3.4 s to about 6.4 s, or from about 3.5 s to about 6.4 s, or from about 3.6 s to about 6.4 s, or from about 3.7 s to about 6.4 s, or from about 3.8 s to about 6.4 s, or from about 3.9 s to about 6.4 s, or from about 4.0 s to about 6.4 s, or from about 4.1 s to about 6.4 s, or from about 4.2 s to about 6.4 s, or from about 4.3 s to about 6.4 s, or from about 4.4 s to about 6.4 s, or from about 4.5 s to about 6.4 s, or from about 4.6 s to about 6.4 s, or from about 4.7 s to about 6.4 s, or from about 4.8 s to about 6.4 s, or from about 4.9 s to about 6.4 s, or from about 5.0 s to about 6.4 s, or from about 5.1 s to about 6.4 s, or from about 5.2 s to about 6.4 s, or from about 5.3 s to about 6.4 s, or from about 5.4 s to about 6.4 s, or from about 5.5 s to about 6.4 s, or from about 5.6 s to about 6.4 s, or from about 5.7 s to about 6.4 s, or from about 5.8 s to about 6.4 s, or from about 5.9 s to about 6.4 s, or from about 6.0 s to about 6.4 s, or from about 6.1 s to about 6.4 s, or from about 6.2 s to about 6.4 s, or from about 6.3 s to about 6.4 s, or from about 0.1 s to about 6.3 s, or from about 0.2 s to about 6.3 s, or from about 0.3 s to about 6.3 s, or from about 0.4 s to about 6.3 s, or from about 0.5 s to about 6.3 s, or from about 0.6 s to about 6.3 s, or from about 0.7 s to about 6.3 s, or from about 0.8 s to about 6.3 s, or from about 0.9 s to about 6.3 s, or from about 1.0 s to about 6.3 s, or from about 1.1 s to about 6.3 s, or from about 1.2 s to about 6.3 s, or from about 1.3 s to about 6.3 s, or from about 1.4 s to about 6.3 s, or from about 1.5 s to about 6.3 s, or from about 1.6 s to about 6.3 s, or from about 1.7 s to about 6.3 s, or from about 1.8 s to about 6.3 s, or from about 1.9 s to about 6.3 s, or from about 2.0 s to about 6.3 s, or from about 2.1 s to about 6.3 s, or from about 2.2 s to about 6.3 s, or from about 2.3 s to about 6.3 s, or from about 2.4 s to about 6.3 s, or from about 2.5 s to about 6.3 s, or from about 2.6 s to about 6.3 s, or from about 2.7 s to about 6.3 s, or from about 2.8 s to about 6.3 s, or from about 2.9 s to about 6.3 s, or from about 3.0 s to about 6.3 s, or from about 3.1 s to about 6.3 s, or from about 3.2 s to about 6.3 s, or from about 3.3 s to about 6.3 s, or from about 3.4 s to about 6.3 s, or from about 3.4 s to about 6.3 s, or from about 3.5 s to about 6.3 s, or from about 3.6 s to about 6.3 s, or from about 3.7 s to about 6.3 s, or from about 3.8 s to about 6.3 s, or from about 3.9 s to about 6.3 s, or from about 4.0 s to about 6.3 s, or from about 4.1 s to about 6.3 s, or from about 4.2 s to about 6.3 s, or from about 4.3 s to about 6.3 s, or from about 4.4 s to about 6.3 s, or from about 4.5 s to about 6.3 s, or from about 4.6 s to about 6.3 s, or from about 4.7 s to about 6.3 s, or from about 4.8 s to about 6.3 s, or from about 4.9 s to about 6.3 s, or from about 5.0 s to about 6.3 s, or from about 5.1 s to about 6.3 s, or from about 5.2 s to about 6.3 s, or from about 5.3 s to about 6.3 s, or from about 5.4 s to about 6.3 s, or from about 5.5 s to about 6.3 s, or from about 5.6 s to about 6.3 s, or from about 5.7 s to about 6.3 s, or from about 5.8 s to about 6.3 s, or from about 5.9 s to about 6.3 s, or from about 6.0 s to about 6.3 s, or from about 6.1 s to about 6.3 s, or from about 6.2 s to about 6.3 s, or from about 0.1 s to about 6.2 s, or from about 0.2 s to about 6.2 s, or from about 0.3 s to about 6.2 s, or from about 0.4 s to about 6.2 s, or from about 0.5 s to about 6.2 s, or from about 0.6 s to about 6.2 s, or from about 0.7 s to about 6.2 s, or from about 0.8 s to about 6.2 s, or from about 0.9 s to about 6.2 s, or from about 1.0 s to about 6.2 s, or from about 1.1 s to about 6.2 s, or from about 1.2 s to about 6.2 s, or from about 1.3 s to about 6.2 s, or from about 1.4 s to about 6.2 s, or from about 1.5 s to about 6.2 s, or from about 1.6 s to about 6.2 s, or from about 1.7 s to about 6.2 s, or from about 1.8 s to about 6.2 s, or from about 1.9 s to about 6.2 s, or from about 2.0 s to about 6.2 s, or from about 2.1 s to about 6.2 s, or from about 2.2 s to about 6.2 s, or from about 2.3 s to about 6.2 s, or from about 2.4 s to about 6.2 s, or from about 2.5 s to about 6.2 s, or from about 2.6 s to about 6.2 s, or from about 2.7 s to about 6.2 s, or from about 2.8 s to about 6.2 s, or from about 2.9 s to about 6.2 s, or from about 3.0 s to about 6.2 s, or from about 3.1 s to about 6.2 s, or from about 3.2 s to about 6.2 s, or from about 3.3 s to about 6.2 s, or from about 3.4 s to about 6.2 s, or from about 3.4 s to about 6.2 s, or from about 3.5 s to about 6.2 s, or from about 3.6 s to about 6.2 s, or from about 3.7 s to about 6.2 s, or from about 3.8 s to about 6.2 s, or from about 3.9 s to about 6.2 s, or from about 4.0 s to about 6.2 s, or from about 4.1 s to about 6.2 s, or from about 4.2 s to about 6.2 s, or from about 4.3 s to about 6.2 s, or from about 4.4 s to about 6.2 s, or from about 4.5 s to about 6.2 s, or from about 4.6 s to about 6.2 s, or from about 4.7 s to about 6.2 s, or from about 4.8 s to about 6.2 s, or from about 4.9 s to about 6.2 s, or from about 5.0 s to about 6.2 s, or from about 5.1 s to about 6.2 s, or from about 5.2 s to about 6.2 s, or from about 5.3 s to about 6.2 s, or from about 5.4 s to about 6.2 s, or from about 5.5 s to about 6.2 s, or from about 5.6 s to about 6.2 s, or from about 5.7 s to about 6.2 s, or from about 5.8 s to about 6.2 s, or from about 5.9 s to about 6.2 s, or from about 6.0 s to about 6.2 s, or from about 6.1 s to about 6.2 s, or from about 0.1 s to about 6.1 s, or from about 0.2 s to about 6.1 s, or from about 0.3 s to about 6.1 s, or from about 0.4 s to about 6.1 s, or from about 0.5 s to about 6.1 s, or from about 0.6 s to about 6.1 s, or from about 0.7 s to about 6.1 s, or from about 0.8 s to about 6.1 s, or from about 0.9 s to about 6.1 s, or from about 1.0 s to about 6.1 s, or from about 1.1 s to about 6.1 s, or from about 1.2 s to about 6.1 s, or from about 1.3 s to about 6.1 s, or from about 1.4 s to about 6.1 s, or from about 1.5 s to about 6.1 s, or from about 1.6 s to about 6.1 s, or from about 1.7 s to about 6.1 s, or from about 1.8 s to about 6.1 s, or from about 1.9 s to about 6.1 s, or from about 2.0 s to about 6.1 s, or from about 2.1 s to about 6.1 s, or from about 2.2 s to about 6.1 s, or from about 2.3 s to about 6.1 s, or from about 2.4 s to about 6.1 s, or from about 2.5 s to about 6.1 s, or from about 2.6 s to about 6.1 s, or from about 2.7 s to about 6.1 s, or from about 2.8 s to about 6.1 s, or from about 2.9 s to about 6.1 s, or from about 3.0 s to about 6.1 s, or from about 3.1 s to about 6.1 s, or from about 3.2 s to about 6.1 s, or from about 3.3 s to about 6.1 s, or from about 3.4 s to about 6.1 s, or from about 3.4 s to about 6.1 s, or from about 3.5 s to about 6.1 s, or from about 3.6 s to about 6.1 s, or from about 3.7 s to about 6.1 s, or from about 3.8 s to about 6.1 s, or from about 3.9 s to about 6.1 s, or from about 4.0 s to about 6.1 s, or from about 4.1 s to about 6.1 s, or from about 4.2 s to about 6.1 s, or from about 4.3 s to about 6.1 s, or from about 4.4 s to about 6.1 s, or from about 4.5 s to about 6.1 s, or from about 4.6 s to about 6.1 s, or from about 4.7 s to about 6.1 s, or from about 4.8 s to about 6.1 s, or from about 4.9 s to about 6.1 s, or from about 5.0 s to about 6.1 s, or from about 5.1 s to about 6.1 s, or from about 5.2 s to about 6.1 s, or from about 5.3 s to about 6.1 s, or from about 5.4 s to about 6.1 s, or from about 5.5 s to about 6.1 s, or from about 5.6 s to about 6.1 s, or from about 5.7 s to about 6.1 s, or from about 5.8 s to about 6.1 s, or from about 5.9 s to about 6.1 s, or from about 6.0 s to about 6.1 s, or from about 0.1 s to about 6.0 s, or from about 0.2 s to about 6.0 s, or from about 0.3 s to about 6.0 s, or from about 0.4 s to about 6.0 s, or from about 0.5 s to about 6.0 s, or from about 0.6 s to about 6.0 s, or from about 0.7 s to about 6.0 s, or from about 0.8 s to about 6.0 s, or from about 0.9 s to about 6.0 s, or from about 1.0 s to about 6.0 s, or from about 1.1 s to about 6.0 s, or from about 1.2 s to about 6.0 s, or from about 1.3 s to about 6.0 s, or from about 1.4 s to about 6.0 s, or from about 1.5 s to about 6.0 s, or from about 1.6 s to about 6.0 s, or from about 1.7 s to about 6.0 s, or from about 1.8 s to about 6.0 s, or from about 1.9 s to about 6.0 s, or from about 2.0 s to about 6.0 s, or from about 2.1 s to about 6.0 s, or from about 2.2 s to about 6.0 s, or from about 2.3 s to about 6.0 s, or from about 2.4 s to about 6.0 s, or from about 2.5 s to about 6.0 s, or from about 2.6 s to about 6.0 s, or from about 2.7 s to about 6.0 s, or from about 2.8 s to about 6.0 s, or from about 2.9 s to about 6.0 s, or from about 3.0 s to about 6.0 s, or from about 3.1 s to about 6.0 s, or from about 3.2 s to about 6.0 s, or from about 3.3 s to about 6.0 s, or from about 3.4 s to about 6.0 s, or from about 3.4 s to about 6.0 s, or from about 3.5 s to about 6.0 s, or from about 3.6 s to about 6.0 s, or from about 3.7 s to about 6.0 s, or from about 3.8 s to about 6.0 s, or from about 3.9 s to about 6.0 s, or from about 4.0 s to about 6.0 s, or from about 4.1 s to about 6.0 s, or from about 4.2 s to about 6.0 s, or from about 4.3 s to about 6.0 s, or from about 4.4 s to about 6.0 s, or from about 4.5 s to about 6.0 s, or from about 4.6 s to about 6.0 s, or from about 4.7 s to about 6.0 s, or from about 4.8 s to about 6.0 s, or from about 4.9 s to about 6.0 s, or from about 5.0 s to about 6.0 s, or from about 5.1 s to about 6.0 s, or from about 5.2 s to about 6.0 s, or from about 5.3 s to about 6.0 s, or from about 5.4 s to about 6.0 s, or from about 5.5 s to about 6.0 s, or from about 5.6 s to about 6.0 s, or from about 5.7 s to about 6.0 s, or from about 5.8 s to about 6.0 s, or from about 5.9 s to about 6.0 s, or from about 0.1 s to about 5.9 s, or from about 0.2 s to about 5.9 s, or from about 0.3 s to about 5.9 s, or from about 0.4 s to about 5.9 s, or from about 0.5 s to about 5.9 s, or from about 0.6 s to about 5.9 s, or from about 0.7 s to about 5.9 s, or from about 0.8 s to about 5.9 s, or from about 0.9 s to about 5.9 s, or from about 1.0 s to about 5.9 s, or from about 1.1 s to about 5.9 s, or from about 1.2 s to about 5.9 s, or from about 1.3 s to about 5.9 s, or from about 1.4 s to about 5.9 s, or from about 1.5 s to about 5.9 s, or from about 1.6 s to about 5.9 s, or from about 1.7 s to about 5.9 s, or from about 1.8 s to about 5.9 s, or from about 1.9 s to about 5.9 s, or from about 2.0 s to about 5.9 s, or from about 2.1 s to about 5.9 s, or from about 2.2 s to about 5.9 s, or from about 2.3 s to about 5.9 s, or from about 2.4 s to about 5.9 s, or from about 2.5 s to about 5.9 s, or from about 2.6 s to about 5.9 s, or from about 2.7 s to about 5.9 s, or from about 2.8 s to about 5.9 s, or from about 2.9 s to about 5.9 s, or from about 3.0 s to about 5.9 s, or from about 3.1 s to about 5.9 s, or from about 3.2 s to about 5.9 s, or from about 3.3 s to about 5.9 s, or from about 3.4 s to about 5.9 s, or from about 3.4 s to about 5.9 s, or from about 3.5 s to about 5.9 s, or from about 3.6 s to about 5.9 s, or from about 3.7 s to about 5.9 s, or from about 3.8 s to about 5.9 s, or from about 3.9 s to about 5.9 s, or from about 4.0 s to about 5.9 s, or from about 4.1 s to about 5.9 s, or from about 4.2 s to about 5.9 s, or from about 4.3 s to about 5.9 s, or from about 4.4 s to about 5.9 s, or from about 4.5 s to about 5.9 s, or from about 4.6 s to about 5.9 s, or from about 4.7 s to about 5.9 s, or from about 4.8 s to about 5.9 s, or from about 4.9 s to about 5.9 s, or from about 5.0 s to about 5.9 s, or from about 5.1 s to about 5.9 s, or from about 5.2 s to about 5.9 s, or from about 5.3 s to about 5.9 s, or from about 5.4 s to about 5.9 s, or from about 5.5 s to about 5.9 s, or from about 5.6 s to about 5.9 s, or from about 5.7 s to about 5.9 s, or from about 5.8 s to about 5.9 s, or from about 0.1 s to about 5.8 s, or from about 0.2 s to about 5.8 s, or from about 0.3 s to about 5.8 s, or from about 0.4 s to about 5.8 s, or from about 0.5 s to about 5.8 s, or from about 0.6 s to about 5.8 s, or from about 0.7 s to about 5.8 s, or from about 0.8 s to about 5.8 s, or from about 0.9 s to about 5.8 s, or from about 1.0 s to about 5.8 s, or from about 1.1 s to about 5.8 s, or from about 1.2 s to about 5.8 s, or from about 1.3 s to about 5.8 s, or from about 1.4 s to about 5.8 s, or from about 1.5 s to about 5.8 s, or from about 1.6 s to about 5.8 s, or from about 1.7 s to about 5.8 s, or from about 1.8 s to about 5.8 s, or from about 1.9 s to about 5.8 s, or from about 2.0 s to about 5.8 s, or from about 2.1 s to about 5.8 s, or from about 2.2 s to about 5.8 s, or from about 2.3 s to about 5.8 s, or from about 2.4 s to about 5.8 s, or from about 2.5 s to about 5.8 s, or from about 2.6 s to about 5.8 s, or from about 2.7 s to about 5.8 s, or from about 2.8 s to about 5.8 s, or from about 2.9 s to about 5.8 s, or from about 3.0 s to about 5.8 s, or from about 3.1 s to about 5.8 s, or from about 3.2 s to about 5.8 s, or from about 3.3 s to about 5.8 s, or from about 3.4 s to about 5.8 s, or from about 3.4 s to about 5.8 s, or from about 3.5 s to about 5.8 s, or from about 3.6 s to about 5.8 s, or from about 3.7 s to about 5.8 s, or from about 3.8 s to about 5.8 s, or from about 3.9 s to about 5.8 s, or from about 4.0 s to about 5.8 s, or from about 4.1 s to about 5.8 s, or from about 4.2 s to about 5.8 s, or from about 4.3 s to about 5.8 s, or from about 4.4 s to about 5.8 s, or from about 4.5 s to about 5.8 s, or from about 4.6 s to about 5.8 s, or from about 4.7 s to about 5.8 s, or from about 4.8 s to about 5.8 s, or from about 4.9 s to about 5.8 s, or from about 5.0 s to about 5.8 s, or from about 5.1 s to about 5.8 s, or from about 5.2 s to about 5.8 s, or from about 5.3 s to about 5.8 s, or from about 5.4 s to about 5.8 s, or from about 5.5 s to about 5.8 s, or from about 5.6 s to about 5.8 s, or from about 5.7 s to about 5.8 s, or from about 0.1 s to about 5.7 s, or from about 0.2 s to about 5.7 s, or from about 0.3 s to about 5.7 s, or from about 0.4 s to about 5.7 s, or from about 0.5 s to about 5.7 s, or from about 0.6 s to about 5.7 s, or from about 0.7 s to about 5.7 s, or from about 0.8 s to about 5.7 s, or from about 0.9 s to about 5.7 s, or from about 1.0 s to about 5.7 s, or from about 1.1 s to about 5.7 s, or from about 1.2 s to about 5.7 s, or from about 1.3 s to about 5.7 s, or from about 1.4 s to about 5.7 s, or from about 1.5 s to about 5.7 s, or from about 1.6 s to about 5.7 s, or from about 1.7 s to about 5.7 s, or from about 1.8 s to about 5.7 s, or from about 1.9 s to about 5.7 s, or from about 2.0 s to about 5.7 s, or from about 2.1 s to about 5.7 s, or from about 2.2 s to about 5.7 s, or from about 2.3 s to about 5.7 s, or from about 2.4 s to about 5.7 s, or from about 2.5 s to about 5.7 s, or from about 2.6 s to about 5.7 s, or from about 2.7 s to about 5.7 s, or from about 2.8 s to about 5.7 s, or from about 2.9 s to about 5.7 s, or from about 3.0 s to about 5.7 s, or from about 3.1 s to about 5.7 s, or from about 3.2 s to about 5.7 s, or from about 3.3 s to about 5.7 s, or from about 3.4 s to about 5.7 s, or from about 3.4 s to about 5.7 s, or from about 3.5 s to about 5.7 s, or from about 3.6 s to about 5.7 s, or from about 3.7 s to about 5.7 s, or from about 3.8 s to about 5.7 s, or from about 3.9 s to about 5.7 s, or from about 4.0 s to about 5.7 s, or from about 4.1 s to about 5.7 s, or from about 4.2 s to about 5.7 s, or from about 4.3 s to about 5.7 s, or from about 4.4 s to about 5.7 s, or from about 4.5 s to about 5.7 s, or from about 4.6 s to about 5.7 s, or from about 4.7 s to about 5.7 s, or from about 4.8 s to about 5.7 s, or from about 4.9 s to about 5.7 s, or from about 5.0 s to about 5.7 s, or from about 5.1 s to about 5.7 s, or from about 5.2 s to about 5.7 s, or from about 5.3 s to about 5.7 s, or from about 5.4 s to about 5.7 s, or from about 5.5 s to about 5.7 s, or from about 5.6 s to about 5.7 s, or from about 0.1 s to about 5.6 s, or from about 0.2 s to about 5.6 s, or from about 0.3 s to about 5.6 s, or from about 0.4 s to about 5.6 s, or from about 0.5 s to about 5.6 s, or from about 0.6 s to about 5.6 s, or from about 0.7 s to about 5.6 s, or from about 0.8 s to about 5.6 s, or from about 0.9 s to about 5.6 s, or from about 1.0 s to about 5.6 s, or from about 1.1 s to about 5.6 s, or from about 1.2 s to about 5.6 s, or from about 1.3 s to about 5.6 s, or from about 1.4 s to about 5.6 s, or from about 1.5 s to about 5.6 s, or from about 1.6 s to about 5.6 s, or from about 1.7 s to about 5.6 s, or from about 1.8 s to about 5.6 s, or from about 1.9 s to about 5.6 s, or from about 2.0 s to about 5.6 s, or from about 2.1 s to about 5.6 s, or from about 2.2 s to about 5.6 s, or from about 2.3 s to about 5.6 s, or from about 2.4 s to about 5.6 s, or from about 2.5 s to about 5.6 s, or from about 2.6 s to about 5.6 s, or from about 2.7 s to about 5.6 s, or from about 2.8 s to about 5.6 s, or from about 2.9 s to about 5.6 s, or from about 3.0 s to about 5.6 s, or from about 3.1 s to about 5.6 s, or from about 3.2 s to about 5.6 s, or from about 3.3 s to about 5.6 s, or from about 3.4 s to about 5.6 s, or from about 3.4 s to about 5.6 s, or from about 3.5 s to about 5.6 s, or from about 3.6 s to about 5.6 s, or from about 3.7 s to about 5.6 s, or from about 3.8 s to about 5.6 s, or from about 3.9 s to about 5.6 s, or from about 4.0 s to about 5.6 s, or from about 4.1 s to about 5.6 s, or from about 4.2 s to about 5.6 s, or from about 4.3 s to about 5.6 s, or from about 4.4 s to about 5.6 s, or from about 4.5 s to about 5.6 s, or from about 4.6 s to about 5.6 s, or from about 4.7 s to about 5.6 s, or from about 4.8 s to about 5.6 s, or from about 4.9 s to about 5.6 s, or from about 5.0 s to about 5.6 s, or from about 5.1 s to about 5.6 s, or from about 5.2 s to about 5.6 s, or from about 5.3 s to about 5.6 s, or from about 5.4 s to about 5.6 s, or from about 5.5 s to about 5.6 s, or from about 0.1 s to about 5.5 s, or from about 0.2 s to about 5.5 s, or from about 0.3 s to about 5.5 s, or from about 0.4 s to about 5.5 s, or from about 0.5 s to about 5.5 s, or from about 0.6 s to about 5.5 s, or from about 0.7 s to about 5.5 s, or from about 0.8 s to about 5.5 s, or from about 0.9 s to about 5.5 s, or from about 1.0 s to about 5.5 s, or from about 1.1 s to about 5.5 s, or from about 1.2 s to about 5.5 s, or from about 1.3 s to about 5.5 s, or from about 1.4 s to about 5.5 s, or from about 1.5 s to about 5.5 s, or from about 1.6 s to about 5.5 s, or from about 1.7 s to about 5.5 s, or from about 1.8 s to about 5.5 s, or from about 1.9 s to about 5.5 s, or from about 2.0 s to about 5.5 s, or from about 2.1 s to about 5.5 s, or from about 2.2 to about 5.5 s, or from about 2.3 s to about 5.5 s, or from about 2.4 s to about 5.5 s, or from about 2.5 s to about 5.5 s, or from about 2.6 s to about 5.5 s, or from about 2.7 s to about 5.5 s, or from about 2.8 s to about 5.5 s, or from about 2.9 s to about 5.5 s, or from about 3.0 s to about 5.5 s, or from about 3.1 s to about 5.5 s, or from about 3.2 s to about 5.5 s, or from about 3.3 s to about 5.5 s, or from about 3.4 to about 5.5 s, or from about 3.4 s to about 5.5 s, or from about 3.5 s to about 5.5 s, or from about 3.6 s to about 5.5 s, or from about 3.7 s to about 5.5 s, or from about 3.8 s to about 5.5 s, or from about 3.9 s to about 5.5 s, or from about 4.0 s to about 5.5 s, or from about 4.1 s to about 5.5 s, or from about 4.2 s to about 5.5 s, or from about 4.3 s to about 5.5 s, or from about 4.4 s to about 5.5 s, or from about 4.5 s to about 5.5 s, or from about 4.6 s to about 5.5 s, or from about 4.7 s to about 5.5 s, or from about 4.8 s to about 5.5 s, or from about 4.9 s to about 5.5 s, or from about 5.0 s to about 5.5 s, or from about 5.1 s to about 5.5 s, or from about 5.2 s to about 5.5 s, or from about 5.3 s to about 5.5 s, or from about 5.4 s to about 5.5 s, or from about 0.1 s to about 5.4 s, or from about 0.2 s to about 5.4 s, or from about 0.3 s to about 5.4 s, or from about 0.4 s to about 5.4 s, or from about 0.5 s to about 5.4 s, or from about 0.6 s to about 5.4 s, or from about 0.7 s to about 5.4 s, or from about 0.8 s to about 5.4 s, or from about 0.9 s to about 5.4 s, or from about 1.0 s to about 5.4 s, or from about 1.1 s to about 5.4 s, or from about 1.2 s to about 5.4 s, or from about 1.3 s to about 5.4 s, or from about 1.4 s to about 5.4 s, or from about 1.5 s to about 5.4 s, or from about 1.6 s to about 5.4 s, or from about 1.7 s to about 5.4 s, or from about 1.8 s to about 5.4 s, or from about 1.9 s to about 5.4 s, or from about 2.0 s to about 5.4 s, or from about 2.1 s to about 5.4 s, or from about 2.2 s to about 5.4 s, or from about 2.3 s to about 5.4 s, or from about 2.4 s to about 5.4 s, or from about 2.5 s to about 5.4 s, or from about 2.6 s to about 5.4 s, or from about 2.7 to about 5.4 s, or from about 2.8 s to about 5.4 s, or from about 2.9 s to about 5.4 s, or from about 3.0 s to about 5.4 s, or from about 3.1 s to about 5.4 s, or from about 3.2 s to about 5.4 s, or from about 3.3 s to about 5.4 s, or from about 3.4 s to about 5.4 s, or from about 3.4 s to about 5.4 s, or from about 3.5 s to, about 5.4 s, or from about 3.6 s to about 5.4 s, or from about 3.7 s to about 5.4 s, or from about 3.8 to about 5.4 s, or from about 3.9 s to about 5.4 s, or from about 4.0 s to about 5.4 s, or from about 4.1 s to about 5.4 s, or from about 4.2 s to about 5.4 s, or from about 4.3 s to about 5.4 s, or from about 4.4 s to about 5.4 s, or from about 4.5 s to about 5.4 s, or from about 4.6 s to about 5.4 s, or from about 4.7 s to about 5.4 s, or from about 4.8 s to about 5.4 s, or from about 4.9 s to about 5.4 s, or from about 5.0 s to about 5.4 s, or from about 5.1 s to about 5.4 s, or from about 5.2 s to about 5.4 s, or from about 5.3 s to about 5.4 s, or from about 0.1 s to about 5.3 s, or from about 0.2 s to about 5.3 s, or from about 0.3 s to about 5.3 s, or from about 0.4 s to about 5.3 s, or from about 0.5 s to about 5.3 s, or from about 0.6 s to about 5.3 s, or from about 0.7 s to about 5.3 s, or from about 0.8 s to about 5.3 s, or from about 0.9 s to about 5.3 s, or from about 1.0 s to about 5.3 s, or from about 1.1 s to about 5.3 s, or from about 1.2 s to about 5.3 s, or from about 1.3 s to about 5.3 s, or from about 1.4 s to about 5.3 s, or from about 1.5 s to about 5.3 s, or from about 1.6 s to about 5.3 s, or from about 1.7 s to about 5.3 s, or from about 1.8 s to about 5.3 s, or from about 1.9 s to about 5.3 s, or from about 2.0 s to about 5.3 s, or from about 2.1 s to about 5.3 s, or from about 2.2 s to about 5.3 s, or from about 2.3 s to about 5.3 s, or from about 2.4 s to about 5.3 s, or from about 2.5 s to about 5.3 s, or from about 2.6 s to about 5.3 s, or from about 2.7 s to about 5.3 s, or from about 2.8 s to about 5.3 s, or from about 2.9 s to about 5.3 s, or from about 3.0 s to about 5.3 s, or from about 3.1 s to about 5.3 s, or from about 3.2 s to about 5.3 s, or from about 3.3 s to about 5.3 s, or from about 3.4 s to about 5.3 s, or from about 3.4 s to about 5.3 s, or from about 3.5 s to about 5.3 s, or from about 3.6 s to about 5.3 s, or from about 3.7 s to about 5.3 s, or from about 3.8 s to about 5.3 s, or from about 3.9 s to about 5.3 s, or from about 4.0 s to about 5.3 s, or from about 4.1 s to about 5.3 s, or from about 4.2 s to about 5.3 s, or from about 4.3 s to about 5.3 s, or from about 4.4 s to about 5.3 s, or from about 4.5 s to about 5.3 s, or from about 4.6 s to about 5.3 s, or from about 4.7 s to about 5.3 s, or from about 4.8 s to about 5.3 s, or from about 4.9 s to about 5.3 s, or from about 5.0 s to about 5.3 s, or from about 5.1 s to about 5.3 s, or from about 5.2 s to about 5.3 s, or from about 0.1 s to about 5.2 s, or from about 0.2 s to about 5.2 s, or from about 0.3 s to about 5.2 s, or from about 0.4 s to about 5.2 s, or from about 0.5 s to about 5.2 s, or from about 0.6 s to about 5.2 s, or from about 0.7 s to about 5.2 s, or from about 0.8 s to about 5.2 s, or from about 0.9 s to about 5.2 s, or from about 1.0 s to about 5.2 s, or from about 1.1 s to about 5.2 s, or from about 1.2 s to about 5.2 s, or from about 1.3 s to about 5.2 s, or from about 1.4 s to about 5.2 s, or from about 1.5 s to about 5.2 s, or from about 1.6 s to about 5.2 s, or from about 1.7 s to about 5.2 s, or from about 1.8 s to about 5.2 s, or from about 1.9 s to about 5.2 s, or from about 2.0 s to about 5.2 s, or from about 2.1 s to about 5.2 s, or from about 2.2 s to about 5.2 s, or from about 2.3 s to about 5.2 s, or from about 2.4 s to about 5.2 s, or from about 2.5 s to about 5.2 s, or from about 2.6 s to about 5.2 s, or from about 2.7 s to about 5.2 s, or from about 2.8 s to about 5.2 s, or from about 2.9 s to about 5.2 s, or from about 3.0 s to about 5.2 s, or from about 3.1 s to about 5.2 s, or from about 3.2 s to about 5.2 s, or from about 3.3 s to about 5.2 s, or from about 3.4 s to about 5.2 s, or from about 3.4 s to about 5.2 s, or from about 3.5 s to about 5.2 s, or from about 3.6 s to about 5.2 s, or from about 3.7 s to about 5.2 s, or from about 3.8 s to about 5.2 s, or from about 3.9 s to about 5.2 s, or from about 4.0 s to about 5.2 s, or from about 4.1 s to about 5.2 s, or from about 4.2 s to about 5.2 s, or from about 4.3 s to about 5.2 s, or from about 4.4 s to about 5.2 s, or from about 4.5 s to about 5.2 s, or from about 4.6 s to about 5.2 s, or from about 4.7 s to about 5.2 s, or from about 4.8 s to about 5.2 s, or from about 4.9 s to about 5.2 s, or from about 5.0 s to about 5.2 s, or from about 5.1 s to about 5.2 s, or from about 0.1 s to about 5.1 s, or from about 0.2 s to about 5.1 s, or from about 0.3 s to about 5.1 s, or from about 0.4 s to about 5.1 s, or from about 0.5 s to about 5.1 s, or from about 0.6 s to about 5.1 s, or from about 0.7 s to about 5.1 s, or from about 0.8 s to about 5.1 s, or from about 0.9 s to about 5.1 s, or from about 1.0 s to about 5.1 s, or from about 1.1 s to about 5.1 s, or from about 1.2 s to about 5.1 s, or from about 1.3 s to about 5.1 s, or from about 1.4 s to about 5.1 s, or from about 1.5 s to about 5.1 s, or from about 1.6 s to about 5.1 s, or from about 1.7 s to about 5.1 s, or from about 1.8 s to about 5.1 s, or from about 1.9 s to about 5.1 s, or from about 2.0 s to about 5.1 s, or from about 2.1 s to about 5.1 s, or from about 2.2 s to about 5.1 s, or from about 2.3 s to about 5.1 s, or from about 2.4 s to about 5.1 s, or from about 2.5 s to about 5.1 s, or from about 2.6 s to about 5.1 s, or from about 2.7 s to about 5.1 s, or from about 2.8 s to about 5.1 s, or from about 2.9 s to about 5.1 s, or from about 3.0 s to about 5.1 s, or from about 3.1 s to about 5.1 s, or from about 3.2 s to about 5.1 s, or from about 3.3 s to about 5.1 s, or from about 3.4 s to about 5.1 s, or from about 3.4 s to about 5.1 s, or from about 3.5 s to about 5.1 s, or from about 3.6 s to about 5.1 s, or from about 3.7 s to about 5.1 s, or from about 3.8 s to about 5.1 s, or from about 3.9 s to about 5.1 s, or from about 4.0 s to about 5.1 s, or from about 4.1 s to about 5.1 s, or from about 4.2 s to about 5.1 s, or from about 4.3 s to about 5.1 s, or from about 4.4 s to about 5.1 s, or from about 4.5 s to about 5.1 s, or from about 4.6 s to about 5.1 s, or from about 4.7 s to about 5.1 s, or from about 4.8 s to about 5.1 s, or from about 4.9 s to about 5.1 s, or from about 5.0 s to about 5.1 s, or from about 0.1 s to about 5.0 s, or from about 0.2 s to about 5.0 s, or from about 0.3 s to about 5.0 s, or from about 0.4 s to about 5.0 s, or from about 0.5 s to about 5.0 s, or from about 0.6 s to about 5.0 s, or from about 0.7 s to about 5.0 s, or from about 0.8 s to about 5.0 s, or from about 0.9 s to about 5.0 s, or from about 1.0 s to about 5.0 s, or from about 1.1 s to about 5.0 s, or from about 1.2 s to about 5.0 s, or from about 1.3 s to about 5.0 s, or from about 1.4 s to about 5.0 s, or from about 1.5 s to about 5.0 s, or from about 1.6 s to about 5.0 s, or from about 1.7 s to about 5.0 s, or from about 1.8 s to about 5.0 s, or from about 1.9 s to about 5.0 s, or from about 2.0 s to about 5.0 s, or from about 2.1 s to about 5.0 s, or from about 2.2 s to about 5.0 s, or from about 2.3 s to about 5.0 s, or from about 2.4 s to about 5.0 s, or from about 2.5 s to about 5.0 s, or from about 2.6 s to about 5.0 s, or from about 2.7 s to about 5.0 s, or from about 2.8 s to about 5.0 s, or from about 2.9 s to about 5.0 s, or from about 3.0 s to about 5.0 s, or from about 3.1 s to about 5.0 s, or from about 3.2 s to about 5.0 s, or from about 3.3 s to about 5.0 s, or from about 3.4 s to about 5.0 s, or from about 3.4 s to about 5.0 s, or from about 3.5 s to about 5.0 s, or from about 3.6 s to about 5.0 s, or from about 3.7 s to about 5.0 s, or from about 3.8 s to about 5.0 s, or from about 3.9 s to about 5.0 s, or from about 4.0 s to about 5.0 s, or from about 4.1 s to about 5.0 s, or from about 4.2 s to about 5.0 s, or from about 4.3 s to about 5.0 s, or from about 4.4 s to about 5.0 s, or from about 4.5 s to about 5.0 s, or from about 4.6 s to about 5.0 s, or from about 4.7 s to about 5.0 s, or from about 4.8 s to about 5.0 s, or from about 4.9 s to about 5.0 s, or from about 0.1 s to about 4.9 s, or from about 0.2 s to about 4.9 s, or from about 0.3 s to about 4.9 s, or from about 0.4 s to about 4.9 s, or from about 0.5 s to about 4.9 s, or from about 0.6 s to about 4.9 s, or from about 0.7 s to about 4.9 s, or from about 0.8 s to about 4.9 s, or from about 0.9 s to about 4.9 s, or from about 1.0 s to about 4.9 s, or from about 1.1 s to about 4.9 s, or from about 1.2 s to about 4.9 s, or from about 1.3 s to about 4.9 s, or from about 1.4 s to about 4.9 s, or from about 1.5 s to about 4.9 s, or from about 1.6 s to about 4.9 s, or from about 1.7 s to about 4.9 s, or from about 1.8 s to about 4.9 s, or from about 1.9 s to about 4.9 s, or from about 2.0 s to about 4.9 s, or from about 2.1 s to about 4.9 s, or from about 2.2 s to about 4.9 s, or from about 2.3 s to about 4.9 s, or from about 2.4 s to about 4.9 s, or from about 2.5 s to about 4.9 s, or from about 2.6 s to about 4.9 s, or from about 2.7 s to about 4.9 s, or from about 2.8 s to about 4.9 s, or from about 2.9 s to about 4.9 s, or from about 3.0 s to about 4.9 s, or from about 3.1 s to about 4.9 s, or from about 3.2 s to about 4.9 s, or from about 3.3 s to about 4.9 s, or from about 3.4 s to about 4.9 s, or from about 3.4 s to about 4.9 s, or from about 3.5 s to about 4.9 s, or from about 3.6 s to about 4.9 s, or from about 3.7 s to about 4.9 s, or from about 3.8 s to about 4.9 s, or from about 3.9 s to about 4.9 s, or from about 4.0 s to about 4.9 s, or from about 4.1 s to about 4.9 s, or from about 4.2 s to about 4.9 s, or from about 4.3 s to about 4.9 s, or from about 4.4 s to about 4.9 s, or from about 4.5 s to about 4.9 s, or from about 4.6 s to about 4.9 s, or from about 4.7 s to about 4.9 s, or from about 4.8 s to about 4.9 s, or from about 0.1 s to about 4.8 s, or from about 0.2 s to about 4.8 s, or from about 0.3 s to about 4.8 s, or from about 0.4 s to about 4.8 s, or from about 0.5 s to about 4.8 s, or from about 0.6 s to about 4.8 s, or from about 0.7 s to about 4.8 s, or from about 0.8 s to about 4.8 s, or from about 0.9 s to about 4.8 s, or from about 1.0 s to about 4.8 s, or from about 1.1 s to about 4.8 s, or from about 1.2 s to about 4.8 s, or from about 1.3 s to about 4.8 s, or from about 1.4 s to about 4.8 s, or from about 1.5 s to about 4.8 s, or from about 1.6 s to about 4.8 s, or from about 1.7 s to about 4.8 s, or from about 1.8 s to about 4.8 s, or from about 1.9 s to about 4.8 s, or from about 2.0 s to about 4.8 s, or from about 2.1 s to about 4.8 s, or from about 2.2 s to about 4.8 s, or from about 2.3 s to about 4.8 s, or from about 2.4 s to about 4.8 s, or from about 2.5 s to about 4.8 s, or from about 2.6 s to about 4.8 s, or from about 2.7 s to about 4.8 s, or from about 2.8 s to about 4.8 s, or from about 2.9 s to about 4.8 s, or from about 3.0 s to about 4.8 s, or from about 3.1 s to about 4.8 s, or from about 3.2 s to about 4.8 s, or from about 3.3 s to about 4.8 s, or from about 3.4 s to about 4.8 s, or from about 3.4 s to about 4.8 s, or from about 3.5 s to about 4.8 s, or from about 3.6 s to about 4.8 s, or from about 3.7 s to about 4.8 s, or from about 3.8 s to about 4.8 s, or from about 3.9 s to about 4.8 s, or from about 4.0 s to about 4.8 s, or from about 4.1 s to about 4.8 s, or from about 4.2 s to about 4.8 s, or from about 4.3 s to about 4.8 s, or from about 4.4 s to about 4.8 s, or from about 4.5 s to about 4.8 s, or from about 4.6 s to about 4.8 s, or from about 4.7 s to about 4.8 s, or from about 0.1 s to about 4.7 s, or from about 0.2 s to about 4.7 s, or from about 0.3 s to about 4.7 s, or from about 0.4 s to about 4.7 s, or from about 0.5 s to about 4.7 s, or from about 0.6 s to about 4.7 s, or from about 0.7 s to about 4.7 s, or from about 0.8 s to about 4.7 s, or from about 0.9 s to about 4.7 s, or from about 1.0 s to about 4.7 s, or from about 1.1 s to about 4.7 s, or from about 1.2 s to about 4.7 s, or from about 1.3 s to about 4.7 s, or from about 1.4 s to about 4.7 s, or from about 1.5 s to about 4.7 s, or from about 1.6 s to about 4.7 s, or from about 1.7 s to about 4.7 s, or from about 1.8 s to about 4.7 s, or from about 1.9 s to about 4.7 s, or from about 2.0 s to about 4.7 s, or from about 2.1 s to about 4.7 s, or from about 2.2 s to about 4.7 s, or from about 2.3 s to about 4.7 s, or from about 2.4 s to about 4.7 s, or from about 2.5 s to about 4.7 s, or from about 2.6 s to about 4.7 s, or from about 2.7 s to about 4.7 s, or from about 2.8 s to about 4.7 s, or from about 2.9 s to about 4.7 s, or from about 3.0 s to about 4.7 s, or from about 3.1 s to about 4.7 s, or from about 3.2 s to about 4.7 s, or from about 3.3 s to about 4.7 s, or from about 3.4 s to about 4.7 s, or from about 3.4 s to about 4.7 s, or from about 3.5 s to about 4.7 s, or from about 3.6 s to about 4.7 s, or from about 3.7 s to about 4.7 s, or from about 3.8 s to about 4.7 s, or from about 3.9 s to about 4.7 s, or from about 4.0 s to about 4.7 s, or from about 4.1 s to about 4.7 s, or from about 4.2 s to about 4.7 s, or from about 4.3 s to about 4.7 s, or from about 4.4 s to about 4.7 s, or from about 4.5 s to about 4.7 s, or from about 4.6 s to about 4.7 s, or from about 0.1 s to about 4.6 s, or from about 0.2 s to about 4.6 s, or from about 0.3 s to about 4.6 s, or from about 0.4 s to about 4.6 s, or from about 0.5 s to about 4.6 s, or from about 0.6 s to about 4.6 s, or from about 0.7 s to about 4.6 s, or from about 0.8 s to about 4.6 s, or from about 0.9 s to about 4.6 s, or from about 1.0 s to about 4.6 s, or from about 1.1 s to about 4.6 s, or from about 1.2 s to about 4.6 s, or from about 1.3 s to about 4.6 s, or from about 1.4 s to about 4.6 s, or from about 1.5 s to about 4.6 s, or from about 1.6 s to about 4.6 s, or from about 1.7 s to about 4.6 s, or from about 1.8 s to about 4.6 s, or from about 1.9 s to about 4.6 s, or from about 2.0 s to about 4.6 s, or from about 2.1 s to about 4.6 s, or from about 2.2 s to about 4.6 s, or from about 2.3 s to about 4.6 s, or from about 2.4 s to about 4.6 s, or from about 2.5 s to about 4.6 s, or from about 2.6 s to about 4.6 s, or from about 2.7 s to about 4.6 s, or from about 2.8 s to about 4.6 s, or from about 2.9 s to about 4.6 s, or from about 3.0 s to about 4.6 s, or from about 3.1 s to about 4.6 s, or from about 3.2 s to about 4.6 s, or from about 3.3 s to about 4.6 s, or from about 3.4 s to about 4.6 s, or from about 3.4 s to about 4.6 s, or from about 3.5 s to about 4.6 s, or from about 3.6 s to about 4.6 s, or from about 3.7 s to about 4.6 s, or from about 3.8 s to about 4.6 s, or from about 3.9 s to about 4.6 s, or from about 4.0 s to about 4.6 s, or from about 4.1 s to about 4.6 s, or from about 4.2 s to about 4.6 s, or from about 4.3 s to about 4.6 s, or from about 4.4 s to about 4.6 s, or from about 4.5 s to about 4.6 s, or from about 0.1 s to about 4.5 s, or from about 0.2 s to about 4.5 s, or from about 0.3 s to about 4.5 s, or from about 0.4 s to about 4.5 s, or from about 0.5 s to about 4.5 s, or from about 0.6 s to about 4.5 s, or from about 0.7 s to about 4.5 s, or from about 0.8 s to about 4.5 s, or from about 0.9 s to about 4.5 s, or from about 1.0 s to about 4.5 s, or from about 1.1 s to about 4.5 s, or from about 1.2 s to about 4.5 s, or from about 1.3 s to about 4.5 s, or from about 1.4 s to about 4.5 s, or from about 1.5 s to about 4.5 s, or from about 1.6 s to about 4.5 s, or from about 1.7 s to about 4.5 s, or from about 1.8 s to about 4.5 s, or from about 1.9 s to about 4.5 s, or from about 2.0 s to about 4.5 s, or from about 2.1 s to about 4.5 s, or from about 2.2 s to about 4.5 s, or from about 2.3 s to about 4.5 s, or from about 2.4 s to about 4.5 s, or from about 2.5 s to about 4.5 s, or from about 2.6 s to about 4.5 s, or from about 2.7 s to about 4.5 s, or from about 2.8 s to about 4.5 s, or from about 2.9 s to about 4.5 s, or from about 3.0 s to about 4.5 s, or from about 3.1 s to about 4.5 s, or from about 3.2 s to about 4.5 s, or from about 3.3 s to about 4.5 s, or from about 3.4 s to about 4.5 s, or from about 3.4 s to about 4.5 s, or from about 3.5 s to about 4.5 s, or from about 3.6 s to about 4.5 s, or from about 3.7 s to about 4.5 s, or from about 3.8 s to about 4.5 s, or from about 3.9 s to about 4.5 s, or from about 4.0 s to about 4.5 s, or from about 4.1 s to about 4.5 s, or from about 4.2 s to about 4.5 s, or from about 4.3 s to about 4.5 s, or from about 4.4 s to about 4.5 s, or from about 0.1 s to about 4.4 s, or from about 0.2 s to about 4.4 s, or from about 0.3 s to about 4.4 s, or from about 0.4 s to about 4.4 s, or from about 0.5 s to about 4.4 s, or from about 0.6 s to about 4.4 s, or from about 0.7 s to about 4.4 s, or from about 0.8 s to about 4.4 s, or from about 0.9 s to about 4.4 s, or from about 1.0 s to about 4.4 s, or from about 1.1 s to about 4.4 s, or from about 1.2 s to about 4.4 s, or from about 1.3 s to about 4.4 s, or from about 1.4 s to about 4.4 s, or from about 1.5 s to about 4.4 s, or from about 1.6 s to about 4.4 s, or from about 1.7 s to about 4.4 s, or from about 1.8 s to about 4.4 s, or from about 1.9 s to about 4.4 s, or from about 2.0 s to about 4.4 s, or from about 2.1 s to about 4.4 s, or from about 2.2 s to about 4.4 s, or from about 2.3 s to about 4.4 s, or from about 2.4 s to about 4.4 s, or from about 2.5 s to about 4.4 s, or from about 2.6 s to about 4.4 s, or from about 2.7 s to about 4.4 s, or from about 2.8 s to about 4.4 s, or from about 2.9 s to about 4.4 s, or from about 3.0 s to about 4.4 s, or from about 3.1 s to about 4.4 s, or from about 3.2 s to about 4.4 s, or from about 3.3 s to about 4.4 s, or from about 3.4 s to about 4.4 s, or from about 3.4 s to about 4.4 s, or from about 3.5 s to about 4.4 s, or from about 3.6 s to about 4.4 s, or from about 3.7 s to about 4.4 s, or from about 3.8 s to about 4.4 s, or from about 3.9 s to about 4.4 s, or from about 4.0 s to about 4.4 s, or from about 4.1 s to about 4.4 s, or from about 4.2 s to about 4.4 s, or from about 4.3 s to about 4.4 s, or from about 0.1 s to about 4.3 s, or from about 0.2 s to about 4.3 s, or from about 0.3 s to about 4.3 s, or from about 0.4 s to about 4.3 s, or from about 0.5 s to about 4.3 s, or from about 0.6 s to about 4.3 s, or from about 0.7 s to about 4.3 s, or from about 0.8 s to about 4.3 s, or from about 0.9 s to about 4.3 s, or from about 1.0 s to about 4.3 s, or from about 1.1 s to about 4.3 s, or from about 1.2 s to about 4.3 s, or from about 1.3 s to about 4.3 s, or from about 1.4 s to about 4.3 s, or from about 1.5 s to about 4.3 s, or from about 1.6 s to about 4.3 s, or from about 1.7 s to about 4.3 s, or from about 1.8 s to about 4.3 s, or from about 1.9 s to about 4.3 s, or from about 2.0 s to about 4.3 s, or from about 2.1 s to about 4.3 s, or from about 2.2 s to about 4.3 s, or from about 2.3 s to about 4.3 s, or from about 2.4 s to about 4.3 s, or from about 2.5 s to about 4.3 s, or from about 2.6 s to about 4.3 s, or from about 2.7 s to about 4.3 s, or from about 2.8 s to about 4.3 s, or from about 2.9 s to about 4.3 s, or from about 3.0 s to about 4.3 s, or from about 3.1 s to about 4.3 s, or from about 3.2 s to about 4.3 s, or from about 3.3 s to about 4.3 s, or from about 3.4 s to about 4.3 s, or from about 3.4 s to about 4.3 s, or from about 3.5 s to about 4.3 s, or from about 3.6 s to about 4.3 s, or from about 3.7 s to about 4.3 s, or from about 3.8 s to about 4.3 s, or from about 3.9 s to about 4.3 s, or from about 4.0 s to about 4.3 s, or from about 4.1 s to about 4.3 s, or from about 4.2 s to about 4.3 s, or from about 0.1 s to about 4.2 s, or from about 0.2 s to about 4.2 s, or from about 0.3 s to about 4.2 s, or from about 0.4 s to about 4.2 s, or from about 0.5 s to about 4.2 s, or from about 0.6 s to about 4.2 s, or from about 0.7 s to about 4.2 s, or from about 0.8 s to about 4.2 s, or from about 0.9 s to about 4.2 s, or from about 1.0 s to about 4.2 s, or from about 1.1 s to about 4.2 s, or from about 1.2 s to about 4.2 s, or from about 1.3 s to about 4.2 s, or from about 1.4 s to about 4.2 s; from about 1.5 s to about 4.2 s, or from about 1.6 s to about 4.2 s, or from about 1.7 s to about 4.2 s, or from about 1.8 s to about 4.2 s, or from about 1.9 s to about 4.2 s, or from about 2.0 s to about 4.2 s, or from about 2.1 s to about 4.2 s, or from about 2.2 s to about 4.2 s, or from about 2.3 s to about 4.2 s, or from about 2.4 s to about 4.2 s, or from about 2.5 s to about 4.2 s, or from about 2.6 s to about 4.2 s, or from about 2.7 s to about 4.2 s, or from about 2.8 s to about 4.2 s, or from about 2.9 s to about 4.2 s, or from about 3.0 s to about 4.2 s, or from about 3.1 s to about 4.2 s, or from about 3.2 s to about 4.2 s, or from about 3.3 s to about 4.2 s, or from about 3.4 s to about 4.2 s, or from about 3.4 s to about 4.2 s, or from about 3.5 s to about 4.2 s, or from about 3.6 s to about 4.2 s, or from about 3.7 s to about 4.2 s, or from about 3.8 s to about 4.2 s, or from about 3.9 s to about 4.2 s, or from about 4.0 s to about 4.2 s, or from about 4.1 s to about 4.2 s, or from about 0.1 s to about 4.1 s, or from about 0.2 s to about 4.1 s, or from about 0.3 s to about 4.1 s, or from about 0.4 s to about 4.1 s, or from about 0.5 s to about 4.1 s, or from about 0.6 s to about 4.1 s, or from about 0.7 s to about 4.1 s, or from about 0.8 s to about 4.1 s, or from about 0.9 s to about 4.1 s, or from about 1.0 s to about 4.1 s, or from about 1.1 s to about 4.1 s, or from about 1.2 s to about 4.1 s, or from about 1.3 s to about 4.1 s, or from about 1.4 s to about 4.1 s, or from about 1.5 s to about 4.1 s, or from about 1.6 s to about 4.1 s, or from about 1.7 s to about 4.1 s, or from about 1.8 s to about 4.1 s, or from about 1.9 s to about 4.1 s, or from about 2.0 s to about 4.1 s, or from about 2.1 s to about 4.1 s, or from about 2.2 s to about 4.1 s, or from about 2.3 s to about 4.1 s, or from about 2.4 s to about 4.1 s, or from about 2.5 s to about 4.1 s, or from about 2.6 s to about 4.1 s, or from about 2.7 s to about 4.1 s, or from about 2.8 s to about 4.1 s, or from about 2.9 s to about 4.1 s, or from about 3.0 s to about 4.1 s, or from about 3.1 s to about 4.1 s, or from about 3.2 s to about 4.1 s, or from about 3.3 s to about 4.1 s, or from about 3.4 s to about 4.1 s, or from about 3.4 s to about 4.1 s, or from about 3.5 s to about 4.1 s, or from about 3.6 s to about 4.1 s, or from about 3.7 s to about 4.1 s, or from about 3.8 s to about 4.1 s, or from about 3.9 s to about 4.1 s, or from about 4.0 s to about 4.1 s, or from about 0.1 s to about 4.0 s, or from about 0.2 s to about 4.0 s, or from about 0.3 s to about 4.0 s, or from about 0.4 s to about 4.0 s, or from about 0.5 s to about 4.0 s, or from about 0.6 s to about 4.0 s, or from about 0.7 s to about 4.0 s, or from about 0.8 s to about 4.0 s, or from about 0.9 s to about 4.0 s, or from about 1.0 s to about 4.0 s, or from about 1.1 s to about 4.0 s, or from about 1.2 s to about 4.0 s, or from about 1.3 s to about 4.0 s, or from about 1.4 s to about 4.0 s, or from about 1.5 s to about 4.0 s, or from about 1.6 s to about 4.0 s, or from about 1.7 s to about 4.0 s, or from about 1.8 s to about 4.0 s, or from about 1.9 s to about 4.0 s, or from about 2.0 s to about 4.0 s, or from about 2.1 s to about 4.0 s, or from about 2.2 s to about 4.0 s, or from about 2.3 s to about 4.0 s, or from about 2.4 s to about 4.0 s, or from about 2.5 s to about 4.0 s, or from about 2.6 s to about 4.0 s, or from about 2.7 s to about 4.0 s, or from about 2.8 s to about 4.0 s, or from about 2.9 s to about 4.0 s, or from about 3.0 s to about 4.0 s, or from about 3.1 s to about 4.0 s, or from about 3.2 s to, about 4.0 s, or from about 3.3 s to about 4.0 s, or from about 3.4 s to about 4.0 s, or from about 3.4 s to about 4.0 s, or from about 3.5 s to about 4.0 s, or from about 3.6 s to about 4.0 s, or from about 3.7 s to about 4.0 s, or from about 3.8 s to about 4.0 s, or from about 3.9 s to about 4.0 s, or from about 0.1 s to about 3.9 s, or from about 0.2 s to about 3.9 s, or from about 0.3 s to about 3.9 s, or from about 0.4 s to about 3.9 s, or from about 0.5 s to about 3.9 s, or from about 0.6 s to about 3.9 s, or from about 0.7 s to about 3.9 s, or from about 0.8 s to about 3.9 s, or from about 0.9 s to about 3.9 s, or from about 1.0 s to about 3.9 s, or from about 1.1 s to about 3.9 s, or from about 1.2 s to about 3.9 s, or from about 1.3 s to about 3.9 s, or from about 1.4 s to about 3.9 s, or from about 1.5 s to about 3.9 s, or from about 1.6 s to about 3.9 s, or from about 1.7 s to about 3.9 s, or from about 1.8 s to about 3.9 s, or from about 1.9 s to about 3.9 s, or from about 2.0 s to about 3.9 s, or from about 2.1 s to about 3.9 s, or from about 2.2 s to about 3.9 s, or from about 2.3 s to about 3.9 s, or from about 2.4 s to about 3.9 s, or from about 2.5 s to about 3.9 s, or from about 2.6 s to about 3.9 s, or from about 2.7 s to about 3.9 s, or from about 2.8 s to about 3.9 s, or from about 2.9 s to about 3.9 s, or from about 3.0 s to about 3.9 s, or from about 3.1 s to about 3.9 s, or from about 3.2 s to about 3.9 s, or from about 3.3 s to about 3.9 s, or from about 3.4 s to about 3.9 s, or from about 3.4 s to about 3.9 s, or from about 3.5 s to about 3.9 s, or from about 3.7 s to about 3.9 s, or from about 3.8 s to about 3.9 s, or from about 0.1 s to about 3.8 s, or from about 0.2 s to about 3.8 s, or from about 0.3 s to about 3.8 s, or from about 0.4 s to about 3.8 s, or from about 0.5 s to about 3.8 s, or from about 0.6 s to about 3.8 s, or from about 0.7 s to about 3.8 s, or from about 0.8 s to about 3.8 s, or from about 0.9 s to about 3.8 s, or from about 1.0 s to about 3.8 s, or from about 1.1 s to about 3.8 s, or from about 1.2 s to about 3.8 s, or from about 1.3 s to about 3.8 s, or from about 1.4 s to about 3.8 s, or from about 1.5 s to about 3.8 s, or from about 1.6 s to about 3.8 s, or from about 1.7 s to about 3.8 s, or from about 1.8 s to about 3.8 s, or from about 1.9 s to about 3.8 s, or from about 2.0 s to about 3.8 s, or from about 2.1 s to about 3.8 s, or from about 2.2 s to about 3.8 s, or from about 2.3 s to about 3.8 s, or from about 2.4 s to about 3.8 s, or from about 2.5 s to about 3.8 s, or from about 2.6 s to about 3.8 s, or from about 2.7 s to about 3.8 s, or from about 2.1 s to about 3.8 s, or from about 2.9 s to about 3.8 s, or from about 3.0 s to about 3.8 s, or from about 3.1 s to about 3.8 s, or from about 3.2 s to about 3.8 s, or from about 3.3 s to about 3.8 s, or from about 3.4 s to about 3.8 s, or from about 3.4 s to about 3.8 s, or from about 3.5 s to about 3.8 s, or from about 3.6 s to about 3.8 s, or from about 3.7 s to about 3.8 s, or from about 0.1 s to about 3.7 s, or from about 0.2 s to about 3.7 s, or from about 0.3 s to about 3.7 s, or from about 0.4 s to about 3.7 s, or from about 0.5 s to about 3.7 s, or from about 0.6 s to about 3.7 s, or from about 0.7 s to about 3.7 s, or from about 0.8 s to about 3.7 s, or from about 0.9 s to about 3.7 s, or from about 1.0 s to about 3.7 s, or from about 1.1 s to about 3.7 s, or from about 1.2 s to about 3.7 s, or from about 1.3 s to about 3.7 s, or from about 1.4 s to about 3.7 s, or from about 1.5 s to about 3.7 s, or from about 1.6 s to about 3.7 s, or from about 1.7 s to about 3.7 s, or from about 1.8 s to about 3.7 s, or from about 1.9 s to about 3.7 s, or from about 2.0 s to about 3.7 s, or from about 2.1 s to about 3.7 s, or from about 2.2 s to about 3.7 s, or from about 2.3 s to about 3.7 s, or from about 2.4 s to about 3.7 s, or from about 2.5 s to about 3.7 s, or from about 2.6 s to about 3.7 s, or from about 2.7 s to about 3.7 s, or from about 2.8 s to about 3.7 s, or from about 2.9 s to about 3.7 s, or from about 3.0 s to about 3.7 s, or from about 3.1 s to about 3.7 s, or from about 3.2 s to about 3.7 s, or from about 3.3 s to about 3.7 s, or from about 3.4 s to about 3.7 s, or from about 3.4 s to about 3.7 s, or from about 3.5 s to about 3.7 s, or from about 3.6 s to about 3.7 s, or from about 0.1 s to about 3.6 s, or from about 0.2 s to about 3.6 s, or from about 0.3 s to about 3.6 s, or from about 0.4 s to about 3.6 s, or from about 0.5 s to about 3.6 s, or from about 0.6 s to about 3.6 s, or from about 0.7 s to about 3.6 s, or from about 0.8 s to about 3.6 s, or from about 0.9 s to about 3.6 s, or from about 1.0 s to about 3.6 s, or from about 1.1 s to about 3.6 s, or from about 1.2 s to about 3.6 s, or from about 1.3 s to about 3.6 s, or from about 1.4 s to about 3.6 s, or from about 1.5 s to about 3.6 s, or from about 1.6 s to about 3.6 s, or from about 1.7 s to about 3.6 s, or from about 1.8 s to about 3.6 s, or from about 1.9 s to about 3.6 s, or from about 2.0 s to about 3.6 s, or from about 2.1 s to about 3.6 s, or from about 2.2 s to about 3.6 s, or from about 2.3 s to about 3.6 s, or from about 2.4 s to about 3.6 s, or from about 2.5 s to about 3.6 s, or from about 2.6 s to about 3.6 s, or from about 2.7 s to about 3.6 s, or from about 2.8 s to about 3.6 s, or from about 2.9 s to about 3.6 s, or from about 3.0 s to about 3.6 s, or from about 3.1 s to about 3.6 s, or from about 3.2 s to about 3.6 s, or from about 3.3 s to about 3.6 s, or from about 3.4 s to about 3.6 s, or from about 3.4 s to about 3.6 s, or from about 3.5 s to about 3.6 s, or from about 0.1 s to about 3.5 s, or from about 0.2 s to about 3.5 s, or from about 0.3 s to about 3.5 s, or from about 0.4 s to about 3.5 s, or from about 0.5 s to about 3.5 s, or from about 0.6 s to about 3.5 s, or from about 0.7 s to about 3.5 s, or from about 0.8 s to about 3.5 s, or from about 0.9 s to about 3.5 s, or from about 1.0 s to about 3.5 s, or from about 1.1 s to about 3.5 s, or from about 1.2 to about 3.5 s, or from about 1.3 s to about 3.5 s, or from about 1.4 s to about 3.5 s, or from about 1.5 s to about 3.5 s, or from about 1.6 s to about 3.5 s, or from about 1.7 s to about 3.5 s, or from about 1.8 s to about 3.5 s, or from about 1.9 s to about 3.5 s, or from about 2.0 s to about 3.5 s, or from about 2.1 s to about 3.5 s, or from about 2.2 s to about 3.5 s, or from about 2.3 s to about 3.5 s, or from about 2.4 s to about 3.5 s, or from about 2.5 s to about 3.5 s, or from about 2.6 s to about 3.5 s, or from about 2.7 s to about 3.5 s, or from about 2.8 s to about 3.5 s, or from about 2.9 s to about 3.5 s, or from about 3.0 s to about 3.5 s, or from about 3.1 s to about 3.5 s, or from about 3.2 s to about 3.5 s, or from about 3.3 s to about 3.5 s, or from about 3.4 s to about 3.5 s, or from about 3.4 s to about 3.5 s, or from about 0.1 s to about 3.4 s, or from about 0.2 s to about 3.4 s, or from about 0.3 s to about 3.4 s, or from about 0.4 s to about 3.4 s, or from about 0.5 s to about 3.4 s, or from about 0.6 s to about 3.4 s, or from about 0.7 s to about 3.4 s, or from about 0.8 s to about 3.4 s, or from about 0.9 s to about 3.4 s, or from about 1.0 s to about 3.4 s, or from about 1.1 s to about 3.4 s, or from about 1.2 s to about 3.4 s, or from about 1.3 s to about 3.4 s, or from about 1.4 s to about 3.4 s, or from about 1.5 s to about 3.4 s, or from about 1.6 s to about 3.4 s, or from about 1.7 s to about 3.4 s, or from about 1.8 s to about 3.4 s, or from about 1.9 s to about 3.4 s, or from about 2.0 s to about 3.4 s, or from about 2.1 s to about 3.4 s, or from about 2.2 s to about 3.4 s, or from about 2.3 s to about 3.4 s, or from about 2.4 s to about 3.4 s, or from about 2.5 to about 3.4 s, or from about 2.6 s to about 3.4 s, or from about 2.7 s to about 3.4 s, or from about 2.8 s to about 3.4 s, or from about 2.9 s to about 3.4 s, or from about 3.0 s to about 3.4 s, or from about 3.1 s to about 3.4 s, or from about 3.2 s to about 3.4 s, or from about 3.3 s to about 3.4 s, or from about 0.1 s to about 3.3 s, or from about 0.2 s to about 3.3 s, or from about 0.3 s to about 3.3 s, or from about 0.4 s to about 3.3 s, or from about 0.5 s to about 3.3 s, or from about 0.6 s to about 3.3 s, or from about 0.7 s to about 3.3 s, or from about 0.8 s to about 3.3 s, or from about 0.9 s to about 3.3 s, or from about 1.0 s to about 3.3 s, or from about 1.1 s to about 3.3 s, or from about 1.2 s to about 3.3 s, or from about 1.3 s to about 3.3 s, or from about 1.4 s to about 3.3 s, or from about 1.5 s to about 3.3 s, or from about 1.6 s to about 3.3 s, or from about 1.7 s to about 3.3 s, or from about 1.8 s to about 3.3 s, or from about 1.9 s to about 3.3 s, or from about 2.0 s to about 3.3 s, or from about 2.1 s to about 3.3 s, or from about 2.2 s to about 3.3 s, or from about 2.3 s to about 3.3 s, or from about 2.4 s to about 3.3 s, or from about 2.5 s to about 3.3 s, or from about 2.6 s to about 3.3 s, or from about 2.7 s to about 3.3 s, or from about 2.8 to about 3.3 s, or from about 2.9 s to about 3.3 s, or from about 3.0 s to about 3.3 s, or from about 3.1 s to about 3.3 s, or from about 3.2 s to about 3.3 s, or from about 0.1 s to about 3.2 s, or from about 0.2 s to about 3.2 s, or from about 0.3 s to about 3.2 s, or from about 0.4 s to about 3.2 s, or from about 0.5 s to about 3.2 s, or from about 0.6 s to about 3.2 s, or from about 0.7 s to about 3.2 s, or from about 0.8 s to about 3.2 s, or from about 0.9 s to about 3.2 s, or from about 1.0 s to about 3.2 s, or from about 1.1 s to about 3.2 s, or from about 1.2 s to about 3.2 s, or from about 1.3 s to about 3.2 s, or from about 1.4 s to about 3.2 s, or from about 1.5 s to about 3.2 s, or from about 1.6 s to about 3.2 s, or from about 1.7 s to about 3.2 s, or from about 1.8 s to about 3.2 s, or from about 1.9 s to about 3.2 s, or from about 2.0 s to about 3.2 s, or from about 2.1 s to about 3.2 s, or from about 2.2 s to about 3.2 s, or from about 2.3 s to about 3.2 s, or from about 2.4 s to about 3.2 s, or from about 2.5 s to about 3.2 s, or from about 2.6 s to about 3.2 s, or from about 2.7 s to about 3.2 s, or from about 2.8 s to about 3.2 s, or from about 2.9 s to about 3.2 s, or from about 3.0 s to about 3.2 s, or from about 3.1 s to about 3.2 s, or from about 0.1 s to about 3.1 s, or from about 0.2 s to about 3.1 s, or from about 0.3 s to about 3.1 s, or from about 0.4 s to about 3.1 s, or from about 0.5 s to about 3.1 s, or from about 0.6 s to about 3.1 s, or from about 0.7 s to about 3.1 s, or from about 0.8 s to about 3.1 s, or from about 0.9 s to about 3.1 s, or from about 1.0 s to about 3.1 s, or from about 1.1 s to about 3.1 s, or from about 1.2 s to about 3.1 s, or from about 1.3 s to about 3.1 s, or from about 1.4 s to about 3.1 s, or from about 1.5 s to about 3.1 s, or from about 1.6 s to about 3.1 s, or from about 1.7 s to about 3.1 s, or from about 1.8 s to about 3.1 s, or from about 1.9 s to about 3.1 s, or from about 2.0 s to about 3.1 s, or from about 2.1 s to about 3.1 s, or from about 2.2 s to about 3.1 s, or from about 2.3 s to about 3.1 s, or from about 2.4 s to about 3.1 s, or from about 2.5 s to about 3.1 s, or from about 2.6 s to about 3.1 s, or from about 2.7 s to about 3.1 s, or from about 2.8 s to about 3.1 s, or from about 2.9 s to about 3.1 s, or from about 3.0 s to about 3.1 s, or from about 0.1 s to about 3.0 s, or from about 0.2 s to about 3.0 s, or from about 0.3 s to about 3.0 s, or from about 0.4 s to about 3.0 s, or from about 0.5 s to about 3.0 s, or from about 0.6 s to about 3.0 s, or from about 0.7 s to about 3.0 s, or from about 0.8 s to about 3.0 s, or from about 0.9 s to about 3.0 s, or from about 1.0 s to about 3.0 s, or from about 1.1 s to about 3.0 s, or from about 1.2 s to about 3.0 s, or from about 1.3 s to about 3.0 s, or from about 1.4 s to about 3.0 s, or from about 1.5 s to about 3.0 s, or from about 1.6 s to about 3.0 s, or from about 1.7 s to about 3.0 s, or from about 1.8 s to about 3.0 s, or from about 1.9 s to about 3.0 s, or from about 2.0 s to about 3.0 s, or from about 2.1 s to about 3.0 s, or from about 2.2 s to about 3.0 s, or from about 2.3 s to about 3.0 s, or from about 2.4 s to about 3.0 s, or from about 2.5 s to about 3.0 s, or from about 2.6 s to about 3.0 s, or from about 2.7 s to about 3.0 s, or from about 2.8 s to about 3.0 s, or from about 2.9 s to about 3.0 s, or from about 0.1 s to about 2.9 s, or from about 0.2 s to about 2.9 s, or from about 0.3 s to about 2.9 s, or from about 0.4 s to about 2.9 s, or from about 0.5 s to about 2.9 s, or from about 0.6 s to about 2.9 s, or from about 0.7 s to about 2.9 s, or from about 0.8 s to about 2.9 s, or from about 0.9 s to about 2.9 s, or from about 1.0 s to about 2.9 s, or from about 1.1 s to about 2.9 s, or from about 1.2 s to about 2.9 s, or from about 1.3 s to about 2.9 s, or from about 1.4 s to about 2.9 s, or from about 1.5 s to about 2.9 s, or from about 1.6 s to about 2.9 s, or from about 1.7 s to about 2.9 s, or from about 1.8 s to about 2.9 s, or from about 1.9 s to about 2.9 s, or from about 2.0 s to about 2.9 s, or from about 2.1 s to about 2.9 s, or from about 2.2 s to about 2.9 s, or from about 2.3 s to about 2.9 s, or from about 2.4 s to about 2.9 s, or from about 2.5 s to about 2.9 s, or from about 2.6 s to about 2.9 s, or from about 2.7 s to about 2.9 s, or from about 2.8 s to about 2.9 s, or from about 0.1 s to about 2.8 s, or from about 0.2 s to about 2.8 s, or from about 0.3 s to about 2.8 s, or from about 0.4 s to about 2.8 s, or from about 0.5 s to about 2.8 s, or from about 0.6 s to about 2.8 s, or from about 0.7 s to about 2.8 s, or from about 0.8 s to about 2.8 s, or from about 0.9 s to about 2.8 s, or from about 1.0 s to about 2.8 s, or from about 1.1 s to about 2.8 s, or from about 1.2 s to about 2.8 s, or from about 1.3 s to about 2.8 s, or from about 1.4 s to about 2.8 s, or from about 1.5 s to about 2.8 s, or from about 1.6 s to about 2.8 s, or from about 1.7 s to about 2.8 s, or from about 1.8 s to about 2.8 s, or from about 1.9 s to about 2.8 s, or from about 2.0 s to about 2.8 s, or from about 2.1 s to about 2.8 s, or from about 2.2 s to about 2.8 s, or from about 2.3 s to about 2.8 s, or from about 2.4 s to about 2.8 s, or from about 2.5 s to about 2.8 s, or from about 2.6 s to about 2.8 s, or from about 2.7 s to about 2.8 s, or from about 0.1 s to about 2.7 s, or from about 0.2 s to about 2.7 s, or from about 0.3 s to about 2.7 s, or from about 0.4 s to about 2.7 s, or from about 0.5 s to about 2.7 s, or from about 0.6 s to about 2.7 s, or from about 0.7 s to about 2.7 s, or from about 0.8 s to about 2.7 s, or from about 0.9 s to about 2.7 s, or from about 1.0 s to about 2.7 s, or from about 1.1 s to about 2.7 s, or from about 1.2 s to about 2.7 s, or from about 1.3 s to about 2.7 s, or from about 1.4 s to about 2.7 s, or from about 1.5 s to about 2.7 s, or from about 1.6 s to about 2.7 s, or from about 1.7 s to about 2.7 s, or from about 1.8 s to about 2.7 s, or from about 1.9 s to about 2.7 s, or from about 2.0 s to about 2.7 s, or from about 2.1 s to about 2.7 s, or from about 2.2 s to about 2.7 s, or from about 2.3 s to about 2.7 s, or from about 2.4 s to about 2.7 s, or from about 2.5 s to about 2.7 s, or from about 2.6 s to about 2.7 s, or from about 0.1 s to about 2.6 s, or from about 0.2 s to about 2.6 s, or from about 0.3 s to about 2.6 s, or from about 0.4 s to about 2.6 s, or from about 0.5 s to about 2.6 s, or from about 0.6 s to about 2.6 s, or from about 0.7 s to about 2.6 s, or from about 0.8 s to about 2.6 s, or from about 0.9 s to about 2.6 s, or from about 1.0 s to about 2.6 s, or from about 1.1 s to about 2.6 s, or from about 1.2 s to about 2.6 s, or from about 1.3 s to about 2.6 s, or from about 1.4 s to about 2.6 s, or from about 1.5 s to about 2.6 s, or from about 1.6 s to about 2.6 s, or from about 1.7 s to about 2.6 s, or from about 1.8 s to about 2.6 s, or from about 1.9 s to about 2.6 s, or from about 2.0 s to about 2.6 s, or from about 2.1 s to about 2.6 s, or from about 2.2 s to about 2.6 s, or from about 2.3 s to about 2.6 s, or from about 2.4 s to about 2.6 s, or from about 2.5 s to about 2.6 s, or from about 0.1 s to about 2.5 s, or from about 0.2 s to about 2.5 s, or from about 0.3 s to about 2.5 s, or from about 0.4 s to about 2.5 s, or from about 0.5 s to about 2.5 s, or from about 0.6 s to about 2.5 s, or from about 0.7 s to about 2.5 s, or from about 0.8 s to about 2.5 s, or from about 0.9 s to about 2.5 s, or from about 1.0 s to about 2.5 s, or from about 1.1 s to about 2.5 s, or from about 1.2 s to about 2.5 s, or from about 1.3 s to about 2.5 s, or from about 1.4 s to about 2.5 s, or from about 1.5 s to about 2.5 s, or from about 1.6 s to about 2.5 s, or from about 1.7 s to about 2.5 s, or from about 1.8 s to about 2.5 s, or from about 1.9 s to about 2.5 s, or from about 2.0 s to about 2.5 s, or from about 2.1 s to about 2.5 s, or from about 2.2 s to about 2.5 s, or from about 2.3 s to about 2.5 s, or from about 2.4 s to about 2.5 s, or from about 0.1 s to about 2.4 s, or from about 0.2 s to about 2.4 s, or from about 0.3 s to about 2.4 s, or from about 0.4 s to about 2.4 s, or from about 0.5 s to about 2.4 s, or from about 0.6 s to about 2.4 s, or from about 0.7 s to about 2.4 s, or from about 0.8 s to about 2.4 s, or from about 0.9 s to about 2.4 s, or from about 1.0 s to about 2.4 s, or from about 1.1 s to about 2.4 s, or from about 1.2 s to about 2.4 s, or from about 1.3 s to about 2.4 s, or from about 1.4 s to about 2.4 s, or from about 1.5 s to about 2.4 s, or from about 1.6 s to about 2.4 s, or from about 1.7 s to about 2.4 s, or from about 1.8 s to about 2.4 s, or from about 1.9 s to about 2.4 s, or from about 2.0 s to about 2.4 s, or from about 2.1 s to about 2.4 s, or from about 2.2 s to about 2.4 s, or from about 2.3 s to about 2.4 s, or from about 0.1 s to about 2.3 s, or from about 0.2 s to about 2.3 s, or from about 0.3 s to about 2.3 s, or from about 0.4 s to about 2.3 s, or from about 0.5 s to about 2.3 s, or from about 0.6 s to about 2.3 s, or from about 0.7 s to about 2.3 s, or from about 0.8 s to about 2.3 s, or from about 0.9 s to about 2.3 s, or from about 1.0 s to about 2.3 s, or from about 1.1 s to about 2.3 s, or from about 1.2 s to about 2.3 s, or from about 1.3 s to about 2.3 s, or from about 1.4 s to about 2.3 s, or from about 1.5 s to about 2.3 s, or from about 1.6 s to about 2.3 s, or from about 1.7 s to about 2.3 s, or from about 1.8 s to about 2.3 s, or from about 1.9 s to about 2.3 s, or from about 2.0 s to about 2.3 s, or from about 2.1 s to about 2.3 s, or from about 2.2 s to about 2.3 s, or from about 0.1 s to about 2.2 s, or from about 0.2 s to about 2.2 s, or from about 0.3 s to about 2.2 s, or from about 0.4 s to about 2.2 s, or from about 0.5 s to about 2.2 s, or from about 0.6 s to about 2.2 s, or from about 0.7 s to about 2.2 s, or from about 0.8 s to about 2.2 s, or from about 0.9 s to about 2.2 s, or from about 1.0 s to about 2.2 s, or from about 1.1 s to about 2.2 s, or from about 1.2 s to about 2.2 s, or from about 1.3 s to about 2.2 s, or from about 1.4 s to about 2.2 s, or from about 1.5 s to about 2.2 s, or from about 1.6 s to about 2.2 s, or from about 1.7 s to about 2.2 s, or from about 1.8 s to about 2.2 s, or from about 1.9 s to about 2.2 s, or from about 2.0 s to about 2.2 s, or from about 2.1 s to about 2.2 s, or from about 0.1 s to about 2.1 s, or from about 0.2 s to about 2.1 s, or from about 0.3 s to about 2.1 s, or from about 0.4 s to about 2.1 s, or from about 0.5 s to about 2.1 s, or from about 0.6 s to about 2.1 s, or from about 0.7 s to about 2.1 s, or from about 0.8 s to about 2.1 s, or from about 0.9 s to about 2.1 s, or from about 1.0 s to about 2.1 s, or from about 1.1 s to about 2.1 s, or from about 1.2 s to about 2.1 s, or from about 1.3 s to about 2.1 s, or from about 1.4 s to about 2.1 s, or from about 1.5 s to about 2.1 s, or from about 1.6 s to about 2.1 s, or from about 1.7 s to about 2.1 s, or from about 1.8 s to about 2.1 s, or from about 1.9 s to about 2.1 s, or from about 2.0 s to about 2.1 s, or from about 0.1 s to about 2.0 s, or from about 0.2 s to about 2.0 s, or from about 0.3 s to about 2.0 s, or from about 0.4 s to about 2.0 s, or from about 0.5 s to about 2.0 s, or from about 0.6 s to about 2.0 s, or from about 0.7 s to about 2.0 s, or from about 0.8 s to about 2.0 s, or from about 0.9 s to about 2.0 s, or from about 1.0 s to about 2.0 s, or from about 1.1 s to about 2.0 s, or from about 1.2 s to about 2.0 s, or from about 1.3 s to about 2.0 s, or from about 1.4 s to about 2.0 s, or from about 1.5 s to about 2.0 s, or from about 1.6 s to about 2.0 s, or from about 1.7 s to about 2.0 s, or from about 1.8 s to about 2.0 s, or from about 1.9 s to about 2.0 s, or from about 0.1 s to about 1.9 s, or from about 0.2 s to about 1.9 s, or from about 0.3 s to about 1.9 s, or from about 0.4 s to about 1.9 s, or from about 0.5 s to about 1.9 s, or from about 0.6 s to about 1.9 s, or from about 0.7 s to about 1.9 s, or from about 0.8 s to about 1.9 s, or from about 0.9 s to about 1.9 s, or from about 1.0 s to about 1.9 s, or from about 1.1 s to about 1.9 s, or from about 1.2 s to about 1.9 s, or from about 1.3 s to about 1.9 s, or from about 1.4 s to about 1.9 s, or from about 1.5 s to about 1.9 s, or from about 1.6 s to about 1.9 s, or from about 1.7 s to about 1.9 s, or from about 1.8 s to about 1.9 s, or from about 0.1 s to about 1.8 s, or from about 0.2 s to about 1.8 s, or from about 0.3 s to about 1.8 s, or from about 0.4 s to about 1.8 s, or from about 0.5 s to about 1.8 s, or from about 0.6 s to about 1.8 s, or from about 0.7 s to about 1.8 s, or from about 0.8 s to about 1.8 s, or from about 0.9 s to about 1.8 s, or from about 1.0 s to about 1.8 s, or from about 1.1 s to about 1.8 s, or from about 1.2 s to about 1.8 s, or from about 1.3 s to about 1.8 s, or from about 1.4 s to about 1.8 s, or from about 1.5 s to about 1.8 s, or from about 1.6 s to about 1.8 s, or from about 1.7 s to about 1.8 s, or from about 0.1 s to about 1.7 s, or from about 0.2 s to about 1.7 s, or from about 0.3 s to about 1.7 s, or from about 0.4 s to about 1.7 s, or from about 0.5 s to about 1.7 s, or from about 0.6 s to about 1.7 s, or from about 0.7 s to about 1.7 s, or from about 0.8 s to about 1.7 s, or from about 0.9 s to about 1.7 s, or from about 1.0 s to about 1.7 s, or from about 1.1 s to about 1.7 s, or from about 1.2 s to about 1.7 s, or from about 1.3 s to about 1.7 s, or from about 1.4 s to about 1.7 s, or from about 1.5 s to about 1.7 s, or from about 1.6 s to about 1.7 s, or from about 0.1 s to about 1.6 s, or from about 0.2 s to about 1.6 s, or from about 0.3 s to about 1.6 s, or from about 0.4 s to about 1.6 s, or from about 0.5 s to about 1.6 s, or from about 0.6 s to about 1.6 s, or from about 0.7 s to about 1.6 s, or from about 0.8 s to about 1.6 s, or from about 0.9 s to about 1.6 s, or from about 1.0 s to, about 1.6 s, or from about 1.1 s to about 1.6 s, or from about 1.2 s to about 1.6 s, or from about 1.3 s to about 1.6 s, or from about 1.4 s to about 1.6 s, or from about 1.5 s to about 1.6 s, or from about 0.1 s to about 1.5 s, or from about 0.2 s to about 1.5 s, or from about 0.3 s to about 1.5 s, or from about 0.4 s to about 1.5 s, or from about 0.5 s to about 1.5 s, or from about 0.6 s to about 1.5 s, or from about 0.7 s to about 1.5 s, or from about 0.8 s to about 1.5 s, or from about 0.9 s to about 1.5 s, or from about 1.0 s to about 1.5 s, or from about 1.1 s to about 1.5 s, or from about 1.2 s to about 1.5 s, or from about 1.3 s to about 1.5 s, or from about 1.4 s to about 1.5 s, or from about 0.1 s to about 1.4 s, or from about 0.2 s to about 1.4 s, or from about 0.3 s to about 1.4 s, or from about 0.4 s to about 1.4 s, or from about 0.5 s to about 1.4 s, or from about 0.6 s to about 1.4 s, or from about 0.7 s to about 1.4 s, or from about 0.8 s to about 1.4 s, or from about 0.9 s to about 1.4 s, or from about 1.0 s to about 1.4 s, or from about 1.1 s to about 1.4 s, or from about 1.2 s to about 1.4 s, or from about 1.3 s to about 1.4 s, or from about 0.1 s to about 1.3 s, or from about 0.2 s to about 1.3 s, or from about 0.3 s to about 1.3 s, or from about 0.4 s to about 1.3 s, or from about 0.5 s to about 1.3 s, or from about 0.6 s to about 1.3 s, or from about 0.7 s to about 1.3 s, or from about 0.8 s to about 1.3 s, or from about 0.9 s to about 1.3 s, or from about 1.0 s to about 1.3 s, or from about 1.1 s to about 1.3 s, or from about 1.2 s to about 1.3 s, or from about 0.1 s to about 1.2 s, or from about 0.2 s to about 1.2 s, or from about 0.3 s to about 1.2 s, or from about 0.4 s to about 1.2 s, or from about 0.5 s to about 1.2 s, or from about 0.6 s to about 1.2 s, or from about 0.7 s to about 1.2 s, or from about 0.8 s to about 1.2 s, or from about 0.9 s to about 1.2 s, or from about 1.0 s to about 1.2 s, or from about 1.1 s to about 1.2 s, or from about 0.1 s to about 1.1 s, or from about 0.2 s to about 1.1 s, or from about 0.3 s to about 1.1 s, or from about 0.4 s to about 1.1 s, or from about 0.5 s to about 1.1 s, or from about 0.6 s to about 1.1 s, or from about 0.7 s to about 1.1 s, or from about 0.8 s to about 1.1 s, or from about 0.9 s to about 1.1 s, or from about 1.0 s to about 1.1 s, or from about 0.1 s to about 1.0 s, or from about 0.2 s to about 1.0 s, or from about 0.3 s to about 1.0 s, or from about 0.4 s to about 1.0 s, or from about 0.5 s to about 1.0 s, or from about 0.6 s to about 1.0 s, or from about 0.7 s to about 1.0 s, or from about 0.8 s to about 1.0 s, or from about 0.9 s to about 1.0 s, or from about 0.1 s to about 0.9 s, or from about 0.2 s to about 0.9 s, or from about 0.3 s to about 0.9 s, or from about 0.4 s to about 0.9 s, or from about 0.5 s to about 0.9 s, or from about 0.6 s to about 0.9 s, or from about 0.7 s to about 0.9 s, or from about 0.8 s to about 0.9 s, or from about 0.1 s to about 0.8 s, or from about 0.2 s to about 0.8 s, or from about 0.3 s to about 0.8 s, or from about 0.4 s to about 0.8 s, or from about 0.5 s to about 0.8 s, or from about 0.6 s to about 0.8 s, or from about 0.7 s to about 0.8 s, or from about 0.1 s to about 0.7 s, or from about 0.2 s to about 0.7 s, or from about 0.3 s to about 0.7 s, or from about 0.4 s to about 0.7 s, or from about 0.5 s to about 0.7 s, or from about 0.6 s to about 0.7 s, or from about 0.1 s to about 0.6 s, or from about 0.2 s to about 0.6 s, or from about 0.3 s to about 0.6 s, or from about 0.4 s to about 0.6 s, or from about 0.5 s to about 0.6 s, or from about 0.1 s to about 0.5 s, or from about 0.2 s to about 0.5 s, or from about 0.3 s to about 0.5 s, or from about 0.4 s to about 0.5 s, or from about 0.1 s to about 0.4 s, or from about 0.2 s to about 0.4 s, or from about 0.3 s to about 0.4 s, or from about 0.1 s to about 0.3 s, or from about 0.2 s to about 0.3 s, or from about 0.1 s to about 0.2 s.

In an embodiment, the copolymer may have, for example, an $R_f$ value of 50% or greater. In an embodiment, the copolymer may have, for example, an $R_f$ value of from 50% to 100%, or from about 55% to 100%0, or from about 60% to 100%, or from about 65% to 100%, or from about 70% to 100%, or from about 75% to 100%, or from about 80% to 100%, or from about 85% to 100%, or from about 90% to 100%, or from about 95% to 100%, or from about 98% to 100%, or from about 99% to 100%, or from 50% to 99%, or from about 55% to 99%, or from about 60% to 99%, or from about 65% to 99%, or from about 70% to 99%, or from about 75% to 99%, or from about 80% to 99%, or from about 85% to 99%, or from about 90% to 99%, or from about 95% to 99%, or from about 98% to 99%, or from 50% to 98%, or from about 55% to 98%, or from about 60% to 98%, or from about 65% to 98%, or from about 70% to 98%, or from about 75% to 98%, or from about 80% to 98%, or from about 85% to 98%, or from about 90% to 98%, or from about 95% to 98%, or from 50% to 95%, or from about 55% to 95%, or from about 60% to 95%, or from about 65% to 95% or from about 70% to 95%, or from about 75% to 95%, or from about 80% to 95%, or from about 85% to 95%, or from about 90% to 95%, or from 50% to 90%, or from about 55% to 90%, or from about 60% to 90%, or from about 65% to 90%, or from about 70% to 90%, or from about 75% to 90%, or from about 80% to 90%, or from about 85% to 90%, or from 50% to 85%, or from about 55% to 85%, or from about 60% to 85%, or from about 65% to 85%, or from about 70% to 85%, or from about 75% to 85%, or from about 80% to 85%, or from 50% to 80%, or from about 55% to 80%, or from about 60% to 80%, or from about 65% to 80%, or from about 70% to 80%, or from about 75% to 80%, or from 50% to 75%, or from about 55% to 75%, or from about 60% to 75%, or from about 65% to 75%, or from about 70% to 75%, or from 50% to 70%, or from about 55% to 70%, or from about 60% to 70%, or from about 65% to 70%, or from 50% to 65%, or from about 55% to 65%, or from about 60% to 65%, or from 50% to 60%, or from about 55% to 60%, or from 50% to 55%. In an embodiment, the copolymer may have, for example, an $R_r$ value of 50% or greater. In an embodiment, the copolymer may have, for example, an $R_r$ value of from 50% to 100%, or from about 55% to 100%, or from about 60% to 100%, or from about 65% to 100%, or from about 70% to 100%, or from about 75% to 100%, or from about 80% to 100%, or from about 85% to 100%, or from about 90% to 100%, or from about 95% to 100%, or from about 98% to 100%, or from about 99% to 100%, or from 50% to 99%, or from about 55% to 99%, or from about 60% to 99%, or from about 65% to 99%, or from about 70% to 99%, or from about 75% to 99%, or from about 80% to 99%, or from about 85% to 99%, or from about 90% to 99%, or from about 95% to 99%, or from about 98% to 99%, or from 50% to 98%, or from about 55% to 98%, or from about 60% to 98%, or from about 65% to 98%, or from about 70% to 98%, or from about 75% to 98%, or from about 80% to 98%, or from about 85% to 98%, or from about 90% to 98%, or from about 95% to 98%, or from 50% to 95%, or from about 55% to 95%, or from about 60% to 95%, or from about 65% to 95%, or from about 70% to 95%, or from about 75% to 95%, or from about 80% to 95%, or from about 85% to 95%, or from about 90% to 95%, or from 50% to 90%, or from about 55% to 90%, or from about 60% to 90%, or from about 65% to 90%, or from about 70% to 90%, or from about 75% to 90%, or from about 80% to 90%, or from about 85% to 90%, or from 50% to 85%, or from about 55% to 85%, or from about 60% to 85%, or from about 65% to 85%, or from about 70% to 85%, or from about 75% to 85%, or from about 80% to 85%, or from 50% to 80%, or from about 55% to 80%, or from about 60% to 80%, or from about 65% to 80%, or from about 70% to 80%, or from about 75% to 80%, or from 50% to 75%, or from about 55% to 75%, or from about 60% to 75%, or from about 65% to 75%, or from about 70% to 75%, or from 50% to 70%, or from about 55% to 70%, or from about 60% to 70%, or from about 65% to 70%, or from 50% to 65%, or from about 55% to 65%, or from about 60 to 65%, or from 50% to 60%, or from about 55% to 60%, or from 50% to 55%.

When the temperature of the copolymer is below $T_{trans}$, the molecular motion of the segment is minimal. The increased order of the switching segment leads to the formation of rigid network points which holds the copolymer together. When the temperature of the copolymer is above $T_{trans}$, the rigid network points soften and the copolymer recovers its original shape. In an embodiment, the stimuli may be, for example, application of electromagnetic irradiation. In an embodiment, the stimuli may be, for example, changing temperature of the copolymer. In an embodiment, the first stimulus may be, for example, changing temperature of the copolymer. In an embodiment, the first stimulus may be, for example, decreasing temperature of the copolymer. In an embodiment, the first stimulus may be, for example, decreasing temperature of the copolymer to below $T_{trans}$. In an embodiment, the first stimulus may be, for example, application of electromagnetic irradiation to the copolymer. In an embodiment, the second stimulus may be, for example, changing temperature of the copolymer. In an embodiment, the second stimulus may be, for example, increasing temperature of the copolymer. In an embodiment, the second stimulus may be, for example, increasing temperature of the copolymer to above $T_{trans}$. In an embodiment, the second stimulus may be, for example, application of electromagnetic irradiation to the copolymer. In an embodiment, the electromagnetic irradiation may be, for example, UV, IR, or near-IR. In an embodiment, the electromagnetic irradiation may be, for example, UV. In an embodiment, the electromagnetic irradiation may be, for example, IR. In an embodiment, the electromagnetic irradiation may be, for example, near-IR.

In an embodiment, the copolymer may be, for example, a linear copolymer, a graft copolymer or a dendrimer copolymer. In an embodiment, the copolymer may be, for example, a linear copolymer. In an embodiment, the copolymer may be, for example, a graft copolymer. In an embodiment, the copolymer may be, for example, a dendrimer copolymer.

In an embodiment, the copolymer may be used, for example, to form a part of a polymer blend. In an embodiment, there is provided a polymer blend comprising at least one copolymer as described herein. In an embodiment, the polymer blend may comprise, for example, at least two copolymers as described herein. In an embodiment, the polymer blend may further comprise, for example, a semi crystalline homopolymer, a semicrystalline copolymer, a thermoplastic elastomer with linear chains, a thermoplastic elastomer with side chains or a dendritic structural element, a branched copolymer, or any combination thereof.

In an embodiment, there is also provided a polymer blend comprising at least one switching segment having a $T_{trans}$ from 10 to 70° C.; and at least one soft segment, wherein the polymer blend transforms from a first shape to a second shape by application of a first stimulus and the polymer blend transforms back to the first shape from the second shape by application of a second stimulus. In an embodiment, at least one of the soft segments may be, for example, a thermoplastic polymer. In an embodiment, at least one of the switching segments may be, for example, a thermoplastic polymer. In an embodiment, the polymer blend may be, for example, selected from the group consisting of physical mixtures of polymers, blends of polymers comprising switching segments with different $T_{trans}$ and soft segments having the same $T_{trans}$, blends of block copolymers wherein at least one of the segments of a first copolymer is miscible with at least one of the segments of a second copolymer, and blends of at least one multiblock copolymer and at least one homo- or copolymer.

In an embodiment, the copolymer or polymer blend as described herein may have, for example, at least one shape in memory. In an embodiment, the copolymer or polymer blend as described herein may have, for example, at least one shape in memory in addition to the first shape and the second shapes. For example, in an embodiment, the copolymer or the polymer blend may transform from a $1^{st}$ shape to a $2^{nd}$ shape by application of a $1^{st}$ stimulus, transform to a $3^{rd}$ shape by application of a $2^{nd}$ stimulus and transform back to the $1^{st}$ shape by application of a 3rd stimulus. For example, in an embodiment, the copolymer or the polymer blend may transform from a $1^{st}$ shape to a $2^{nd}$ shape by application of a $1^{st}$ stimulus, transform to a $3^{rd}$ shape by application of a $2^{nd}$ stimulus, transform to a $4^{th}$ shape by application of a $3^{rd}$ stimulus and transform back to the $1^{st}$ shape by application of a $4^{th}$ stimulus.

Those of ordinary skill in the art will appreciate that different methods may be used for processing the copolymer or polymer blend. In an embodiment, a solution of the copolymer may be solution casted to form a copolymer film of any shape, depending on the casting mold used.

The copolymer or polymer blend as described herein may be use, for example, as fibers for textiles or for manufacturing packaging materials.

The copolymer or polymer blend as described herein may be used, for example, as a biomaterial. As used herein, the expression "biomaterial" is used as it is normally understood to a person of skill in the art and often refers to a material which is used in situations and under circumstances where it comes into contact with cells and/or bodily fluids of a subject.

In an embodiment, the copolymer or polymer blend as described herein may be used for example, for encapsulation of drugs and/or biologically active agents. In an embodiment, there is provided a composition comprising at least one copolymer as described herein and a drug, a biologically active agent or a combination thereof. In an embodiment, there is provided a composition comprising the polymer blend as described herein and a drug, a biologically active agent or a combination thereof. In an embodiment, the drug and/or biologically active agent may be, for example, encapsulated in the copolymer or the polymer blend by dissolving the copolymer or the polymer blend and the drug and/or biologically active agent in a suitable solvent and preparing a solvent cast film with the drug and/or biologically active agent dispersed within the copolymer or the polymer blend matrix. Other methods of encapsulating the drug and/or biologically active agent in the copolymer or the polymer blend would be understood by those of ordinary skill in the art. The composition as described herein may further comprise one or more carriers, excipients or diluents acceptable for the mode of administration of the composition. Suitable carriers, excipients or diluents are those known in the art for use in such modes of administration. Suitable compositions may be formulated by means known in the art and their mode of administration and dose determined by the skilled practitioner.

In an embodiment, the drug may be, for example, a therapeutic agent, a diagnostic agent, or a prophylactic agent. In an embodiment, the biologically active agent may be, for example, a therapeutic agent, a diagnostic agent, or a prophylactic agent. In an embodiment, the drug or biologically active agent may be, for example, an antiproliferative agent, an antineoplastic agent, an antimitotic agent, an anti-inflammatory agent, an antiplatelet agent, an anticoagulant agent, an antifibrin agent, an antithrombin agent, an antibiotic, an antiallergic agent, an antioxidant agent or any combination thereof. In an embodiment, the drug or biologically active agent may be, for example, an anti-inflammatory agent. In an embodiment, the drug may be, for example, a nonsteroidal anti-inflammatory drug (NSAID). In an embodiment, the drug may be, for example, an NSAID including ibuprofen, naproxen, nabumetone, ketorolac, sulindac and diclofenac. In an embodiment, the drug may be, for example, a hydrophobic drug. In an embodiment, the drug may be, for example, paclitaxel.

An "effective amount" of the composition described herein includes a therapeutically effective amount or a prophylactically effective amount. A "therapeutically effective amount" refers to an amount effective, at dosages and for periods of time necessary, to achieve the desired therapeutic result, such as increased life span or increased life expectancy. A therapeutically effective amount of a drug or biologically active agent may vary according to factors such as the disease state, age, sex, and weight of the subject, and the ability of the drug or biologically active agent to elicit a desired response in the subject. A therapeutically effective amount is also one in which any toxic or detrimental effects of the drug or biologically active agent are outweighed by the therapeutically beneficial effects. A "prophylactically effective amount" refers to an amount effective, at dosages and for periods of time necessary, to achieve the desired prophylactic result, such as increased life span, increased life expectancy or prevention of the progression of the disease state. Typically, a prophylactic dose is used in subjects prior to or at an earlier stage of disease, so that a prophylactically effective amount may be less than a therapeutically effective amount. It is to be noted that dosage values may vary with the severity of the condition to be alleviated. For any particular subject, specific dosage regimens may be adjusted over time according to the individual. The amount of the drug or biologically active agent in the composition may vary according to factors such as the disease state, age, sex, and weight of the subject. As used herein, a "subject" may be a human, non-human primate, rat, mouse, cow, horse, pig, sheep, goat, dog, cat, etc.

In an embodiment, the copolymer, polymer blend, or composition as described herein may be used, for example, for biomedical applications. In an embodiment, the copolymer, polymer blend, or composition as described herein may be used, for example, in the manufacture of an article. For example, the copolymer, polymer blend, or composition as described herein may be used to manufacture a portion of the article or the whole article itself. In an embodiment, there is provided a method of manufacturing an article comprising the copolymer, polymer blend, or composition as described herein. In an embodiment, the copolymer, polymer blend or composition as described herein may be used, for example, as a coating for an article. In an embodiment, the method may comprise, for example, depositing or disposing over at least a portion of the article a coating comprising the copolymer, polymer blend, or composition as described herein. In an embodiment, there is provided a coating comprising the copolymer as described herein. In another embodiment, there is provided a coating comprising the polymer blend as described herein. In a further embodiment, there is provided a coating comprising the composition as described herein. In an embodiment, the coating may be for an article. As used herein, the expression "coating" is used as it is normally understood to a person of skill in the art and often refers to a layer or a film of material deposited directly or indirectly over at least a portion of the surface of the article. Deposited directly means that the coating is applied directly to the exposed surface of the article whereas deposited indirectly means that the coating is applied to an intervening layer that is deposited directly or indirectly over at least a portion of the surface of the article. Methods for directly or indirectly depositing the copolymer, polymer blend, or composition as described herein over at least a portion of the surface of the article would be known to or understood by those of ordinary skill in the art. In an embodiment, there is provided an article comprising the copolymer as described herein. In another embodiment, there is provided an article comprising the polymer blend as described herein. In a further embodiment, there is provided an article comprising the composition as described herein. In an embodiment, the body of the article may comprise, for example, a drug, a biologically active agent, or a combination thereof. In an embodiment, the article may be, for example, implantable. In an embodiment, the article may be, for example, a medical device. In an embodiment, the article may be, for example, a medical device selected from the group consisting of stents, catheters, prosthetics, grafts, screws, pins, pumps, sutures and meshes.

In an embodiment, there is provided a method for preventing or treating a disorder using the copolymer, polymer blend, or composition as described herein. In an embodiment, for example, the copolymer or polymer blend as described herein may be used as a drug delivery vehicle to deliver the drug or biologically active agent to a target cell or tissue in a subject. In an embodiment, for example, the composition as described herein may be used for preventing or treating a disorder. In an embodiment, for example, the article as described herein may be used for preventing or treating a disorder. In an embodiment, for example, there is provided a method of preventing or treating a disorder, the method comprising implanting in a subject the article as described herein. For example, the copolymer or polymer blend as described herein may have the second shape during delivery of the article to the target site in the subject, after reaching the target site, the second stimulus may be applied to the copolymer or polymer blend to transform it back to the first shape. Methods of applying the first and/or second stimulus would be known to and understood by those of ordinary skill in the art. In an embodiment, for example, where the stimulus is thermal, the stimulus may be provided by, for example, a laser, ultrasonic wave, high frequency wave, infrared radiation, hot air stream or hot water. In an embodiment, the stimulus may be provided by, for example, a catheter. In an embodiment, the disorder may be, for example, atherosclerosis, thrombosis, restenosis, or vulnerable plaque. In an embodiment, the article as described herein may be used, for example, for repairing damaged arteries. For example, the article may comprise the copolymer or polymer blend as described herein with an inflammatory agent encapsulated within the copolymer or polymer blend matrix. For example, the inflammatory agent may be an NSAID such as, ibuprofen, naproxen, nabumetone, ketorolac, sulindac or diclofenac. In an embodiment, the copolymer or polymer blend as described herein may be used as a superelastic and/or thermal shape recovery material in biomedical applications. For example, in an embodiment, the article as described herein may be a vena cava filter. In an embodiment, the vena cava filter may comprise the copolymer or polymer blend as described herein, and may be used, for example, in one of the outer heart chambers to trap blood clots. Blood clots may cause a fatality if allowed to travel freely around the blood circulation system. In an embodiment, the vena cava filter traps these small clots, preventing them from entering the pulmonary system and causing a pulmonary embolism. In an embodiment, the vena-cava filter may be introduced in a compact cylindrical form. In an embodiment, the cylindrical form may be, for example, about 2.0-2.5 mm in diameter and when released it forms an umbrella shape. In an embodiment, the vena cava filter may comprise a wire mesh with spacing sufficiently small to trap clots.

In an embodiment, the copolymer or polymer blend as described herein may be used as superelastic and/or thermal shape recovery materials for orthodontic applications. In an embodiment, the copolymer or polymer blend as described herein may be used, for example, as an archwire. In an embodiment, for example, there is provided an archwire comprising the copolymer or polymer blend as described herein. Archwires made of conventional materials have been employed as a corrective measure for misaligned teeth for many years. Owing to the limited "stretch" and tensile properties of these wires, considerable forces are applied to teeth, which can cause a great deal of discomfort. When the teeth succumb to the corrective forces applied, the wire has to be re-tensioned. Visits may be needed to the orthodontist for re-tensioning every three to four weeks in the initial stages of treatment.

The present invention includes isomers such as geometrical isomers, optical isomers based on asymmetric carbon, stereoisomers and tautomers and is not limited by the description of the formula illustrated for the sake of convenience.

Various alternative embodiments and examples of the invention are described herein. These embodiments and examples are illustrative, and not limiting.

EXAMPLES

Example 1: Synthesis and Characterization of Poly(PDMS/PCL Urethane)s

Poly(PDMS/PCL urethane)s were prepared by randomly coupling PCL and PDMS segment blocks using the isocyanate, 1,6-hexamethlyene diisocyanate (HMDI) with dibutyltin dilaurate as the catalyst. The synthesis of the poly (PDMS/PCL urethane)s is presented in Scheme 1.

Scheme 1 depicts a synthesis of poly(PDMS/PCL urethane)s.

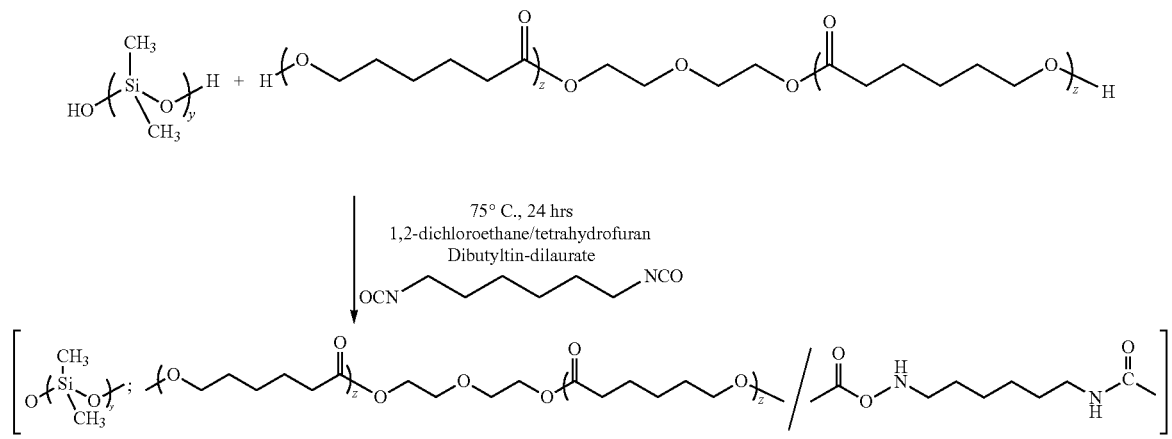

Materials

Poly(ε-caprolactone)-diol (PCL-diol) with $M_n$ of ca. 2000 g·mol$^{-1}$ and dihydroxyl-terminated poly(dimethylsiloxane) (PDMS) was purchased from Aldrich. The $M_n$ and $M_w$ of PCL-diol were found to be 1040 and 2320 g·mol$^{-1}$, respectively. The $M_n$ and $M_w$ of PDMS were found to be 1890 and 2060 g·mol$^{-1}$, respectively. Dibutyltin dilaurate (95%), 1,6-hexamethylene diisocyanate (HMDI) (98%), anhydrous tetrahydrofuran, hexane and 1,2-dichloroethane (99.8%) were purchased from Aldrich. 1,2-dichloroethane was distilled over CaH$_2$ before use.

Synthesis of Poly(PDMS/PCL Urethane)s

In a typical preparation, 8.0527 g of dihydroxy-terminated poly(dimethylsiloxane) (PDMS-diol) and 12.266 g of dihydroxy-terminated poly(ε-caprolactone) (PCL-diol) was dried in a 3-necked round bottom flask (RBF) in vacuo at 80° C. overnight. On the next day, the temperature was lowered to 60° C. and the RBF was purged with nitrogen and kept under nitrogen atmosphere. 15 mL of anhydrous tetrahydrofuran (THF) was added to the molten polymers to dissolve the sample. Upon dissolution, 1.44 g of hexamethylene diisocyanate (HMDI) and 4 drops of dibutyltin dilaurate (~16 mg) were added and the solution was allowed to stir at 60° C. After 1 hour, the solution was observed to thicken and the solution turned from clear to milky. At this juncture, 10 mL of anhydrous dichloroethane (DCE) was added to the mixture and the solution was allowed to stir. It was observed that the solution became clearer upon addition of DCE. After a further 3.5 hours, 20 mL of anhydrous DCE was added and the temperature was raised to 75° C. This reaction was allowed to proceed for a further 24 h. Chloroform (200 mL) was added and the polymer was solution cast to form a polymer film. The film was dried overnight in air at room temperature. Following that the film was washed in hexane for 2 hours and then dried overnight in vacuo at 45° C.

Molecular Characterization

Gel permeation chromatography (GPC) analysis was carried out with a Shimadzu SCL-10A and LC-8A system equipped with a Phenogel in series and a Shimadzu RID-10A refractive index detector. THF was used as eluent at a flow rate of 1.0 ml/min at 45° C. Monodisperse polystyrene standards of $M_n$ between $1.36 \times 10^3$ and $1.29 \times 10^6$ were used to obtain a calibration curve. $^1$H NMR (400 MHz) and $^{13}$C NMR (100 MHz) spectra were recorded on a Bruker AV-400 NMR spectrometer at room temperature. The $^1$H NMR measurements were carried out with an acquisition time of 3.2 s, a pulse repetition time of 2.0 s, a 30 degree pulse width, 5208 Hz spectral width, and 32 K data points. Chemical shift was referred to the solvent peaks (PPM=7.3 for CHCl$_3$).

Figure 2:
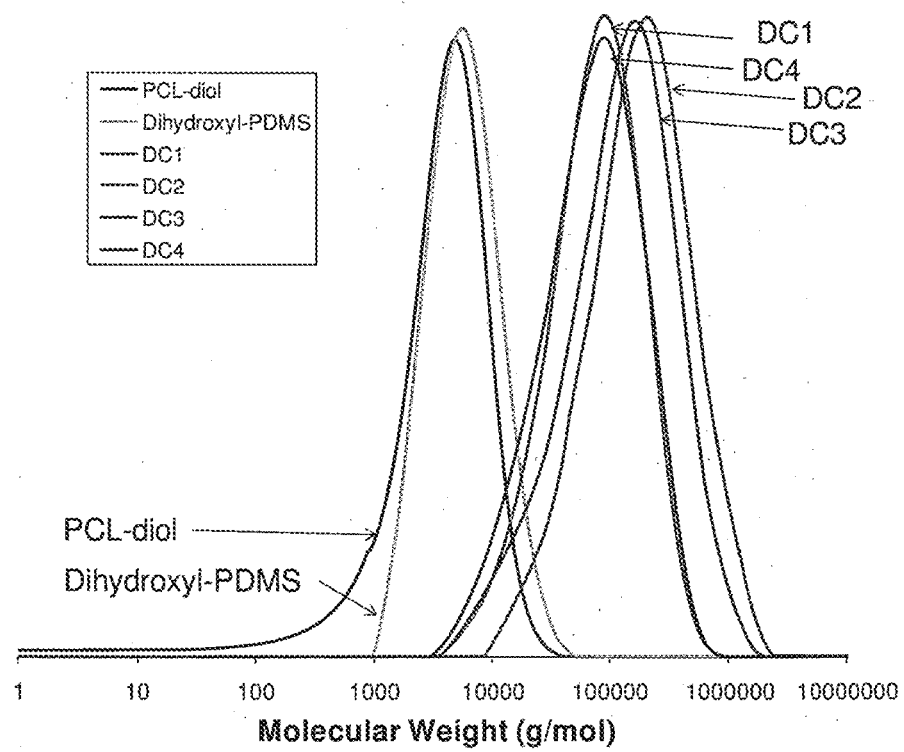
FIG. 2 depicts GPC diagrams of poly(PDMS/PCL urethane)s, DC1 to DC4 and its PCL and PDMS precursors.

A series of random multiblock poly(PDMS/PCL urethane)s with different PDMS and PCL contents were synthesized, and their molecular weights and molecular weight distributions were determined by GPC (Table 1). Typical GPC chromatographs of the poly(PDMS/PCL urethane)s show a unimodal peak in the GPC chromatograph as shown in FIG. 2. The non-overlapping nature of the plot with those of corresponding precursors indicates that a complete reaction took place with no unreacted precursor remaining. The molecular weights of the poly(PDMS/PCL urethane)s and their polydispersities are tabulated in Table 1. The copolymers can be processed into different shapes by melt processing and they are soluble in common organic solvents such as chloroform, tetrahydrofuran, N,N-dimethylformamide and 1,4-dioxane.

Molecular Characterization

TABLE 1

Molecular Characteristics of Poly(PDMS/PCL urethane)s

| Sample ID | $M_w$ (×10$^4$)[a]/ g · mol$^{-1}$ | $M_n/M_w$[a] | Content (wt %)[b] PDMS | PCL |
|---|---|---|---|---|
| PCL | 12.2 | 1.89 | 0 | 100.0 |
| DC1 | 12.0 | 2.13 | 3.9 | 96.1 |
| DC2 | 28.7 | 2.31 | 40.6 | 59.4 |
| DC3 | 21.3 | 2.75 | 19.0 | 81.0 |
| DC4 | 11.9 | 2.43 | 19.3 | 80.7 |

[a]Determined by GPC,
[b]Determined by $^1$H NMR

Figure 3:
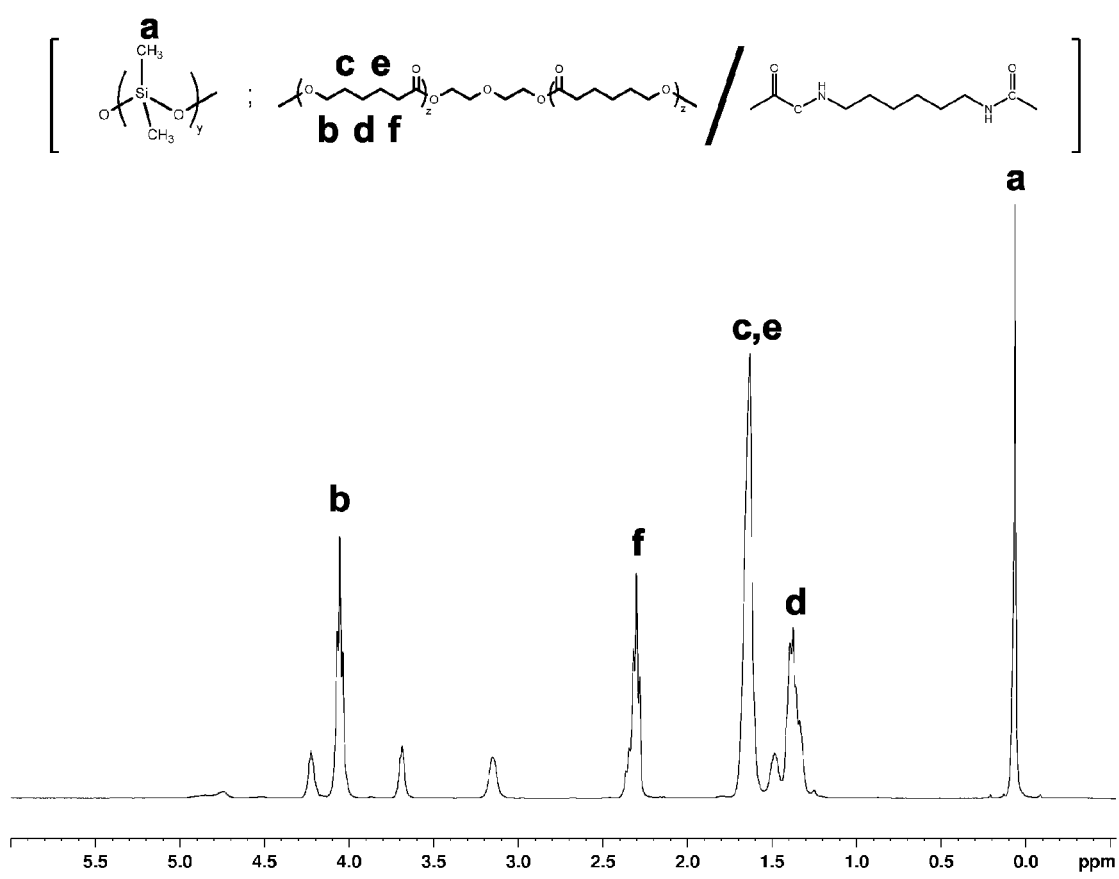
FIG. 3 depicts $^1$H NMR of poly(PDMS/PCL urethane), DC1 in CDCl$_3$.

The chemical structure of poly(PDMS/PCL urethane)s was verified by $^1$H NMR spectroscopy as shown in FIG. 3. FIG. 3 shows the $^1$H NMR spectrum of DC1 in CDCl$_3$, in which all proton signals belonging to PCL and PDMS segments are confirmed. Signals corresponding to methylene protons alpha to the ester group of PCL segments are observed at 4.04 ppm and the signals at 0.66 ppm are assigned to the methyl protons of PDMS. As the content of HMDI among the starting materials is below 1 wt %, the PDMS and PCL contents of the poly(PDMS/PCL urethane)s could be determined from the integration ratio of resonances at 0.66 and 4.02 ppm within the limits of $^1$H NMR precision, and the results are shown in Table 1.

$^1$H NMR (CDCl$_3$) of poly(PDMS/PCL urethane), DC1: δ (ppm) 0.66 (—CH$_3$ of PDMS segment), 1.34-1.40 (OCH$_2$CH$_2$CH$_2$CH$_2$CH$_2$CO), 1.49 (OOCNHCH$_2$CH$_2$CH$_2$CH$_2$CH$_2$CH$_2$NHCOO), 1.61-1.66 (OCH$_2$CH$_2$CH$_2$CH$_2$CH$_2$CO), 2.28-2.37 (OCH$_2$CH$_2$CH$_2$CH$_2$CH$_2$CO), 3.15 (OOCNHCH$_2$CH$_2$CH$_2$CH$_2$CH$_2$CH$_2$NHCOO), 3.68-3.70 (OOCNHCH$_2$CH$_2$CH$_2$CH$_2$CH$_2$CH$_2$NHCOO), 4.04-4.07 (OCH$_2$CH$_2$CH$_2$CH$_2$CH$_2$CO), 4.23 (OOCNHCH$_2$CH$_2$CH$_2$CH$_2$CH$_2$CH$_2$NHCOO).

Example 2: Thermal Analysis of Poly(PDMS/PCL Urethane)s

Thermogravimetric analyses (TGA) were carried out on a TA Instruments SDT 2960. Samples were heated at 20° C. min$^{-1}$ from room temperature to 800° C. in a dynamic nitrogen atmosphere (flow rate=70 ml min$^{-1}$). Differential scanning calorimetry (DSC) measurements were performed using a TA Instruments 2920 differential scanning calorimeter equipped with an autocool accessory and calibrated using indium. The following protocol was used for each sample: the first heating run started from 25° C. to 150° C. at 5° C. min$^{-1}$, with an isothermal step, holding at 150° C. for 5 min, the second cooling run started from 150 to −30° C. at 5° C. min$^{-1}$, with an isothermal step, holding at −30° C. for 5 min, and finally the second heating run took place from −30 to 150° C. at 5° C. min$^{-1}$. Data were collected from the first and second heating runs, as well as the second cooling run. Transition temperatures were taken as peak maxima.

Figure 4:
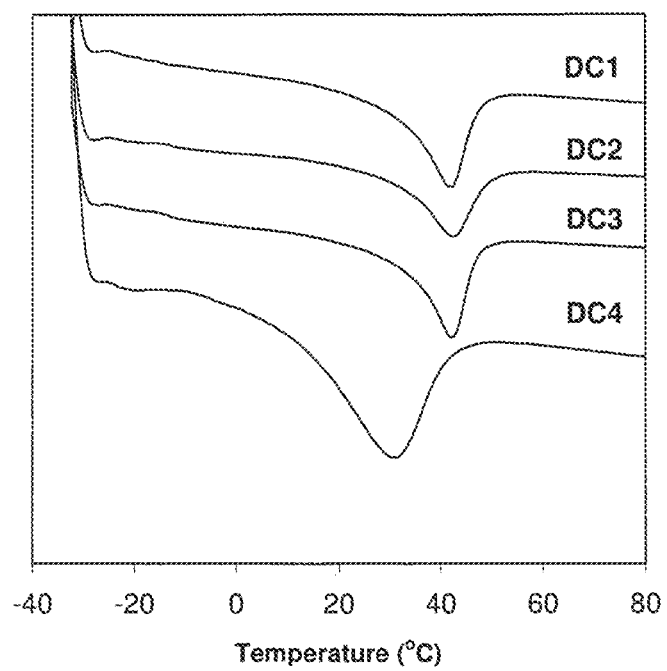
FIG. 4 depicts DSC curves of poly(PDMS/PCL urethane)s in the second heating run.

Crystallization behavior of PCL segments in the poly (PDMS/PCL urethane)s was studied using DSC. FIG. 4 shows the DSC thermogram of the copolymers obtained in the second heating run after the removal of thermal history. PCL is a semi-crystalline polymer that has a melting temperature at about 40° C. The crystalline content and the enthalpy of melting of the polymers are tabulated in Table 2.

TABLE 2

Transition Temperatures, Corresponding Enthalpies, Crystallinity, and Decomposition Temperatures for Poly(PDMS/PCL urethane)s

| Sample ID | $T_m^a$ (° C.) | $\Delta H_m^b$ (J/g) | $X_c^c$ (%) | $T_d^d$ (° C.) |
|---|---|---|---|---|
| PCL | 43.5 | 72.1 | 50.8 | 349.7 |
| DC1 | 42.0 | 31.3 | 22.0 | 352.2 |
| DC2 | 42.5 | 37.3 | 26.3 | 334.3 |
| DC3 | 42.3 | 31.0 | 21.9 | 335.4 |
| DC4 | 31.0 | 25.4 | 17.9 | 332.0 |

[a]Melting point determined in the DSC second heating run.
[b]Enthalpy change during melting determined in the DSC second heating run.
$\Delta H_m = \Delta H_f/W_f$, where $\Delta H_f$ is the area of the endothermic peak for the PCL segment read from the DSC curves and $W_f$ is the weight fraction of the corresponding segment.
[c]Crystallinity calculated from melting enthalpies. Reference value of 142.0 J/g for completely crystallized PCL was used.
[d]Temperature at which 10% mass loss has occurred from TGA curves.

Example 3: Measurement of Thermo-Mechanical Properties of Poly(PDMS/PCL Urethane)s Linear viscoelastic thermo-mechanical properties of the materials were determined using dynamic mechanical analysis (DMA). A TA Instruments DMA 2980 apparatus was employed in tensile mode with a preload force of 0.01 N, an oscillation amplitude of 20 μm, static stress/dynamic stress amplitude ratio ("force tracking") of 150%, and an oscillation frequency of 1 Hz. Samples were cut from the cast films in dimensions of 10 mm (length)×3.0 mm (width)×0.4 mm (thickness). After loading each film specimen at room temperature under tensile stress, they were cooled to T=−100° C., thermally equilibrated, and finally ramped to 130° C. at a rate of 3° C./min.

Figure 5:
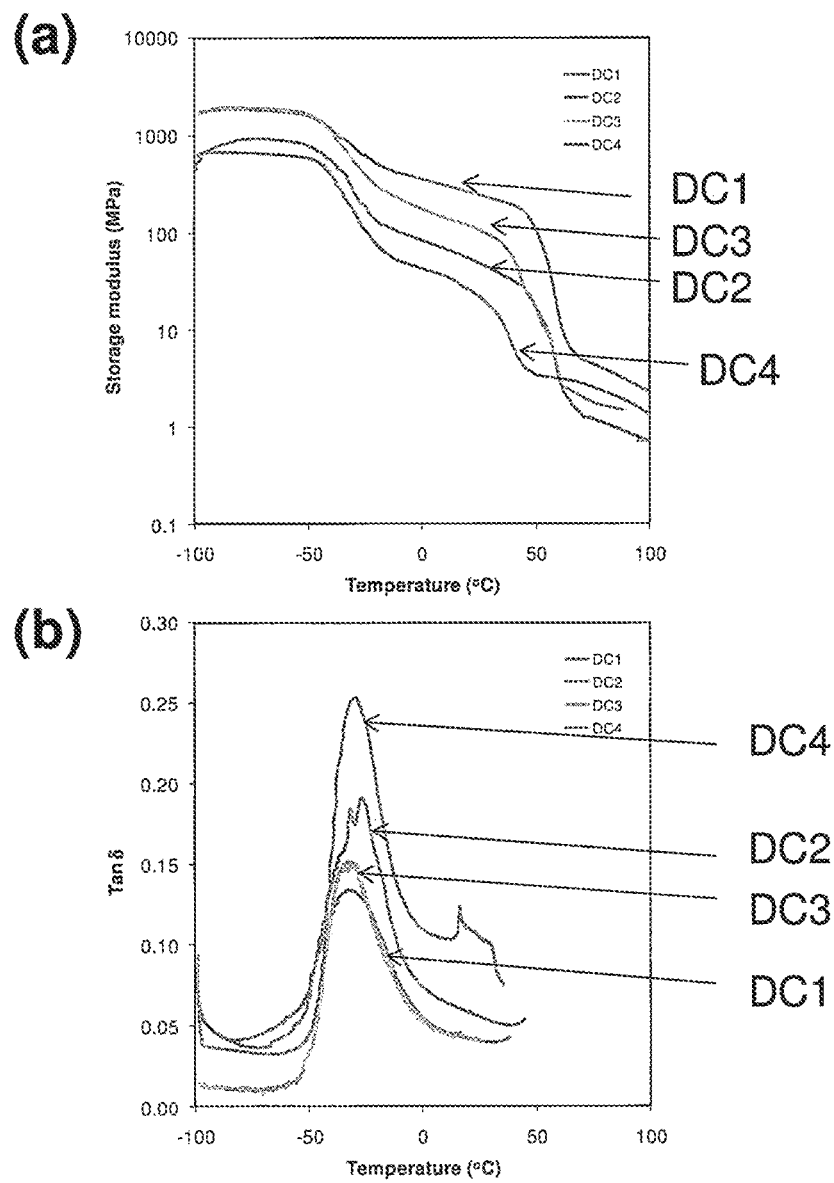
FIG. 5 depicts tensile storage modulus of the poly(PDMS/PCL urethane)s.

FIGS. 5(*a* and *b*) show the change in the tensile storage modulus and tan(δ) data for the poly(PDMS/PCL urethane)s with a variation in temperature. The $T_g$ values and the temperatures corresponding to the peaks of tap (δ) are tabulated in Table 3. The polymer samples show two thermal transitions. The first transition corresponds to the glass transition of the PCL segments and the second transition can be attributed to the melting of the PCL crystals. When the temperature is low at about −60° C. ($T<T_g$), the polymer films are glassy. The elastic modulus is in the GPa range. When the temperature is higher than $T_g$, the storage modulus of the polymer films drop drastically, ranging from about 70-800 MPa. When comparing DC3 and DC4, it was observed that an increase in the molecular weight of the polymer increases the storage modulus of the polymer. In addition, an increase in the PCL content also increases the storage modulus of the polymer. This modulus drops by a further two decades when the temperature is raised to about 40° C. Without being bound by theory, it is believed that this change is attributed to the melting of the PCL crystallites which further softens the polymer. When raised to a higher temperature up to 100° C., the polymer did not become fully molten. Without being bound by theory, it is believed that this is due to the presence of the hexamethylene group present in the urethane linking group which holds the polymer chains together.

TABLE 3

Glass Transition Temperature, Tan δ peak values, and Storage Modulus at 25° C. for Poly(PDMS/PCL urethane)s

| Sample ID | $T_g{}^a$ (° C.) | Tan(δ) $^b$ (° C.) | Storage Modulus at 25° C.$^c$ (MPa) |
|---|---|---|---|
| PCL | −66.5 | −33.6 | 184.4 |
| DC1 | −63.6 | −31.4 | 246.9 |
| DC2 | −64.0 | −29.6 | 49.1 |
| DC3 | −56.4 | −31.6 | 109.9 |
| DC4 | −58.7 | −29.1 | 22.5 |

$^a T_g$ was determined from the onset of the Tan δ peak.
$^b$ Peak value of Tan δ.
$^c$ Storage modulus determined from DMA results.

Example 4: Dynamic Mechanical Analysis and Shape Memory Characterization of Poly(PDMS/PCL Urethane)s Shape memory properties of the materials were determined using dynamic mechanical analysis (DMA). A TA Instruments DMA 2980 apparatus was employed in controlled force mode with a preload force of 0.01 N, an oscillation amplitude of 20 μm, static stress/dynamic stress amplitude ratio ("force tracking") of 150%, and an oscillation frequency of 1 Hz. Samples were cut from the cast films in dimensions of 10 mm (length)×3.0 mm (width)×0.4 mm (thickness). In a typical example, for shape memory characterization of DC1, samples (in tension) were equilibrated at 60° C., elongated to a force of 0.6 N at a rate of 0.03 N/min (the strain was recorded as $\epsilon_m$), cooled to 5° C. at a rate of 2.5° C./min, unloaded to 0.001 N at a rate of 0.1 N/min (the strain was recorded as $\epsilon_u$), then heated to 60° C. at a ramp rate of 2.5° C./min to observe the recovery (the strain was recorded as $\epsilon_r$). This process was then repeated four more times on the same sample in order to obtain multiple cycles. The shape recovery ratio ($R_r$) and the shape fixity ratio ($R_f$) were calculated by the following equations:

$$\text{Shape recovery ratio, } R_r = \left[\frac{\varepsilon_m - \varepsilon_r(N)}{\varepsilon_m - \varepsilon_r(N-1)}\right] \times 100\%$$

$$\text{Shape fixity ratio, } R_f = \left[\frac{\varepsilon_u(N)}{\varepsilon_m}\right] \times 100\%$$

Measuring the Speed of Shape Memory Recovery

Samples were cut from the cast films in dimensions of 10 mm (length)×3.0 mm (width)×0.4 mm (thickness). All samples were prestretched to 200% strain before experiments. A Nikon camera was used to record the recovery of the polymer film as it was immersed into warm water at 45° C. The obtained .mov file was converted into a .wmv file and the frame analysis of the recovery process was done using Windows Movie Maker software. In all, five samples were used and the average recovery time was recorded.

Figure 6:
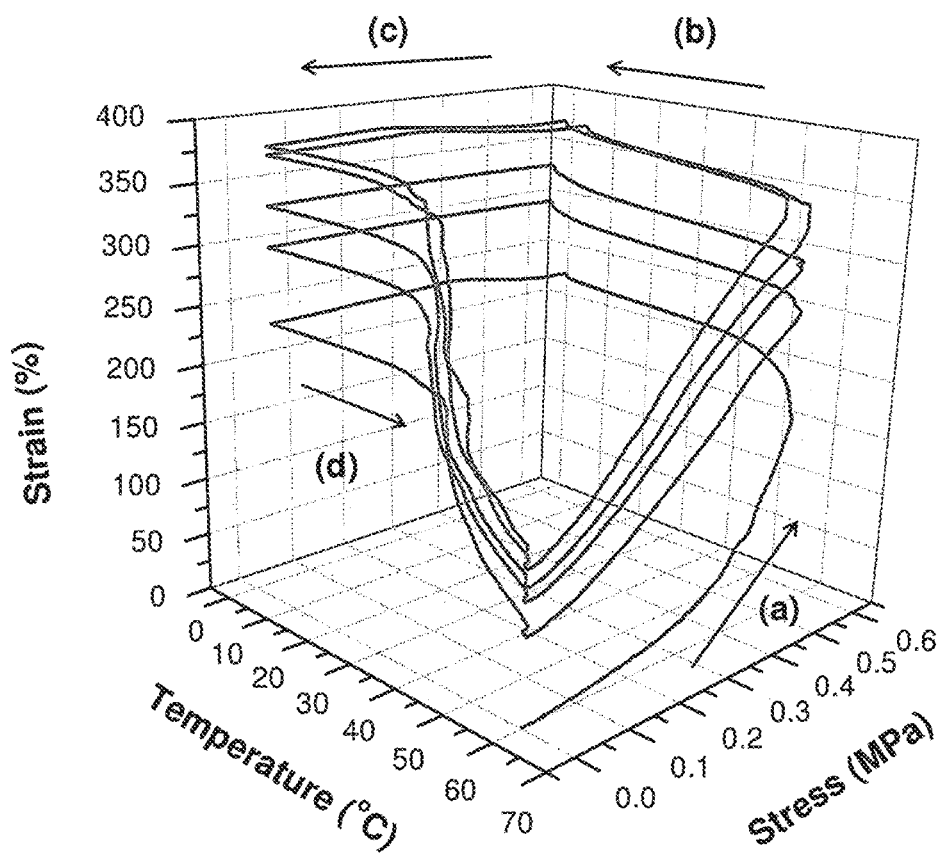
FIG. 6 depicts the shape memory thermocycle (5 cycles) for DC1.

Thermocyclic shape memory experiments were carried out for the polymer films using DMA. FIG. 6 shows the sequence of five one-way shape memory cycle for DC1. The asterisk marks the beginning of the cycle and the arrows denote the different stages of the thermocycle: (a) elongation at 60° C., (b) shape fixation with cooling, (c) unloading to evaluate shape fixity and (d) heating to 60° C. to induce recovery.

Figure 7:
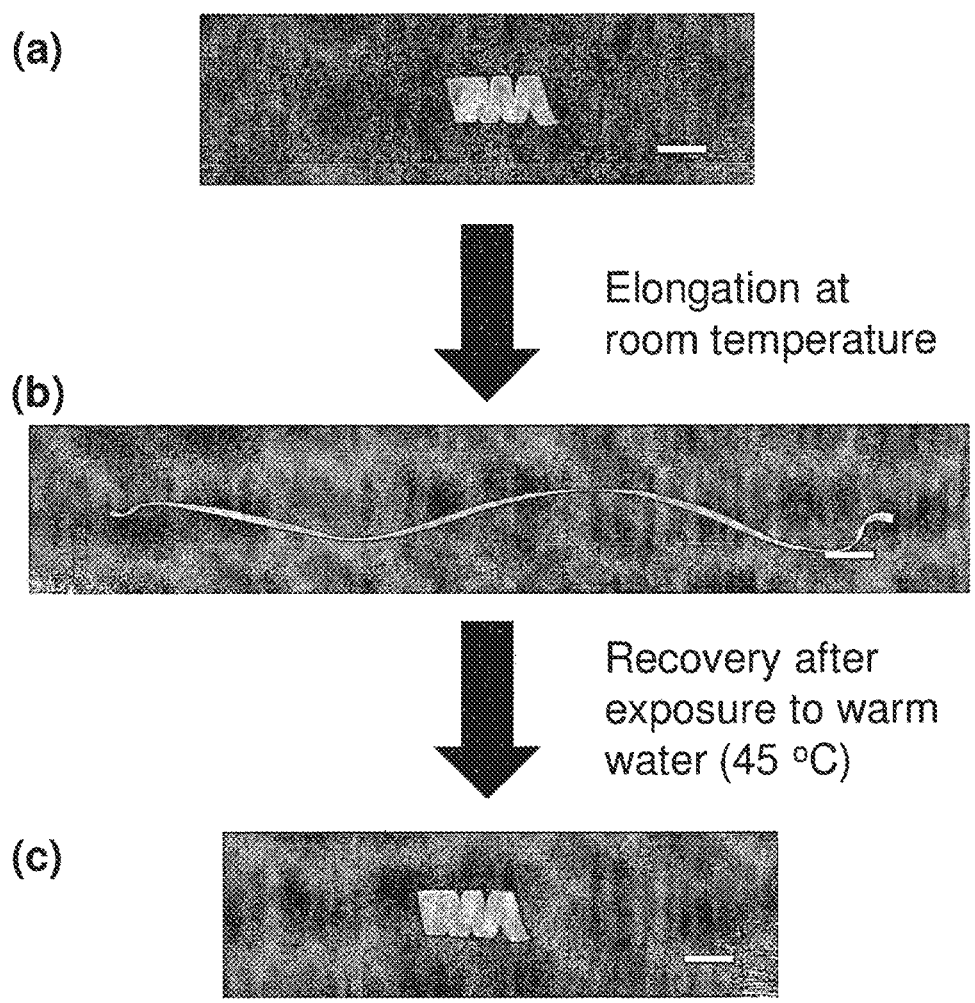
FIG. 7 depicts thermally induced shape memory behavior of poly(PDMS/PCL urethane), DC1.

In particular, the polymers were deformed at 60° C., above the $T_m$ of the polymer (determined by DSC experiments). The shape was then allowed to fix at 5° C. to allow for crystallization to take place. Finally, the load was removed to observe the shape fixing and recovery of the original shape of the polymer was carried out by elevating the temperature to 60° C. Good shape fixing properties were observed for the polymers as evidenced by the non-retraction of the polymer films upon the removal of the external applied force at the shape fixing temperature of 5° C. Recovery was also generally very good for the 5 cycles (>90%), after an initial conditioning cycle of the polymers (Table 4). The photographs of the shape memory polymers before deformation, after deformation and after recovery are shown in FIG. 7: (a) The permanent spiral shape was obtained by molding at 60° C., followed by fixation at 25° C., (b) The temporary elongated shape was made at 25° C. and (c) The recovered shape was obtained after 1 is immersion in water at 45° C. The scale bar in FIG. 7 denotes 1 cm.

TABLE 4

Shape Fixity and Shape Recovery Ratio for Poly(PDMS/PCL urethane)s

| Sample ID | | 0 → 1 | 1 → 2 | 2 → 3 | 3 → 4 | 4 → 5 | Recovery Speed (s) |
|---|---|---|---|---|---|---|---|
| PCL | $R_f$ | 100.1% | 99.3% | 99.1% | 100.2% | 99.2% | 1.121 ± 0.223 |
| | $R_r$ | 70.2% | 85.2% | 88.7% | 89.5% | 91.7% | |

TABLE 4-continued

Shape Fixity and Shape Recovery Ratio for Poly(PDMS/PCL urethane)s

| Sample ID | | 0 → 1 | 1 → 2 | 2 → 3 | 3 → 4 | 4 → 5 | Recovery Speed (s) |
|---|---|---|---|---|---|---|---|
| DC1 | $R_f$ | 101.8% | 100.4% | 99.9% | 100.6% | 99.5% | 0.620 ± 0.156 |
|  | $R_r$ | 69.5% | 88.3% | 95.5% | 94.2% | 96.5% |  |
| DC2 | $R_f$ | 89.1% | 96.0% | 99.5% | 98.1% | 98.3% | 0.460 ± 0.083 |
|  | $R_r$ | 85.5% | 82.4% | 93.7% | 94.7% | 98.8% |  |
| DC3 | $R_f$ | 54.6% | 58.9% | 67.3% | 68.0% | 82.8% | 0.464 ± 0.195 |
|  | $R_r$ | 51.3% | 107.7% | 75.9% | 96.4% | 87.9% |  |
| DC4 | $R_f$ | 34.0% | 73.4% | 71.8% | 72.4% | 72.2% | 0.592 ± 0.175 |
|  | $R_r$ | 30.4% | 86.9% | 92.5% | 94.9% | 93.1% |  |

Applications in biomedical devices may require high strain changes. If the desired insertion technique is through a small orifice (eg, the use of a catheter), a large change in the shape dimensions may be in order to implant the device and subsequently to recover the original dimensions for use in the desired site. In FIG. 5 and Table 4, a good shape recovery ratio of >90% is shown for high strains of at least 200% for the polymers.

Samples DC1-CD4 exhibited fast recovery processes as evidenced by the fast recovery speeds (Table 4). Without being bound by theory, it is believed that the recovery process depends on the elasticity entropy of the material and that decreases in response time of the copolymer may be attributed to entropy elasticity. In general, an increase in entropy results in a decrease in the recovery time. When an ordered state is stretched or compressed, the entropy of the system decreases due to increased ordering of the domains within a material. As the original state is high in entropy, recovery to the original state becomes more energetically favourable (going from a low entropic state to a high entropic state). Without being bound by theory, it is believed that the incorporation of soft amorphous segment decreases order within the matrix and increases entropy of the original system leading to a faster recovery after deformation.

Example 5: Cytotoxicity Studies on Poly(PDMS/PCL Urethane)s

Cell Culture

L929 mouse fibroblasts were obtained from ATCC and cultivated in DMEM containing 10% fetal bovine serum (FBS) and 1% penicillin/streptomycin. Cells grow as a monolayer and were passaged upon confluence using trypsin (0.5% w/v in PBS). L929 cells were harvested from culture by incubating in trypsin solution for 15 min. The cells were centrifuged and the supernatent was discarded. 3 mL of serum-supplemented DMEM was added to neutralize any residual trypsin. The cells were resuspended in serum-supplemented DMEM at a concentration of $2 \times 10^4$ cells $mL^{-1}$. Cells were cultivated at 37° C. and 5% $CO_2$.

Cytotoxicity of the Film Extracts

In vitro cytotoxicity tests on the extracts of the polymer films were performed by (3-(4,5-dimethylthiazol-2-yl)-5-(3-carboxymethoxyphenyl)-2-(4-sulfophenyl)-2H-tetrazolium) (MTS) assay in a 96-well cell culture plate using the CellTiter 96 AQueous Non-Radioactive Cell Proliferation Assay Kit (Promega). Sterile films were cut into discs (diameter=8 mm) and incubated with the complete culture medium in the ratio of 6 $cm^2$ $mL^{-1}$ between the surface area of the material and the volume of extraction vehicle. The medium, containing the extracts from the films, was aseptically diluted at volume ratio of 1:0, 1:1, 1:2, 1:4 and 1:8 using the culture medium. Cells were seeded at a density of $3 \times 10^4$ cells. $mL^{-1}$ into wells containing 100 microliters of the respective extracts. The wells containing only the cells and the culture medium served as negative controls. The plates were incubated at 37° C. in a humidified 5% $CO_2$ atmosphere. After 3 days, 20 microliters of phenazine methosulfate (PMS) solution was added to each well. After 3 h of incubation at 37° C., the absorbance of the formazan product was measured at 492 nm using a spectrophotometer (TECAN SpectrofluorPlus).

Figure 8:
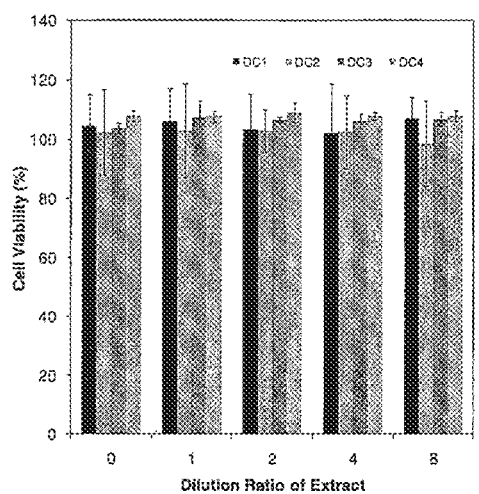
FIG. 8 depicts cell viability incubated with known concentrations of the aqueous-based extracts from poly(PDMS/PCL urethane) films.

The cytotoxicity of the copolymers films was evaluated by incubating the cells with the extracts of the copolymer films over a period of 48 h at 37° C. The extraction procedures were performed based on the ISO 10993 protocol. The aim of this experiment is to simulate clinical conditions so as to determine the potential toxicological hazard without affecting the chemical or mechanical properties of the copolymer film. Quantification of the cytotoxic response was done using the MTS assay as shown in FIG. 8. Aqueous extracts of the copolymer film do not show significant cytotoxicity against L929 cells, regardless of the dilution factor. From the MTS assay results of the extracts of the copolymer films, the polymer is expected to be safe for biomedical applications.

Example 6: Hydrolysis Experiments

Figure 9:
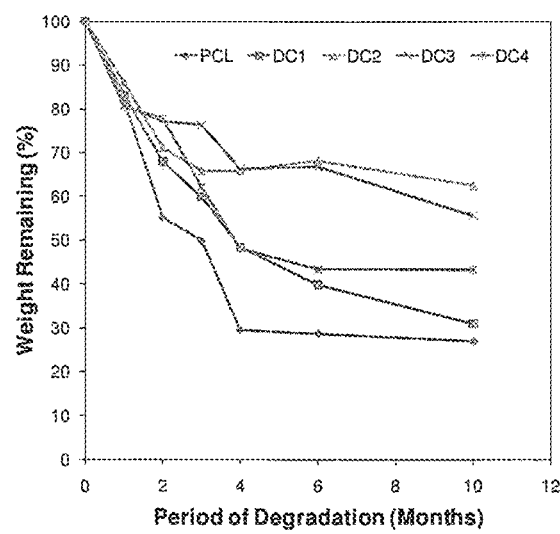
FIG. 9 depicts mass loss profiles of poly(PDMS/PCL urethane) films following hydrolytic degradation in the presence of lipase.

The degradation of the copolymer films were evaluated by mass loss studies. Copolymer films were prepared by solvent casting from a 10 wt % chloroform solution. The resultant films were dried in vacuo at 50° C. for 2 days, cut into discs (diameter, 8 mm; thickness, 80 mm) and used for the degradation experiments. Film samples (~15 mg) were placed in tubes containing 10 mL of aqueous buffer solutions at 37° C. Buffer solutions of pH 7.4 were used. The pH 7.4 buffer solution contained 8.0 g of NaCl, 0.2 g of KCl, 1.44 g of $Na_2HPO_4$, and 0.24 g of $K_2H_2PO_4$ in 1 L of solution. *Pseudomonas* lipase was added at a concentration of 0.01 mg/mL of buffer for accelerated degradation. The weight loss of the polymer films after degradation was evaluated with Residual Weight (%), which was defined by Eq. (1):

$$\text{Residual Weight} = W_t/W_0 \times 100\% \quad (1)$$

where $W_0$ and $W_t$ were the initial weight and the weight at time t, respectively. $W_t$ was obtained after drying the samples at 50° C. under vacuum for 1 week. Copolymer films incubated in buffer solutions without the lipase showed negligible mass loss after 10 months (<1%). The incorporation of the poly(dimethylsiloxane) slowed down the degradation of the copolymers (FIG. 9). The degradation rates of the polymers were in the following order PCL>DC1>DC4. When the molecular weight of the copolymer is increased, the degradation rate of the copolymers slowed down. The higher molecular weight copolymers, DC2 and DC3 degraded much more slowly than DC4.

Although various embodiments of the invention are disclosed herein, many adaptations and modifications may be made within the scope of the invention in accordance with the common general knowledge of those skilled in this art. Such modifications include the substitution of known equivalents for any aspect of the invention in order to achieve the same result in substantially the same way.

Numeric ranges are inclusive of the numbers defining the range. The word "comprising" is used herein as an open-ended term, substantially equivalent to the phrase "including, but not limited to", and the word "comprises" has a corresponding meaning. As used herein, the singular forms "a", "an" and "the" include plural referents unless the context clearly dictates otherwise. Thus, for example, reference to "a thing" includes more than one such thing.

Citation of references herein is not an admission that such references are prior art to the present Invention. Any priority document(s) and all publications, including but not limited to patents and patent applications, cited in this specification are incorporated herein by reference as if each individual publication were specifically and individually indicated to be incorporated by reference herein and as though fully set forth herein.

The invention includes all embodiments and variations substantially as hereinbefore described and with reference to the examples and drawings.

What is claimed is:

1. A shape memory block copolymer comprising:
   at least one switching segment having a $T_{trans}$ from 10 to 70° C. and selected from the group consisting of polyhydroxy acids, poly(ether ester)s, polyorthoesters, poly(amino acids), synthetic poly(amino acids), polyanhydrides, polycarbonates, poly(hydroxyalkanoate)s and poly(ε-caprolactone)s; and
   at least one soft segment comprising a poly (alkylene glycol);
   wherein:
      the copolymer has a molecular weight, $M_w$, of about 50,000 g/mol to about 1,000,000 g/mol,
      the switching segments and soft segments are randomly arranged in the copolymer,
      at least one of the switching segments is linked to at least one of the soft segments by at least one linkage,
      the copolymer transforms from a first shape to a second shape by application of a first stimulus and the copolymer transforms back to the first shape from the second shape by application of a second stimulus, and
      the copolymer has a response time of less than 10 seconds, wherein the response time is the time for the copolymer to transform back to the first shape from the second shape after application of the second stimulus using a sample pre-stretched to 200% strain and having dimensions of 0.4 mm×3 mm×10 mm.

2. The copolymer of claim 1, wherein at least one of the linkages is selected from the group consisting of urethane, ester, urea, carbonate, anhydride, amide and orthoester linkages.

3. The copolymer of claim 1, wherein at least one of the linkages is a urethane linkage.

4. The copolymer of claim 1, wherein at least one of the switching segments is linked to at least one of the soft segments by two urethane linkages and the copolymer further comprises alkylene groups between segments, the alkylene groups connected to each segment by a urethane linkage.

5. The copolymer of claim 1, wherein at least one of the switching segments and/or at least one of the soft segments comprises a biodegradable region or at least one of the switching segments is linked to at least one of the soft segments through a biodegradable linkage.

6. The copolymer of claim 1, wherein at least one of the switching segments has crystallinity below $T_{trans}$.

7. The copolymer of claim 1, wherein at least one of the switching segments is a thermoplastic polymer and/or at least one of the soft segments is a thermoplastic polymer.

8. The copolymer of claim 1, wherein at least one of the switching segments is poly(ε-caprolactone) (PCL).

9. The copolymer of claim 1, wherein at least one of the soft segments is an amorphous segment.

10. The copolymer of claim 1, wherein at least one of the soft segments has a melting temperature, $T_m$, of from about −30 to about 30° C.

11. The copolymer of claim 1, which comprises cross-linking and has a molecular weight, $M_w$, of about 50,000 g/mol to about 1,000,000 g/mol prior to cross-linking.

12. The copolymer of claim 1, which is soluble in an organic solvent.

13. The copolymer of claim 1, which has a response time of from 0.3 to 2 seconds, wherein the response time is the time for the copolymer to transform back to the first shape from the second shape after application of the second stimulus.

14. The copolymer of claim 1, wherein the first stimulus is changing a temperature of the copolymer or applying electromagnetic irradiation to the copolymer and the second stimulus is changing a temperature of the copolymer or applying electromagnetic irradiation to the copolymer.

15. The copolymer of claim 1, wherein the first stimulus is decreasing the temperature of the copolymer to below $T_{trans}$ and the second stimulus is increasing the temperature of the copolymer to above $T_{trans}$.

16. The copolymer of claim 1, which is biocompatible.

17. A composition comprising the copolymer as defined in claim 1 and a therapeutic agent, a diagnostic agent, a prophylactic agent, or any combination thereof.

18. An article comprising the composition as defined in claim 17.

19. The copolymer of claim 1, wherein:
   at least one of the switching segments has crystallinity below $T_{trans}$;
   at least one of the soft segments has a melting temperature, $T_m$, of from about −30 to about 30° C. and comprises a poly (alkylene glycol);
   at least one of the linkages is selected from the group consisting of urethane, ester, urea, carbonate, anhydride, amide and orthoester linkages; and
   the first stimulus is changing a temperature of the copolymer or applying electromagnetic irradiation to the copolymer and the second stimulus is changing a temperature of the copolymer or applying electromagnetic irradiation to the copolymer.

20. The copolymer of claim 1, wherein:
   at least one of the switching segments has crystallinity below $T_{trans}$ and is a poly(ε-caprolactone);
   at least one of the soft segments has a melting temperature, $T_m$, of from about −30 to about 30° C. and is a poly (alkylene glycol);
   at least one of the switching segments is linked to at least one of the soft segments by two urethane linkages and the copolymer further comprises hexamethylene groups between segments, the hexamethylene groups connected to each segment by a urethane linkage;

the first stimulus is decreasing the temperature of the copolymer to below $T_{trans}$ and the second stimulus is increasing the temperature of the copolymer to above $T_{trans}$; and the response time is from 0.3 to 2 seconds.

* * * * *